(12) United States Patent
Felder-Flesch et al.

(10) Patent No.: US 8,404,216 B2
(45) Date of Patent: Mar. 26, 2013

(54) DENDRITIC CHELATED COMPOUNDS, METHODS FOR MAKING THE SAME AND PHARMACEUTICAL COMPOSITIONS CONTAINING THE SAME

(75) Inventors: Delphine Felder-Flesch, Rouffach (FR); Jérôme Steibel, Strasbourg (FR); Annabelle Bertin, Strasbourg (FR)

(73) Assignees: Centre National de la Recherche Scientifique, Paris (FR); Universite Louis Pasteur, Strasbourg (FR)

( * ) Notice: Subject to any disclaimer, the term of this patent is extended or adjusted under 35 U.S.C. 154(b) by 774 days.

(21) Appl. No.: 12/444,817

(22) PCT Filed: Oct. 9, 2007

(86) PCT No.: PCT/FR2007/001645
§ 371 (c)(1), (2), (4) Date: Jun. 1, 2009

(87) PCT Pub. No.: WO2008/043911
PCT Pub. Date: Apr. 17, 2008

(65) Prior Publication Data
US 2010/0104512 A1  Apr. 29, 2010

(30) Foreign Application Priority Data
Oct. 9, 2006 (FR) ...................................... 06 08836

(51) Int. Cl.
*A61B 5/055* (2006.01)
*A61K 51/00* (2006.01)
*A61M 36/14* (2006.01)

(52) U.S. Cl. ..................... 424/9.361; 424/9.3; 424/9.36; 424/9.362; 424/9.363; 424/9.364; 424/9.365; 424/1.11; 424/1.65

(58) Field of Classification Search .................. 424/1.11, 424/1.65, 9.3, 9.36, 9.361, 9.362, 9.363, 424/9.364, 9.365
See application file for complete search history.

(56) References Cited

U.S. PATENT DOCUMENTS

| 5,527,524 | A | * | 6/1996 | Tomalia et al. | .............. | 424/1.33 |
| 5,601,802 | A | * | 2/1997 | Hemmi et al. | .............. | 424/9.363 |
| 6,982,324 | B1 | | 1/2006 | Lu et al. | | |
| 2006/0093555 | A1 | * | 5/2006 | Torres et al. | ................ | 424/9.36 |
| 2006/0165601 | A1 | | 7/2006 | Josephk et al. | | |
| 2010/0298403 | A1 | * | 11/2010 | Tack et al. | .................. | 514/44 A |

FOREIGN PATENT DOCUMENTS

| FR | 2 867 473 | 3/2004 |
| FR | 2 883 562 | 3/2005 |
| WO | WO 2006/088958 | 2/2006 |
| WO | WO 2006/033766 | 3/2006 |

OTHER PUBLICATIONS

Manen et al., Eur. J. Org. Chem., 2002, p. 3189-3197.*
Oar et al., Chem. Mater., 2005, 17, p. 2267-2275.*
Weiner, et al. "Dendrimer-Based Metal Chelates: A New Class of Magnetic Resonance Imaging Contrast Agents", Magnetic Resonance in Medicine, 31: 1-8, 1994.
Imbert, et al. "Synthesis and iron (III) complexing ability of Cac-CAM, a new analog of enterobactin processing a free carboxylic anchor arm. Comparative studies with TRENCAM", New J. Chem, 24: 281-288, 2000.
Thomas, et al. "Partition Cefficients (Free Ligands and their Iron (III) Complexes) and Lipophilic Behavior of New Abiotic Chelators. Correlation to Biological Activity", Bioorganic & Medicinal Chemistry Letters 9: 3035-3040, 1999.

* cited by examiner

*Primary Examiner* — Michael G Hartley
*Assistant Examiner* — Leah Schlientz
(74) *Attorney, Agent, or Firm* — Morgan, Lewis & Bockius LLP

(57) ABSTRACT

The invention relates to dendritic chelated compounds, to methods for producing the same and to pharmaceutical compositions containing the same. The dendritic chelated complexes of the present invention have the following formula (I): $[[MC]E_n\text{-}[D]_m\text{-}X_{1p1}X_{2p2}X_{3p3}X_{4p4}]_z^- zB^+$ (I), where m is a magnetic or scintigraphic marker, C is a chelating agent of the marker M, E is a spacer, n=0 or 1, D is compound capable of forming a dendritic structure, m is an integer equal to 1 or 2 or 4, $X_1$ is a group increasing the complex lipophily, p1 is an integer from 0 to 12, $X_2$ is a group increasing the complex specificity for a particular organ, p2 is an integer equal to 1 or 2 or 4, $X_3$ is a group having a therapeutic activity, p3 is an integer equal to 0, 1, 2 or 4, $X_4$ is a $CH_3$ group, p4 is an integer from 0 to 12, B is a counter-ion, z is an integer equal to 0, 1, 2, 3 or 4. The invention can be used in the field of pharmacy, more precisely in medical imaging.

46 Claims, No Drawings

DENDRITIC CHELATED COMPOUNDS, METHODS FOR MAKING THE SAME AND PHARMACEUTICAL COMPOSITIONS CONTAINING THE SAME

CROSS-REFERENCE TO RELATED APPLICATIONS

The present application is a U.S. National Phase Application of International Application PCT/FR2007/001645, filed Oct. 9, 2007, which claims the benefit of French Application No. 0608836, filed Oct. 9, 2006, all of which are herein incorporated by reference in their entirety.

BACKGROUND OF THE INVENTION

The invention relates to dendritic chelated complexes, to methods for producing same and to pharmaceutical compositions containing same.

Magnetic resonance imaging and nuclear medicine have become essential research tools in the life sciences field since they give noninvasive and nontraumatic access to both anatomical and functional information in varied medical fields.

One main line of current development concerns functional imaging, which constitutes in particular a basic tool in understanding the mechanisms involved in neurodegenerative diseases such as Alzheimer's disease, Parkinson's disease or multiple sclerosis (MS).

The products used in magnetic resonance imaging are contrast agents known as magnetic contrast agents, including a marker, termed magnetic marker.

The magnetic contrast agents that currently exist are compounds in which the magnetic marker is gadolinium or manganese.

In nuclear medicine, contrast agents are called scintigraphic contrast agents and include a marker termed scintigraphic marker. The scintigraphic marker that is currently most commonly used is technetium-99m.

All these contrast agents must satisfy restrictive specifications. Thus, they must have good biocompatibility, low toxicity, high stability in the organism, be effective at a low concentration and, in addition, if possible, be specific for the organs or tissues targeted (vectorization provided by the functions grafted onto the ligand).

But, the products currently placed on the market and described in the literature, in addition to the fact that they may exhibit toxicity, in particular hepatic toxicity, have low stability in the organism and are not specific for the organs or tissues targeted.

Thus, Masato Hito et al., in their article published in *Magnet. Res. Imag.* 2006, 24, 625-630, describe a contrast agent which is a gadolinium chelate, in which the chelating agent is diethylenetriaminepentaacetic acid (DTPA), as having specificity for the brain.

However, this is not a real vectorization of the chelate to the brain.

This is because 4% of contrast agents injected always go to the brain. Now, in the molecule proposed by Masato Hito, the number of gadolinium atoms per molecule is three, whereas in the prior contrast agents, there is just one gadolinium atom per molecule of contrast agent. Therefore, with the molecule proposed by Masato Hito, this is in reality an increase in the concentration of gadolinium arriving in the brain, and not a real vectorization of the chelate to the brain.

Furthermore, this product exhibits liver toxicity.

Min Liu et al. have proposed, in *Bioconj. chem.* 2005, 16, 1126-1132, contrast agents in which the marker is technetium-99m, the chelating agent is diethylenetriaminepentaacetic acid (DTPA) and the ligand is a polyethylene glycol (PEG)-based polymer.

This product, which can be used in nuclear medicine, binds to the liver and is eliminated by the kidneys, thereby enabling imaging of the kidneys.

This product, once again, is not specific for a particular organ within the meaning of vectorization of the contrast agent.

Furthermore, in this polyethylene glycol-based polymeric approach, there is a problem of reproducibility of the synthesis of the radiopharmaceutical, and also of sufficient and known purity of the product obtained, as in any polymeric synthesis.

Jakub Rudovsky et al. in Chem. Commun., 2005, 2390-2392, have proposed a dendritic gadolinium (3+) complex of a DOTA (2,2',2'',2'''-(1,4,7,10-tetraazacyclotetradecane-1,4,7,10-tetrayl)tetraacetic acid) analog of formula:

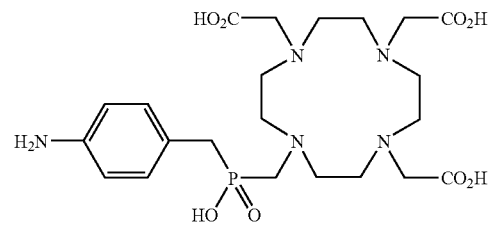 [SMILES: Nc1ccc(CP(=O)(O)CN2CCN(CC(=O)O)CCN(CC(=O)O)CCN(CC(=O)O)CC2)cc1]

However, in this case, the complex is at the periphery of the dendrimer, thereby preventing functionalization of the complex itself with a vectorizing agent, all the ends of the dendrimer being occupied by the chelate.

Paula Baia et al., in *Eur. J. Inorg. Chem.* 2005, 2110-2119, have described diethylenetriaminepentaacetic acid bisamide glycoconjugate lanthanide (III) chelates.

These molecules are composed of a $Gd^{3+}$ ion-chelating structure linked to a dendritic structure of polyamide type, onto which a vectorizing agent, which is a beta-galactosyl residue, is grafted.

The vectorization is vectorization for targeting the liver.

However, in addition to the fact that this product is specific for the liver and not for the brain, it exhibits toxicity due to the polyamide dendrimer.

Patent application US No. 2006/0165601A1 describes dendritic compounds for chelating metal cations, in particular $Gd^{3+}$ cations.

In these compounds, the $Gd^{3+}$-chelating agent is diethylenetriaminepentaacetic acid (DTPA) and the core of the dendritic structure is a polyol compound, the dendrites of this dendritic structure being composed of polyethylene glycol chains ending with a hydroxyl (OH) or amine ($NH_2$) or O—($C_1$ to $C_{10}$)alkyl group.

However, these compounds have no specificity for the brain and have no particular vascular remanence compared with the known imaging products.

Thus, among all the existing and described contrast agents, to date, the only product which has a certain "specificity" for the brain is the diethylenetriaminepentaacetic acid-derived $Gd^{3+}$ ion chelate described by Masato Hito, which does not display any real vectorization to the brain and which, in addition, exhibits hepatic toxicity.

All the other contrast agents are specific for the liver or for the kidneys and can exhibit toxicity for the organism, in particular in the case of the product proposed by Paula Baia et al., due to the use of polyamide dendrimers.

BRIEF SUMMARY OF THE INVENTION

The invention aims to solve the prior art problems by proposing contrast agents which have good biocompatibility, low toxicity and high sensitivity, which are effective at a low concentration, which have a high vascular remanence and, in addition, which have a real specificity (vectorization), in particular for the brain.

To this effect, the invention proposes contrast agents having a structure of the chelated complex of a marker-dendritic structure(s) type, each dendrite of the dendritic structure having a free end which can be functionalized.

The functionalization of the dendrites makes it possible to obtain vectorization of the contrast agent to a particular organ, and in particular the brain. The dendrite-functionalizing agent can also be chosen so as to increase the lipophilicity of the contrast agent, in particular to enable it to cross the blood-brain barrier. Another type of possible functionalization of the dendrites is functionalization with a therapeutic agent.

Yet another type of functionalization makes it possible to increase the vascular remanence of the contrast agent of the invention.

The dendrites of the dendritic structure can either all have the same functionalization or some of the dendrites can have a first type of functionalization and the other dendrites can have other types of functionalization, for example at least one dendrite of the dendritic structure is functionalized so as to increase the lipophilicity of the contrast agent and thus enable it to cross the blood-brain barrier, and at least one other dendrite of the dendritic structure can be functionalized so as to increase the specificity of the contrast agent to the brain.

This makes it possible to obtain novel contrast agents which enable not only the diagnosis of central nervous system pathologies, such as Alzheimer's disease and Parkinson's disease, but also an understanding of the mechanisms involved in these diseases.

However, in another embodiment, at least one dendrite of the contrast agent may be functionalized so as to obtain vectorization of the complex of the invention to the brain, at least one other dendrite of the dendritic structure may be functionalized so as to enable crossing of the blood-brain barrier, and yet at least one other dendrite of the dendritic structure may be functionalized with a therapeutic agent specific for central nervous system diseases, so as to act directly and specifically on the brain.

Each dendritic structure of the invention, also called dendron, is composed of an internal part, also called core of the dendritic structure, and of a periphery, which corresponds to the dendrites themselves.

As regards the chelating agent or chelating structure of the magnetic or scintigraphic marker, it may be modified so as to increase the in vivo stability of the contrast agents.

Each dendritic structure of the complex of the invention is nontoxic for a human organism, which means, in particular, that this dendritic structure cannot be a structure based on polyamide polymers or dendrimers.

The invention will be understood more clearly and other advantages and characteristics thereof will emerge more clearly on reading the explanatory description which follows.

DETAILED DESCRIPTION OF THE INVENTION

In a general embodiment, the invention concerns dendritic chelated complexes characterized in that they have the following general formula I:

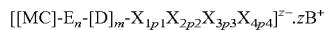

formula I in which:
M is a magnetic marker, preferably chosen from $Gd^{3+}$, $Mn^{2+}$ and $99mTc^{3+}$ ions,
C is a chelating agent for the magnetic marker M,
[MC] is a chelate of the magnetic marker M,
E is a spacer,
n=0 or 1,
[D] is a dendritic structure, the core of which comprises at least one group derived from benzyl alcohol or from a benzyl amine, the benzyl ring of which is substituted at positions 3, 4, 5 with dendrites composed of polyethylene glycol units,
m is an integer equal to 1 or 2 or 4,
$X_1$ is a group for increasing the lipophilicity of the complex, for example a tert-butyl (tBu) group,
p1 is an integer equal to 0 to 12, limits included,
$X_2$ is a group for increasing the specificity of the complex for a particular organ, preferably for the brain, such as L-dopamine,
p2 is an integer equal to 0, 1, 2 or 4, limits included,
$X_3$ is a group having a therapeutic activity, preferably for neurodegenerative diseases such as Alzheimer's disease, Parkinson's disease and multiple sclerosis,
p3 is an integer equal to 0, 1, 2 or 4, limits included,
$X_4$ is a $CH_3$ group,
p4 is an integer equal to 0 to 12, limits included,
p1+p2+p3+p4=3 when m=1 or p1+p2+p3+p4=6 when m=2 or p1+p2+p3+p4=12 when m=4,
B is a counterion, preferably $Na^+$ or $K^+$,
z is an integer equal to 0, 1, 2, 3 or 4.

Preferably, the chelating agent C is diethylenetriaminepentaacetic acid (DTPA), a catechol-derived tripod or an 8-hydroxyquinoline-derived tripod, which are excellent chelating agents for $Gd^{3+}$, $Mn^{2+}$ and $99mTc^{3+}$ ions.

Each dendritic structure, or dendron, of the complexes of the invention is of the Fréchet dendron type, as described in *Dendrimers and other dendritic polymers*, J. M. J Fréchet, D. A. Tomalia, Wiley, New York, 2001.

Fréchet dendrons have the following formulae, depending on which generation these dendrons belong to.

First-generation Fréchet dendron, i.e. comprising a single dendritic structure, the internal or core part of which is a group of the benzyl alcohol type, the benzyl ring being substituted at positions 3, 4, 5 with polyether chains constituting the dendrites.

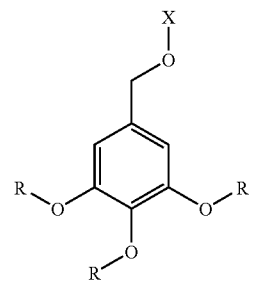

In the complexes of the invention, and with reference to the above formula, O—R is a chain composed of ethylene glycol units ($-OCH_2CH_2$) and X represents the chelate, denoted [MC] in formula I;

second-generation Fréchet dendron, i.e. comprising two dendritic structures identical to the first-generation Fréchet dendrons described above.

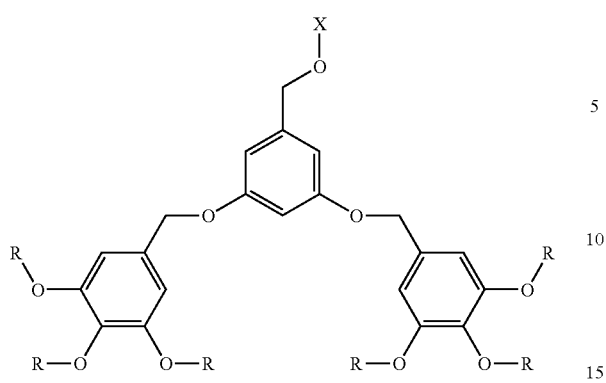

In the complexes of the invention, and with reference to the above formula, the O—R chains are composed of ethylene glycol units and X represents the chelate, denoted [MC] in formula I;

third-generation Fréchet dendron, i.e. comprising four dendritic structures identical to the first-generation Fréchet dendron above, linked in pairs so as to form two structures identical to the second-generation Fréchet dendron above.

Each of the structures identical to the second-generation Fréchet dendrons are linked, respectively, at positions 3 and 5 of a ring of benzyl alcohol type.

ylene glycol chain, denoted E in formula I, i.e. when n=1 in formula I, the dendritic structures of the invention have the following formulae, depending on the generation thereof.

It will be noted that, in this case, the benzyl ring linked to the spacer is no longer a ring derived from a benzyl alcohol, but a ring derived from a benzyl amine.

First-generation dendron used when the dendritic structure is linked to the chelate [MC] by means of the spacer E:

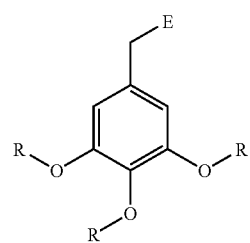

In this formula, E represents the spacer and O—R represents dendrites composed of ethylene glycol units.

Second-generation dendritic structures when the dendritic structures are linked to the chelate [MC] by means of a spacer E.

In this case, the benzyl ring linked to the spacer is of the benzyl amine type. The dendritic structures then have the dendritic structure corresponding to the formula below:

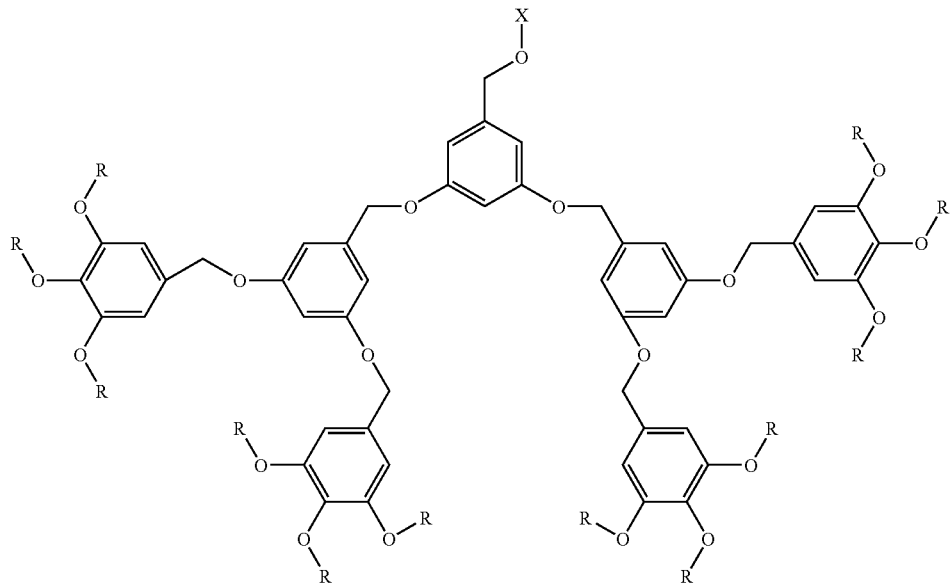

As for the first- and second-generation Fréchet dendrons, the polyether chains denoted O—R in the above formula are, in the complexes of the invention, composed of ethylene glycol units, and X represents the chelate, denoted [MC] in formula I.

The Fréchet dendrons described above are used when the dendritic structures are linked directly to the structure [MC], i.e. when n=0 in formula I or when the dendritic structures are linked to the chelate [MC] via a spacer of polyethylene glycol type.

The preferred spacers used in the invention are described hereinafter.

When the dendritic structures are not linked directly to the chelate [MC], but by means of a spacer other than a polyeth-

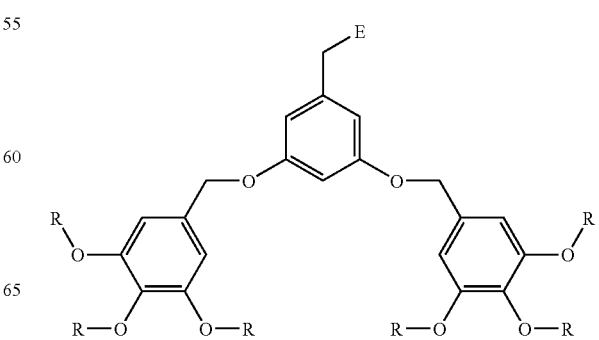

As in the previous cases, E represents the spacer and the dendrites denoted O—R are chains composed of ethylene glycol units.

Third-generation dendritic structures when they are linked to the chelate [MC] by means of a spacer;

Here again, the benzyl ring linked to the spacer is a ring of the benzyl amine type. The third-generation dendritic structures have the following formula:

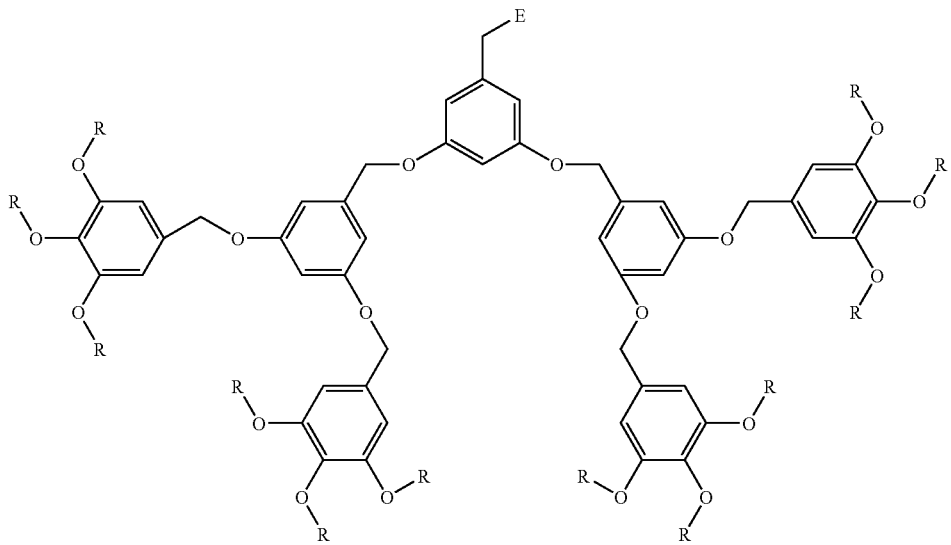

In this formula, E represents the desired spacer and the O—R chains are composed of ethylene glycol units.

The nontoxicity of polyethylene glycol, in vivo, has for a long time been demonstrated.

Preferably, the dendrites of the complexes of the invention comprise 3, more preferably 4, ethylene glycol units.

The dendritic structures of the complexes of the invention are linked, via their free end at position 1 of the benzyl alcohol or benzyl amine ring, to the chelate of the magnetic marker, denoted [MC] in formula I, either directly or by means of a spacer denoted E in formula I.

A spacer may advantageously be used when the chelating agent is a catechol-derived tripod or an 8-hydroxyquinoline-derived tripod, but is not recommended when the chelating agent is DTPA.

This is because, when the chelating agent is DTPA, the monopolization of one of the branches of the DTPA in order to graft the dendron(s) destabilizes the complex formed, and it is necessary to overcome this loss of stability by maintaining the voluminous globular structure of the dendrons close to the chelate.

However, when the chelating agent is a catechol-derived tripod or an 8-hydroxyquinoline-derived tripod, the complexes formed are sufficiently stable that they do not need the protective effect of the voluminous globular structure of the dendrons, and the presence of a spacer E between this dendron structure and the chelate makes it possible to sufficiently distance these two structures from one another so as to avoid the problems of steric hindrance that might occur.

Furthermore, the spacer will make it possible to modify the biodistribution of the complexes of the invention in the body, by promoting, in the end, a greater distribution to the brain.

Thus, the spacer E may be a cationic or anionic or even neutral compound.

The neutral spacers used in the invention are spacers of the diamine type, of formula

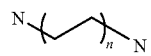

with n preferably equal to 1 or 2, i.e. the preferred spacers are ethylenediamine and butanediamine spacers.

Other preferred neutral spacers are spacers of the ethylene glycol, preferably tri- or tetraethylene glycol, type:

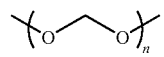

The cationic spacers used in the invention are compounds of the type of an aromatic ammonium or an ammonium comprising a branched aliphatic chain.

The cationic spacers of the type of an aromatic ammonium are composed of the following units:

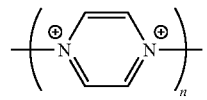

Preferably, n=1 or 2.

The cationic spacers of the type of an aliphatic ammonium comprising a branched chain, used in the invention, have the following formula:

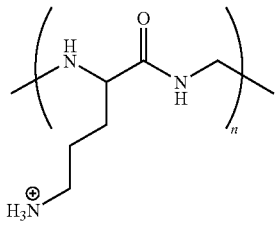

Preferably, in this formula, n=1 or 2.

The anionic spacers used in the invention have the following formula:

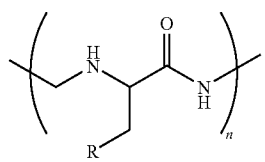

In this formula, n is preferably 1 or 2.

According to the groups present at the ends of the dendrites of the complexes of the invention, various properties are obtained. This is what is called the functionalization of the dendrites.

Thus, in a first embodiment of the invention, the dendritic chelated complex of general formula I is a complex in which the chelating agent C is DTPA, and the dendrites are functionalized with methyl groups, denoted $X_4$ in formula I.

An example of a complex according to the first embodiment of the invention is the compound of formula II-1 below:

Formula II-1

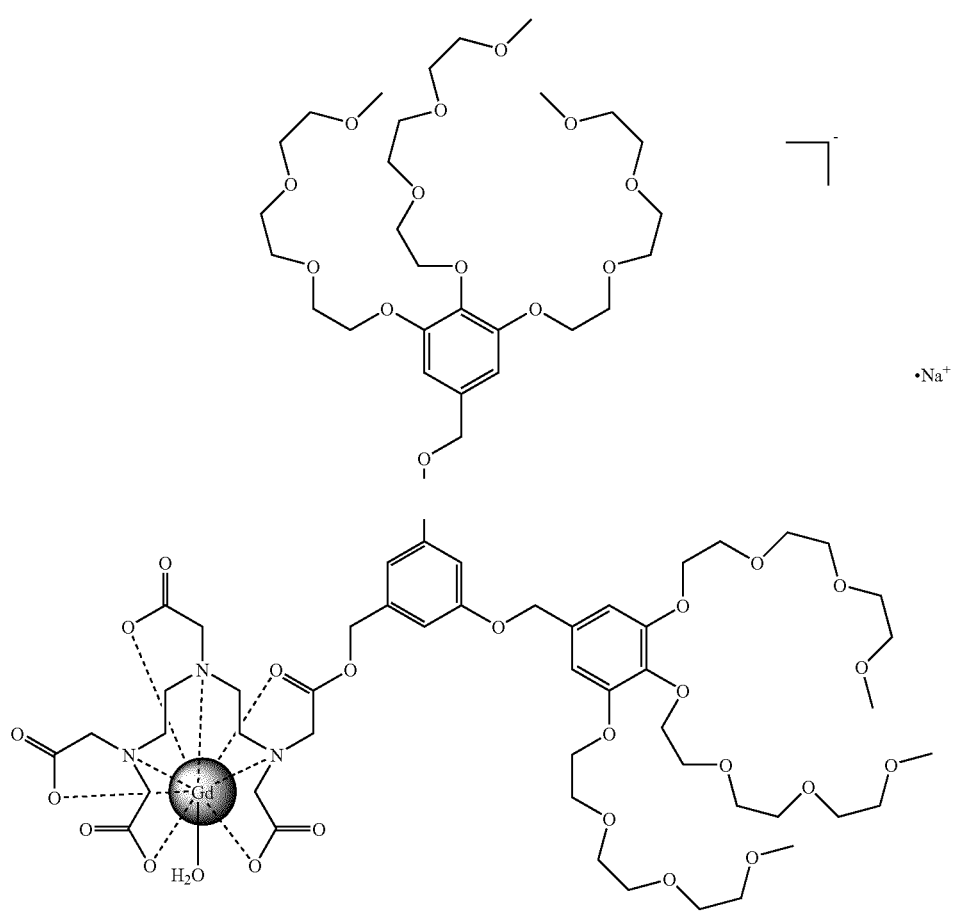

•Na⁺

The complex of formula II-1 above was tested in MRI imaging on healthy mice, and it was noted that it exhibits no detectable toxicity at a dose of 0.5 mmol per kg.

In fact, in vivo, free gadolinium, which has the same ionic radius as calcium, competes with calcium-dependent systems and blocks the reticuloendothelial system, thereby having an influence on myocardial contractability, coagulation, calcium-dependent enzymes, mitochondrial respiration and neurotransmission. This can manifest itself by a drop in blood pressure followed by cardiovascular arrest and pulmonary paralysis.

However, with the complexes of the invention, the thermodynamic stability of DTPA complexes is sufficient to prevent the release of toxic amounts of $Gd^{3+}$. This has been verified on neuronal cells, involving the level of lactate dehydrogenase (LDH). For concentrations ranging between 1 and 10 000 μM, it was noted that the level of LDH and also the proliferation of the neural cells were identical with the complex of formula II-1 according to the invention and the commercially available product consisting only of the $Gd^{3+}$ chelate in which the chelating agent is DTPA.

The studies carried out on this compound have shown that the product is incapable of crossing the blood-brain barrier (BBB), but, on the other hand, they have demonstrated a high vascular remanence: the contrast agent remains stable and in circulation in the blood for at least 72 h, thereby enabling long and consequently more complete examinations, without the risk of toxicity, which is an advantage over the commercially available product of the prior art.

The dendritic chelated complex of the invention which has formula II-2 below, in which the magnetic marker is $Mn^{2+}$, has the same advantages, which is considerable progress in the field of magnetic imaging with $Mn^{2+}$, called MEMRI (Manganese Enhanced Magnetic Resonance Imaging).

In fact, the $Mn^{2+}$ marker makes it possible to obtain a much higher contrast than the $Gd^{3+}$ marker, but in its $MnCl_2$ form currently used in animal experiments, it is very toxic, since $Mn^{2+}$ is a neurotoxin at high concentrations.

Furthermore, the manganese complexes are relatively unstable in vivo and are dissociated in a biological medium.

However, with the dendritic chelated complexes of the invention, the contrast agent with the $Mn^{2+}$ marker is very stable, diffuses slowly and is therefore nontoxic.

Specifically, toxicity studies carried out on live healthy mice have shown that the complex is no more toxic than the complex of formula II-1 above, in which the marker is $Gd^{3+}$.

These products, the dendrites of which are terminated with $CH_3$ groups, not only remain in the organism for three days, but remain stable for these three days. It is this stability which explains the nontoxicity of these products. This is because, since they are stable, they do not rapidly release the magnetic marker into the organism and are eliminated by the organism while the marker is still in chelate form.

The same advantages, in terms of toxicity, are found in nuclear medicine with the dendritic chelated complex having formula II-3 below, where the scintigraphic marker is $99mTc^{3+}$.

They are also found in terms of stability, but limited, of course, to the half-life of $99mTc^{3+}$, which is 6 and a half hours.

Formula II-2

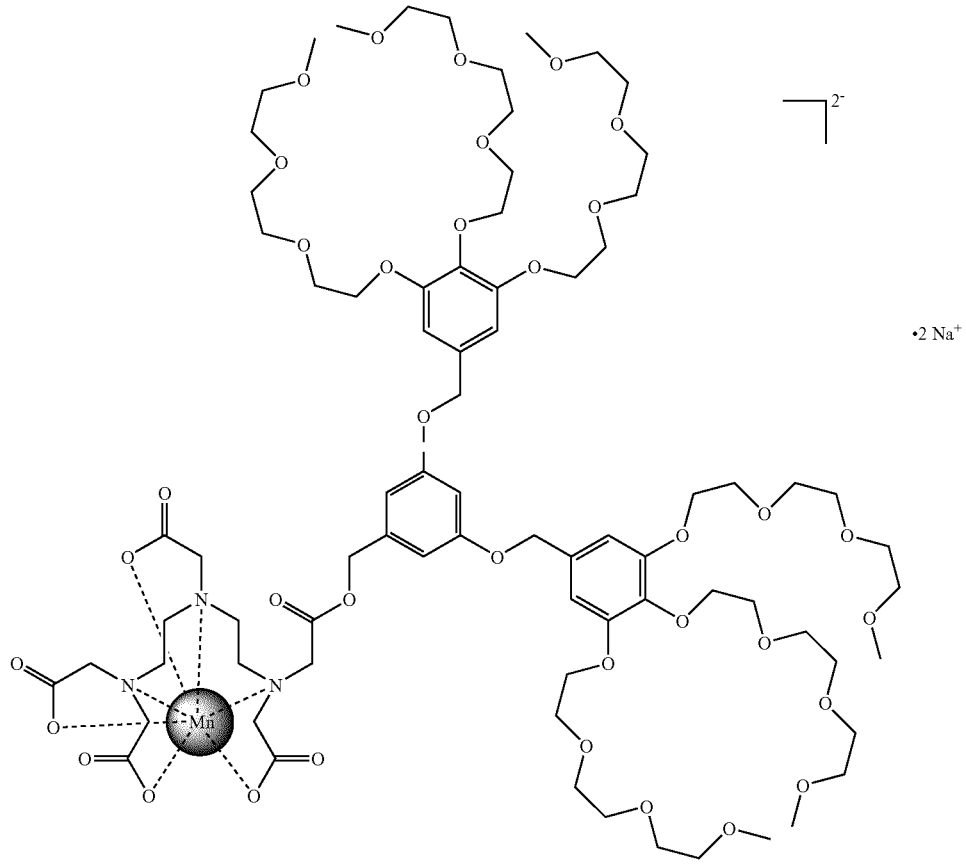

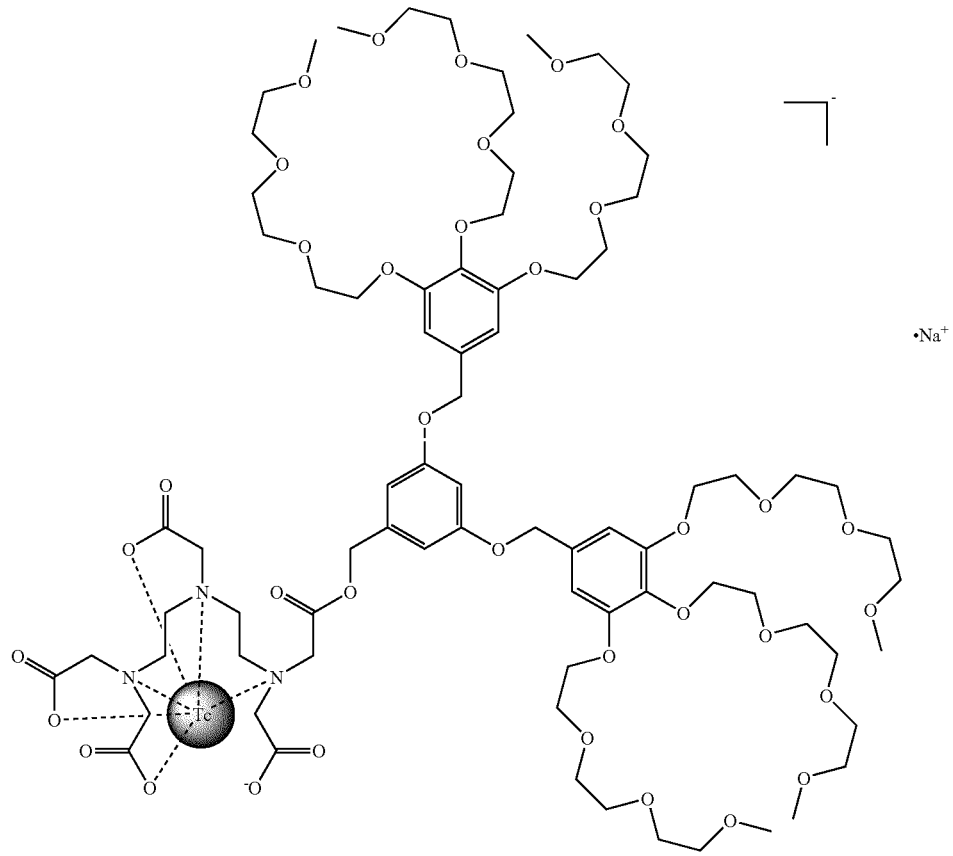

Formula II-3

The complexes corresponding to those of formulae II-1 to II-3 above, but which are first-generation and third-generation, and also those in which the dendrites are tetraethylene glycol chains and no longer triethylene glycol chains, have the same advantages.

In all these complexes, the magnetic marker is bonded to the DTPA via coordination bonds.

For example, for $Gd^{3+}$, the DTPA-$Gd^{3+}$ chelate bonds in the following way:

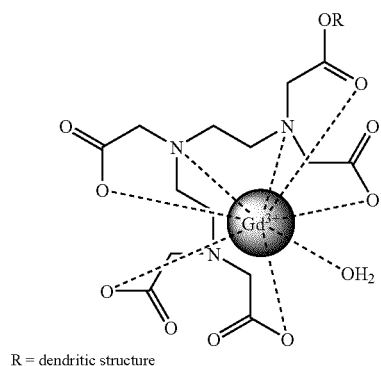

R = dendritic structure

In order to increase the stability of the complexes of the invention, in a second embodiment of the invention, the chelate of the magnetic or scintigraphic marker is a catechol-derived tripod, and no longer DTPA.

In this case, the preferred complexes of the invention are the complexes of formula III-1 to III-3 below.

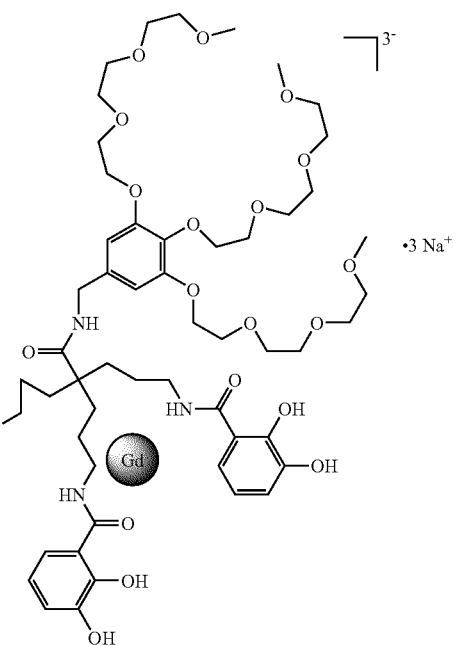

Formula III-1

-continued

Formula III-2

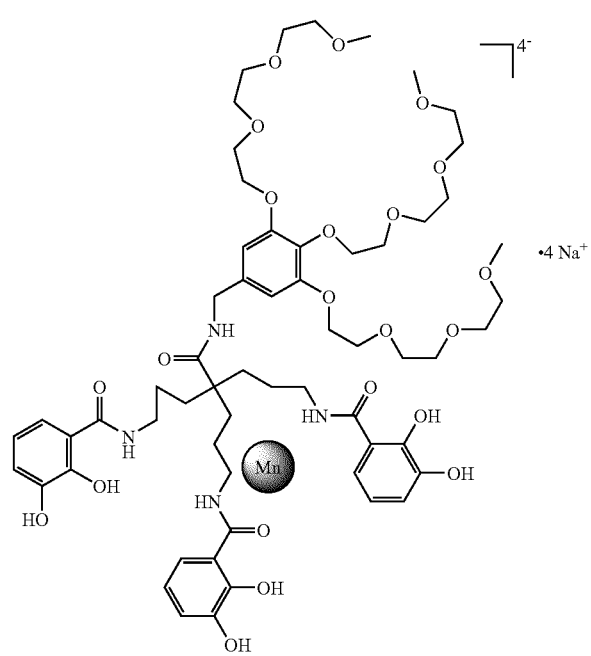

Formula III-3

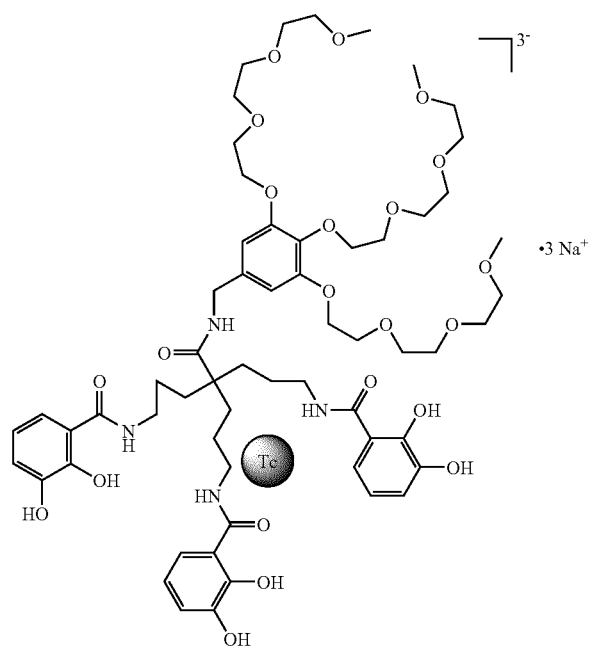

In these formulae, and with reference to general formula I, each dendrite of the dendritic structure [D] is a methylated polyethylene glycol chain comprising 3 ethylene glycol units, m=1, the chelating agent C is a catechol-derived tripod, n=p1=p2=p3=0, B is Na$^+$ and z=3 or 4.

In formula III-1, the marker is Gd$^{3+}$, in formula III-2, the marker is Mn$^{2+}$ and in formula III-3, the marker is 99mTc$^{3+}$.

Other preferred complexes, according to the second embodiment of the invention, having an increased stability, have the following formulae IV-1 to IV-3:

Formula IV-1

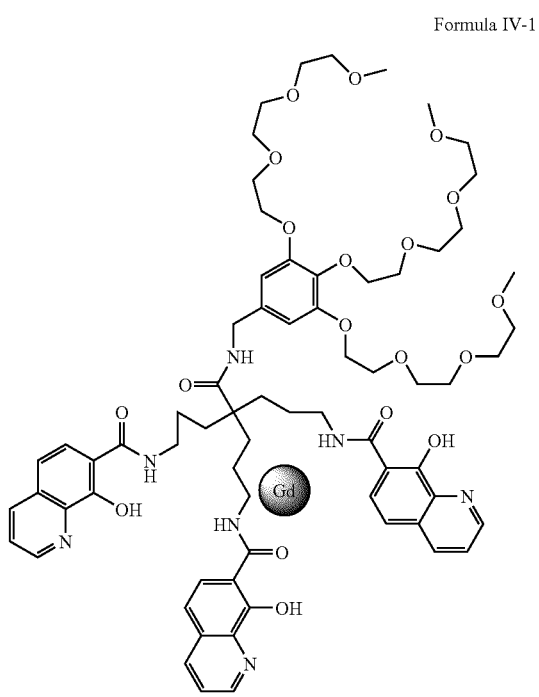

Formula IV-2

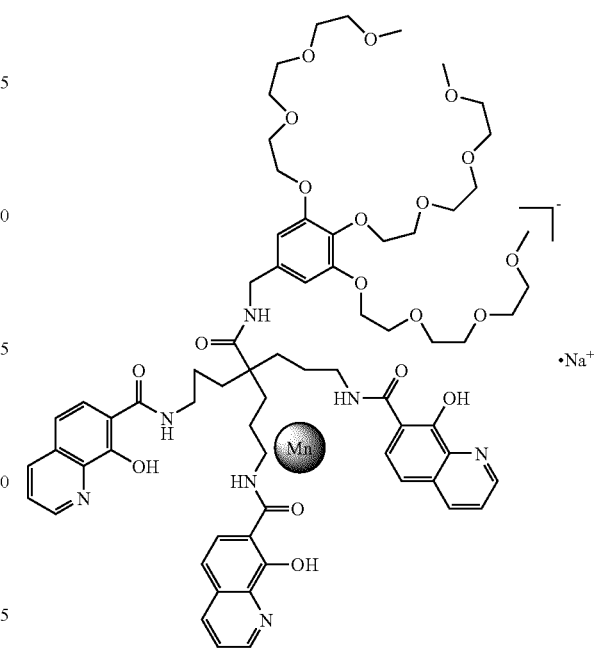

-continued

Formula IV-3

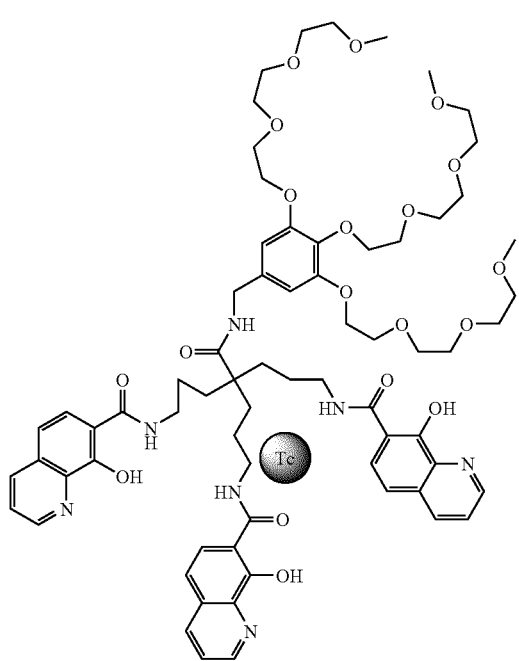

In these formulae, and with reference to general formula I, each dendrite of the dendritic structure [D] is a methylated polyethylene glycol chain having 3 ethylene glycol units, m=1, C is an 8-hydroxyquinoline-derived tripod, p1=p2=p3=0, B is $Na^+$ and z=0 or 1.

In formula IV-1, the marker is $Gd^{3+}$, in formula IV-2, the marker is $Mn^{2+}$ and in formula IV-3, the marker is $99mTc^{3+}$.

However, other preferred complexes according to the second embodiment of the invention, having an increased stability, are complexes having a dendritic structure of generation G2, i.e. in which each dendrite of the dendritic structure [D] is a methylated polyethylene glycol chain having 3 ethylene glycol units, m=2, C is a catechol-derived tripod, p1=p2=p3=0, and B is $Na^+$.

When the marker is $Gd^{3+}$, z=3 and the complex has the following formula V-1:

Formula V-1

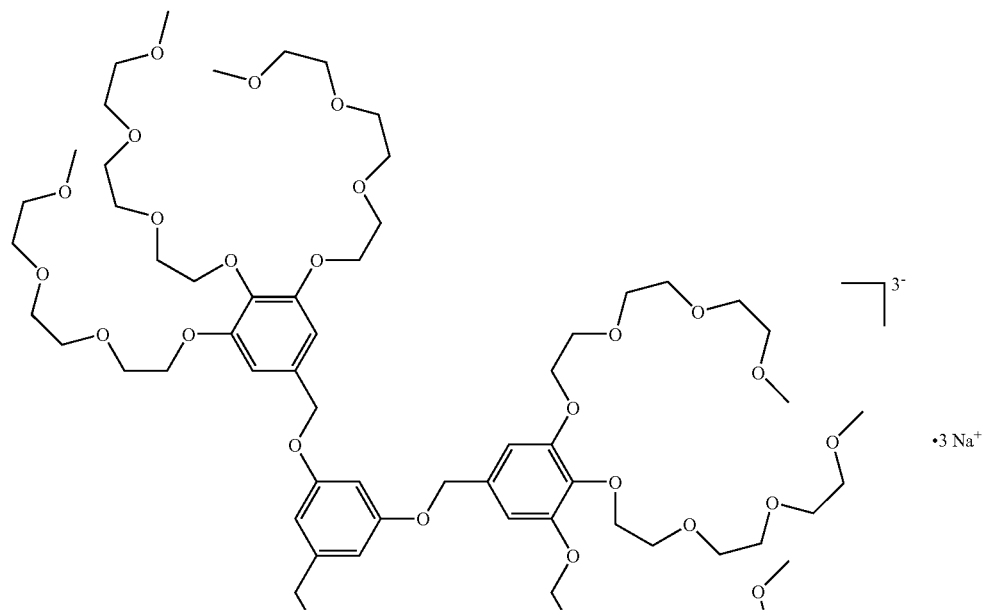

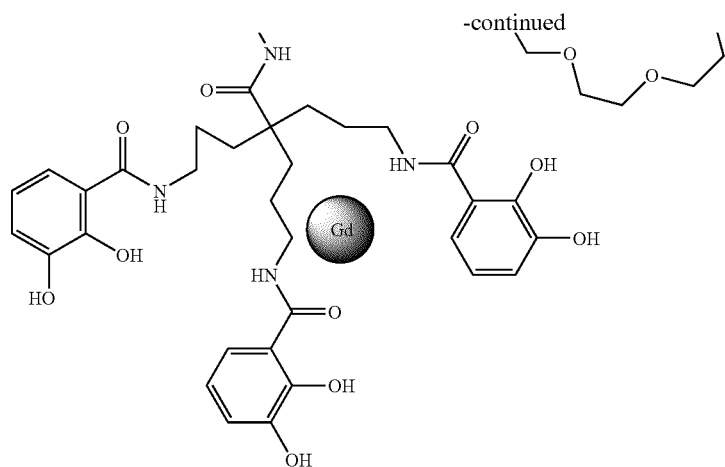
When the marker is $Mn^{2+}$, $z=4$ and the complex has the following formula V-2:
Formula V-2
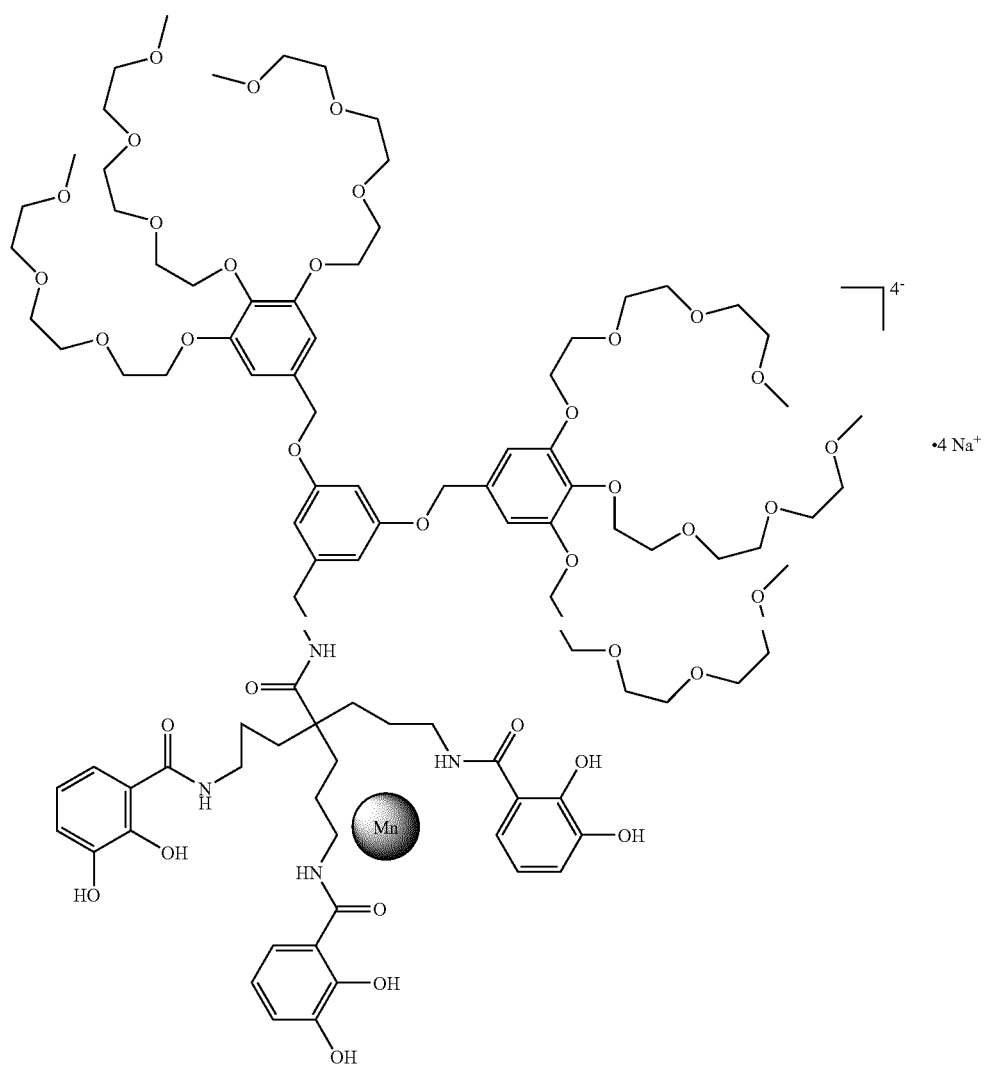

When the marker is 99mTc$^{3+}$, z=3 and the complex has the following formula V-3:

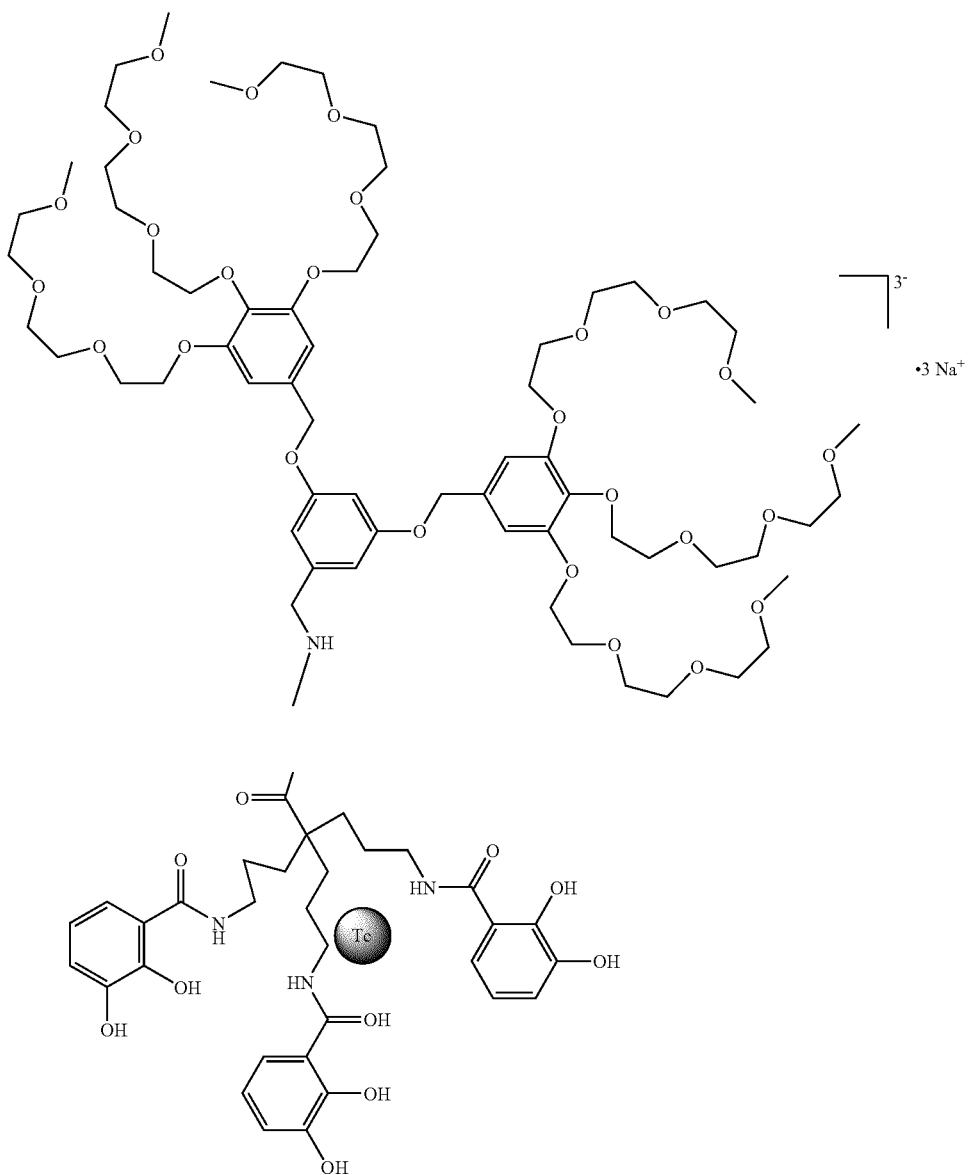

Formula V-3

The third-generation complexes, and also the first-, second- or third-generation complexes in which the dendrites are methylated tetraethylene glycol chains, and which correspond to these complexes in which the chelating agent is a catechol-derived tripod or an 8-hydroxyquinoline-derived tripod, are also preferred compounds of the invention.

However, the corresponding complexes in which the chelating structure is a catechol-derived tripod but in which the chelate is distanced from the structure formed by the dendrons, which are first- or second- or third-generation, via a spacer, denoted E in formula I, and which is one of the spacers described above, are most particularly preferred since they are distributed to the brain to a greater extent.

The compounds having the following formulae III-4 to V-6 are most particularly preferred:

23
Formula III-4
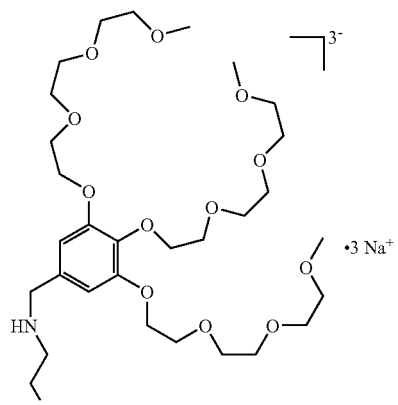
24
Formula III-5
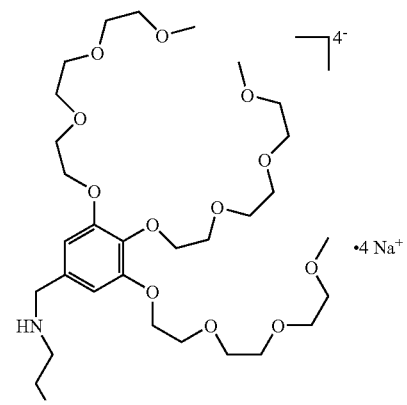
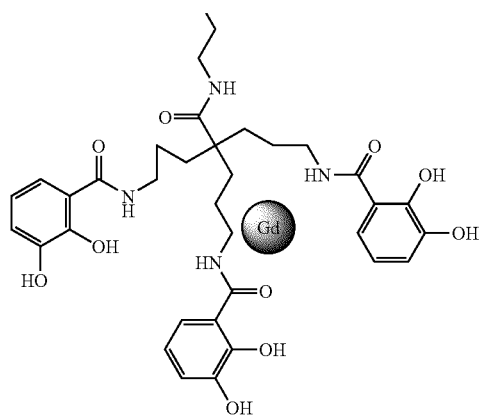
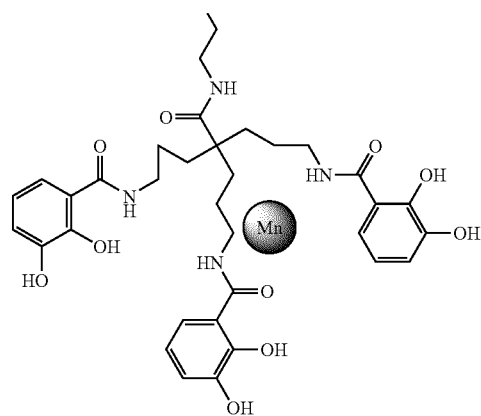
Formula III-6
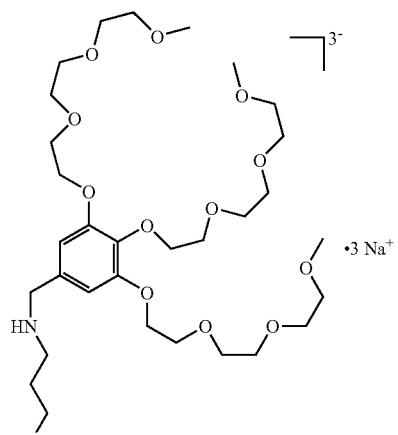
Formula IV-4
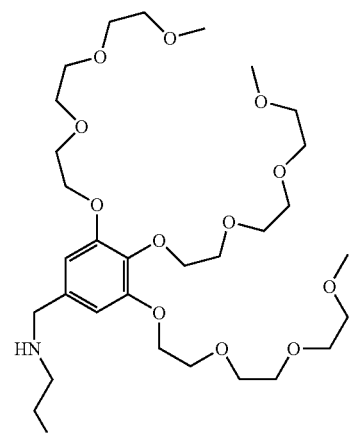

-continued
25
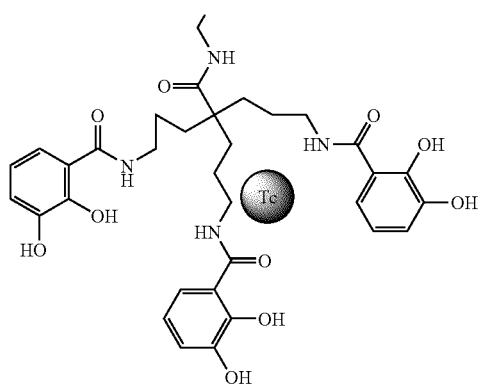
26
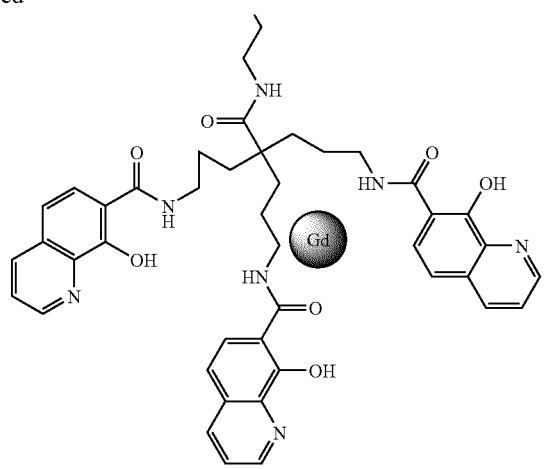
Formula IV-5
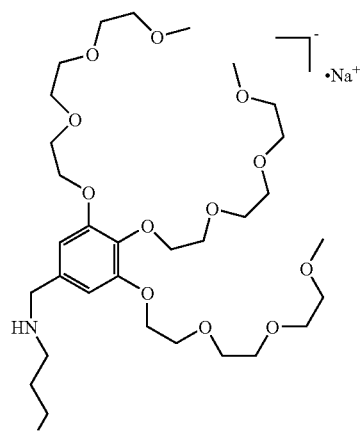
Formula IV-6
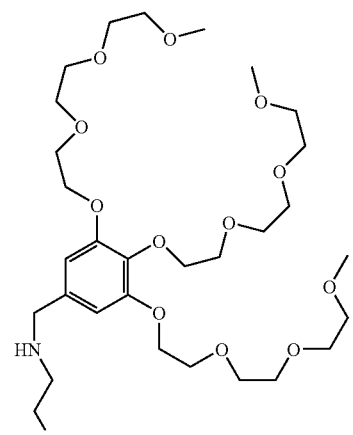
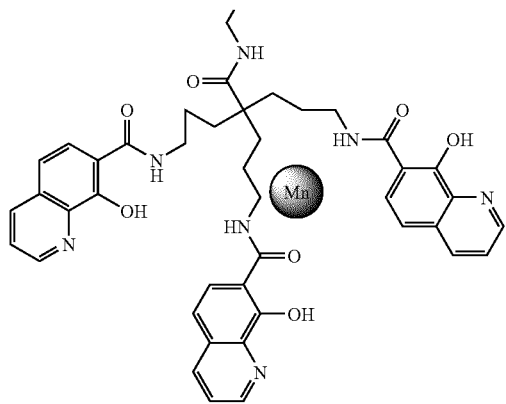
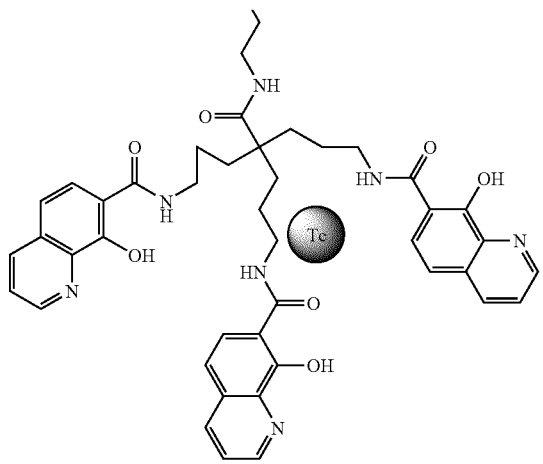

Formula V-4
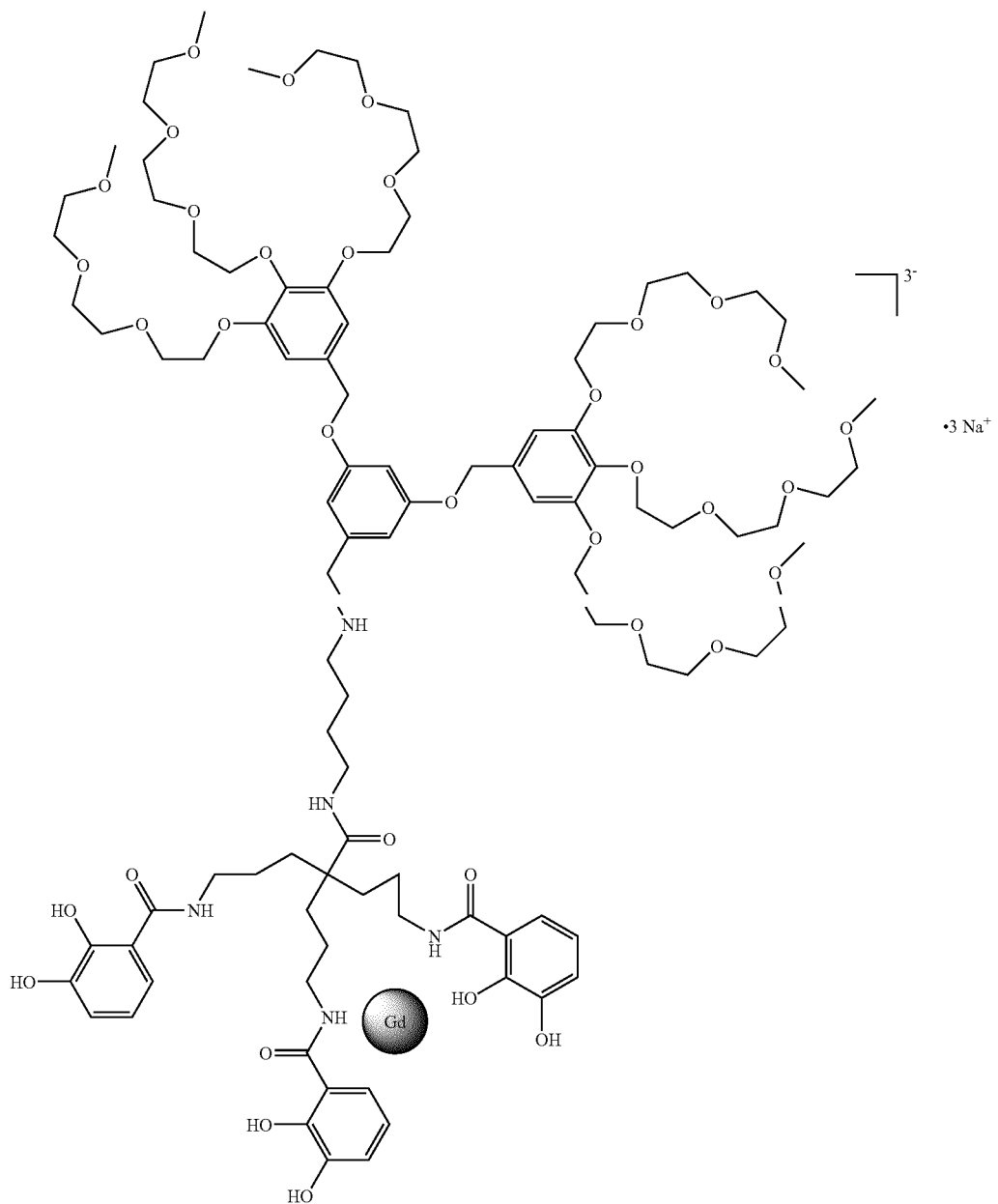

Formula V-5
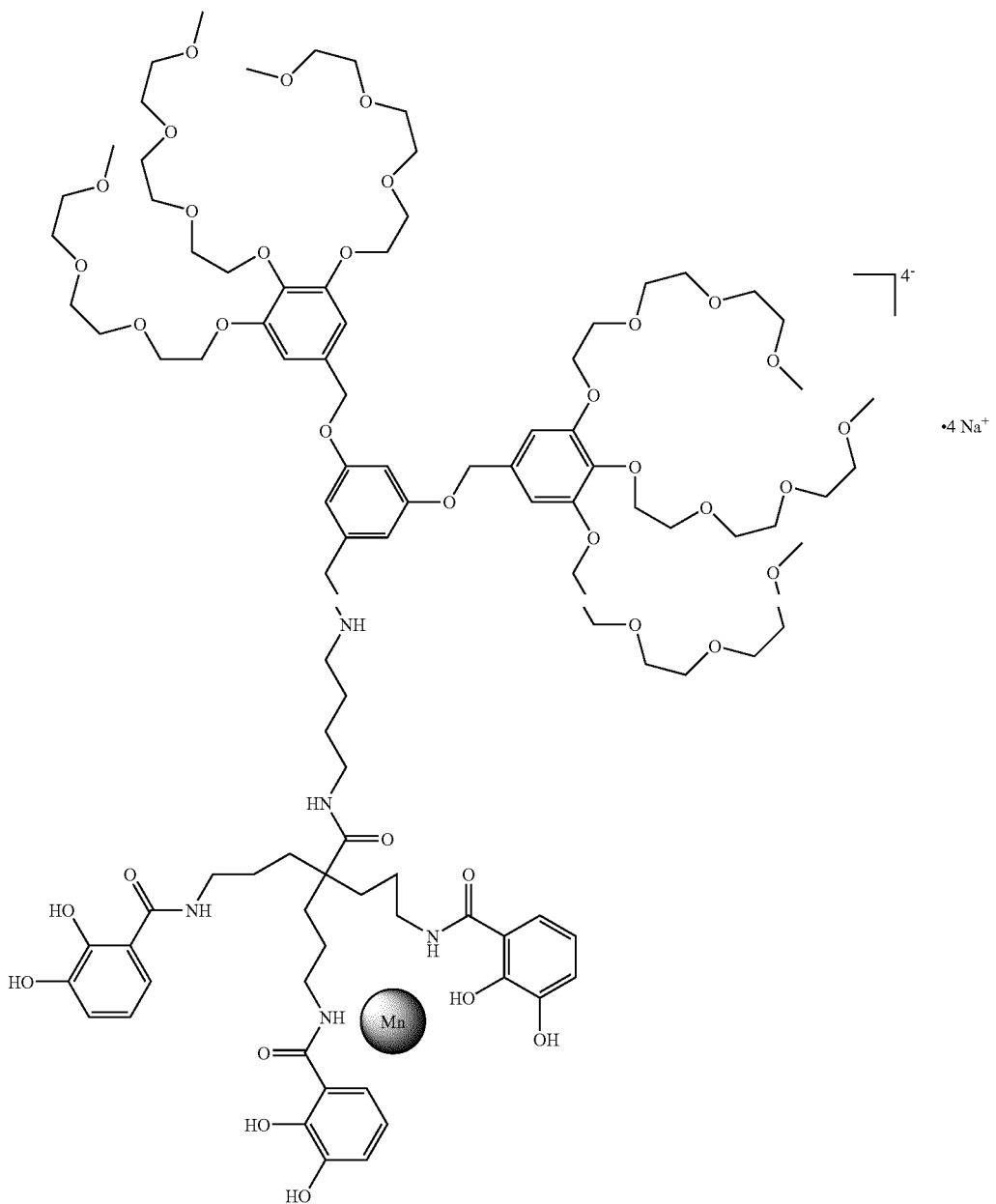

-continued
Formula V-6
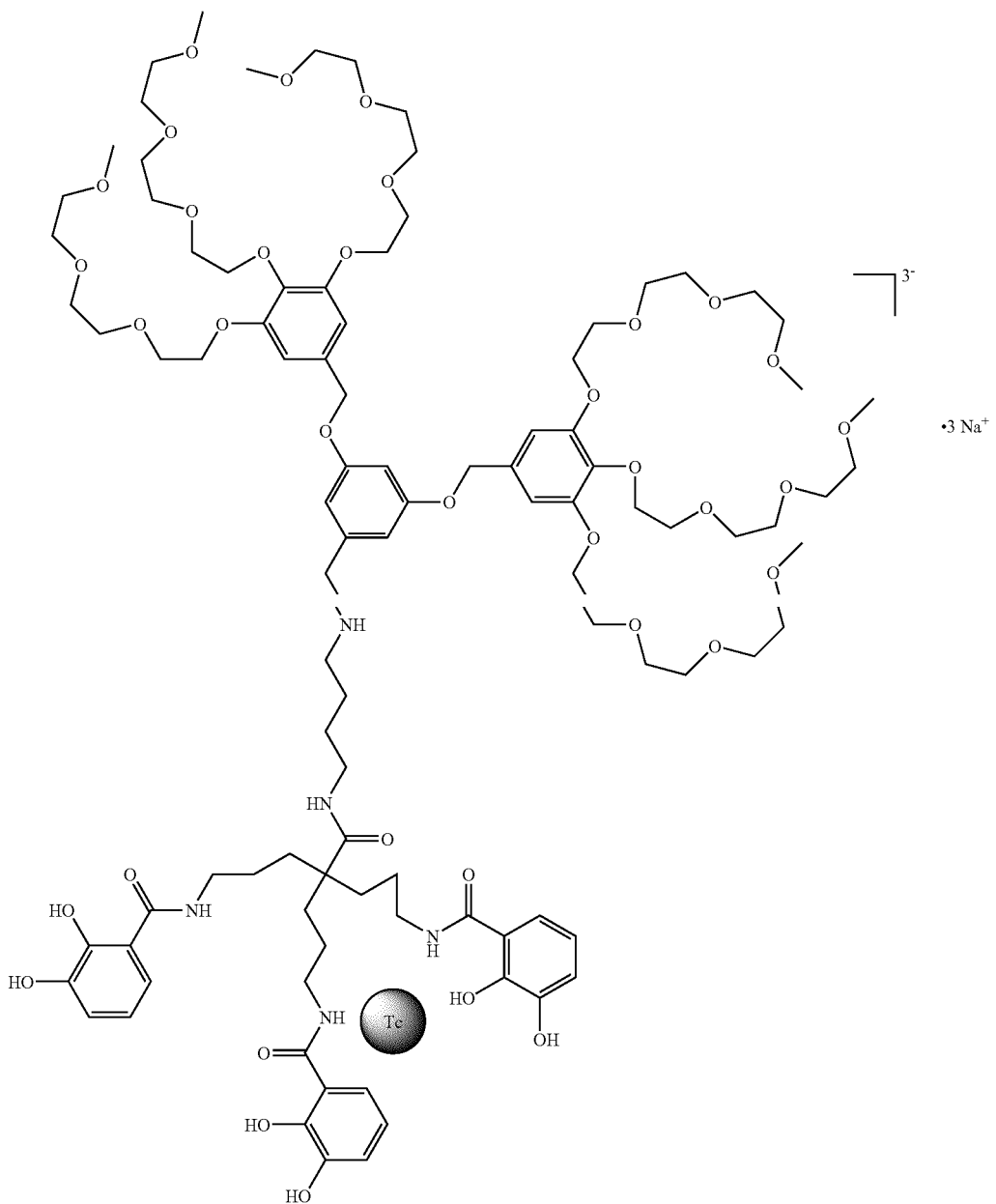

Thus, the third-generation complexes having the following formula, in which O—R represents an ethylene glycol chain comprising 3 or 4 ethylene glycol units

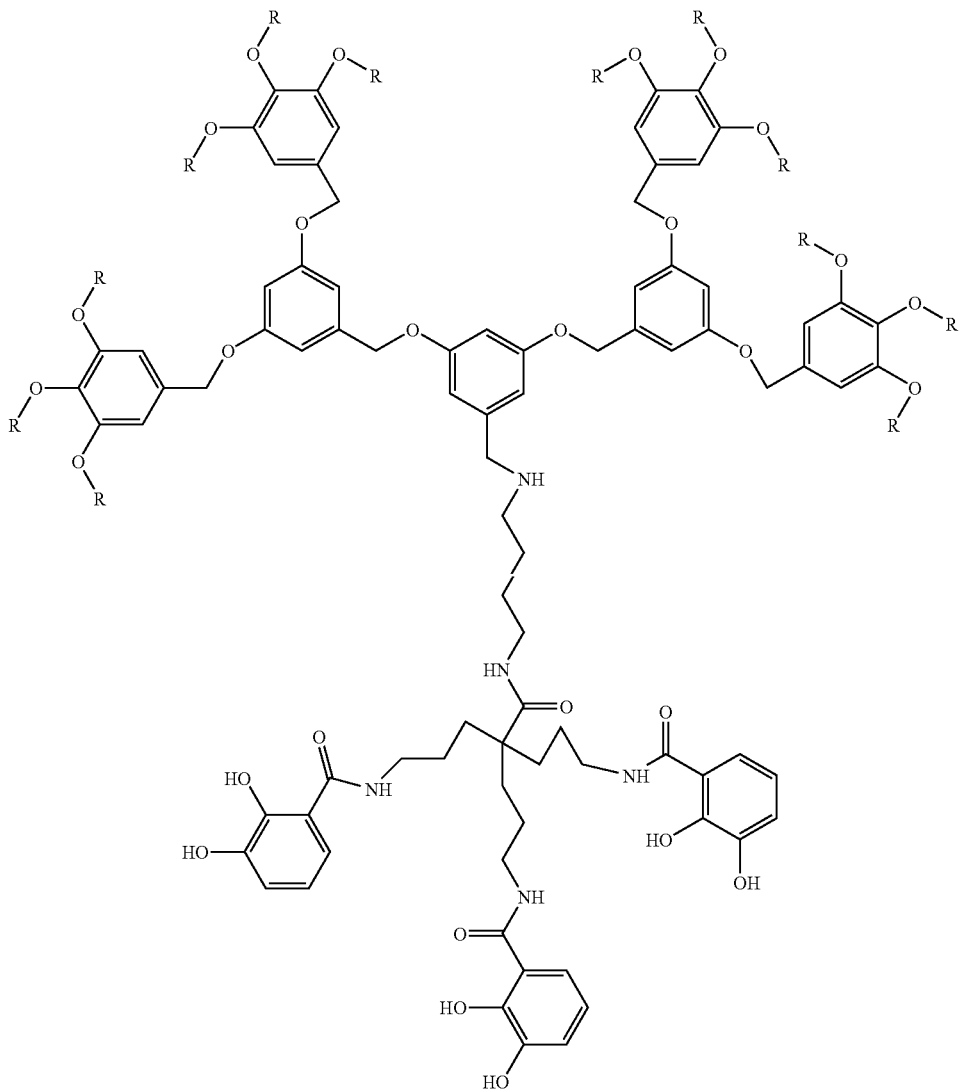

are particularly preferred.

The corresponding first- and second-generation complexes, and also the corresponding first-, second- or third-generation complexes in which the spacer is one of those described above, are also all particularly preferred.

In fact, the effectiveness of magnetic or scintigraphic contrast agents depends mainly on the stability of the complex formed, since an in-vivo distribution of the tracer (destruction of the complex, radioelement taken up, by a protein) induces nonselective irradiation of the cells, causing irreversible damage. It is therefore important for the complexes used to have excellent in-vivo stability.

Now, the insertion of aromatic rings into the chelation sphere provides better rigidity of the structure and thus enables pre-organization of the ligand.

It has been verified, by means of comparative kinetic monitoring between a complex of formula V-6 according to the invention, in which the chelating agent is a catechol-derived tripod and M is 99mTc$^{3+}$ and the corresponding complex of formula II-3 in which the chelating agent is DTPA, both grafted with a water-soluble dendrimer having a methylated ending, that the complex in which the chelating agent is a catechol-derived tripod is more stable.

In fact, more than 80% of the complex of formula V-6 is stable after 90 minutes, whereas 50% of the complex of formula II-3 is dissociated in the same period of time.

However, other preferred complexes according to the invention are complexes in which the chelating agent C is an 8-hydroxyquinoline-derived tripod, and which are first-, second- or third-generation, with or without spacer, and dendrites comprising 3 or 4 ethylene glycol units.

Thus, in these complexes of the invention, with increased stability and which are also preferred, and with reference to general formula I, each dendrite of the dendritic structure [D] is a methylated polyethylene glycol chain having 3 ethylene glycol units, m=2, C is an 8-hydroxyquinoline-derived tripod, p1=p2=p3=0, and the counterion B is Na$^+$.

When the marker M is Gd³⁺, z=0 and the complex has the following formula VI-1:
Formula VI-1
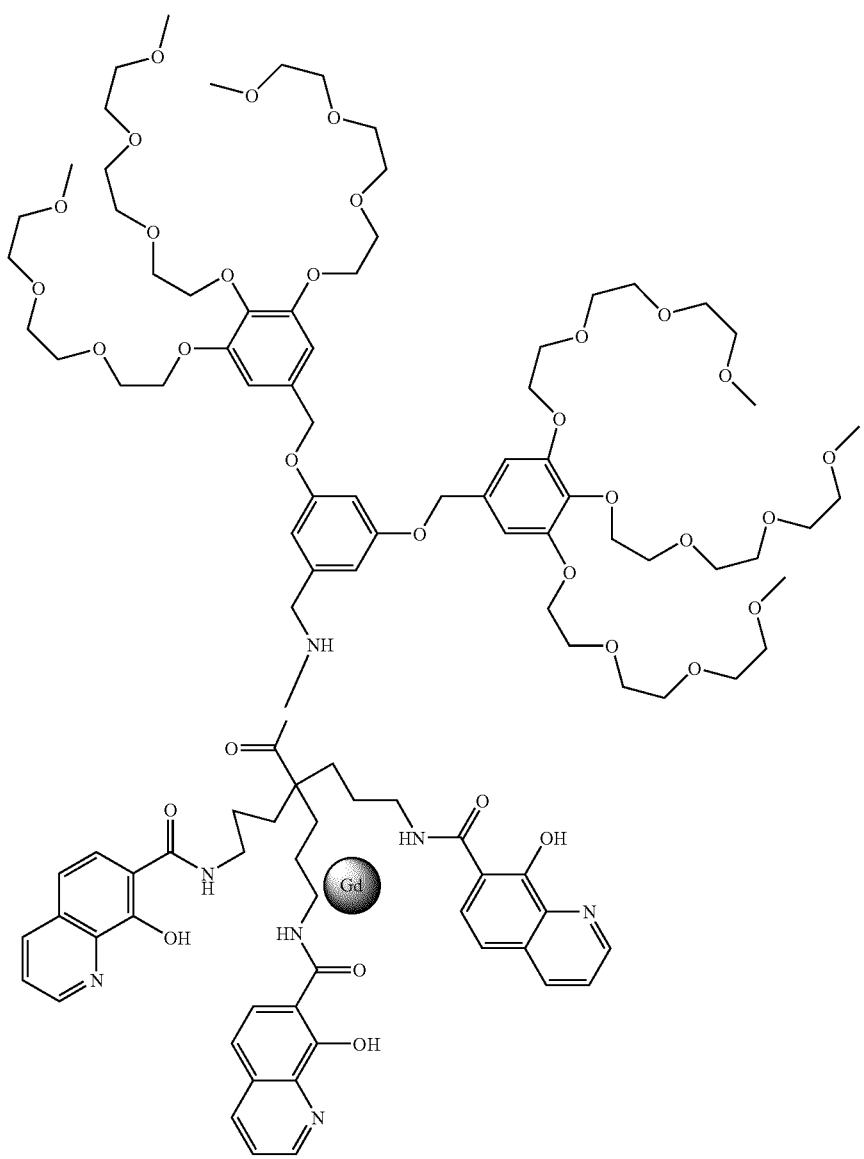

When the marker M is $Mn^{2+}$, z=1 and the complex has formula VI-2 below:
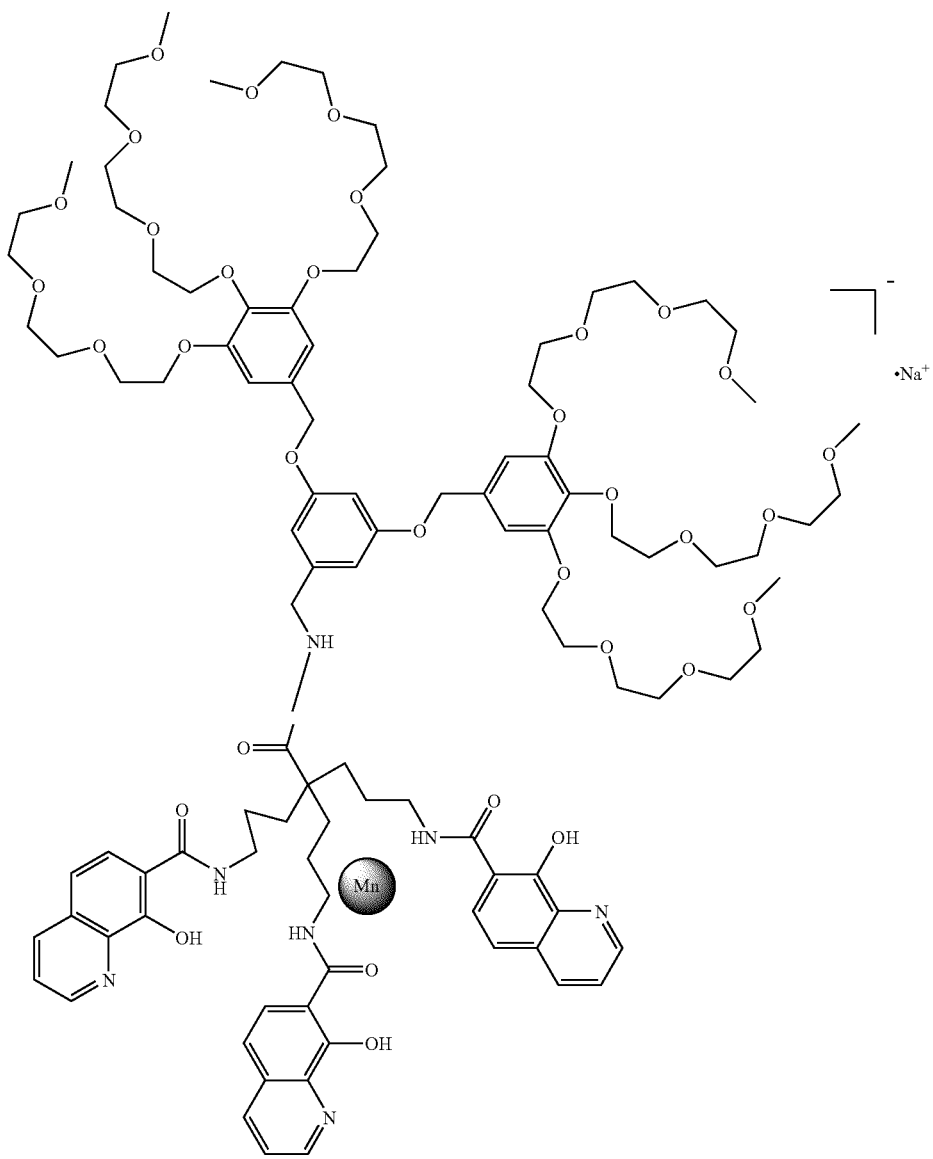
Formula VI-2

When the marker M is 99mTc$^{3+}$, z=0 and the complex has formula VI-3 below:

Formula VI-3

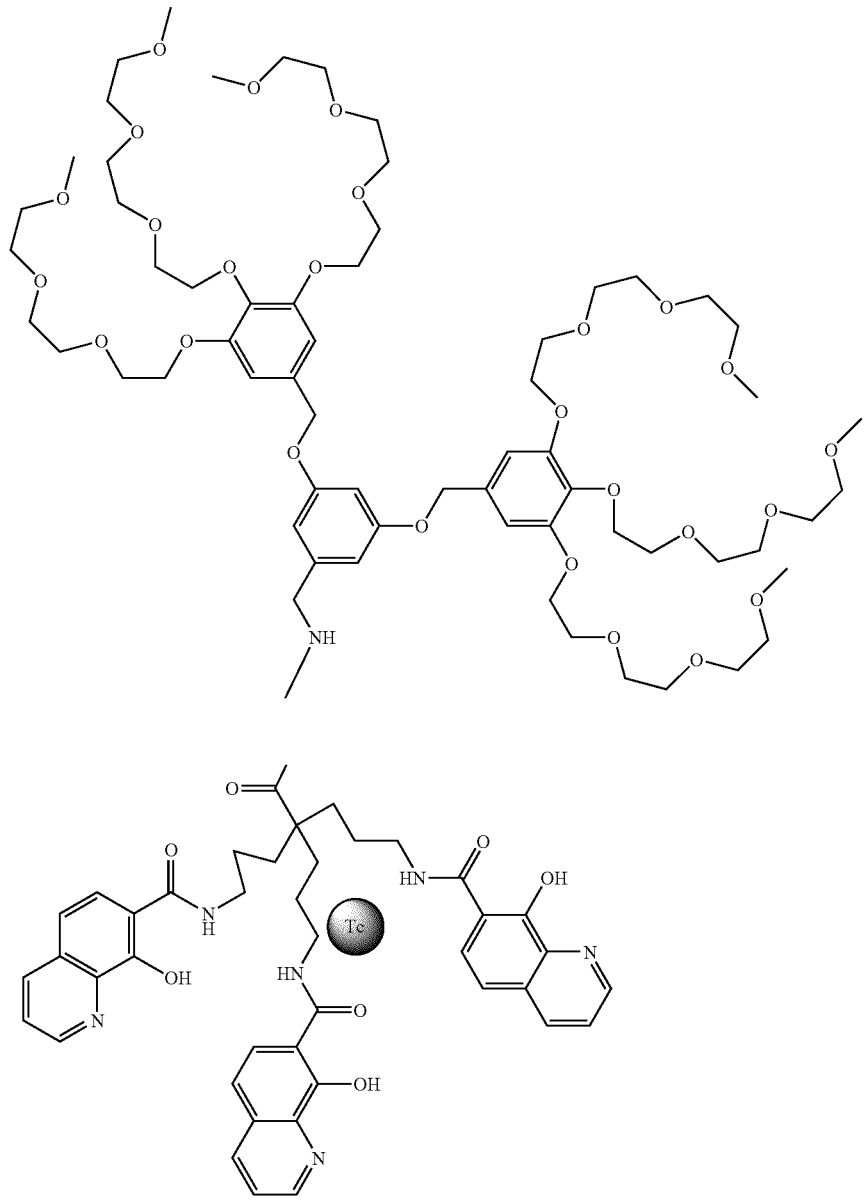

The complexes corresponding to the complexes of formulae VI-1 to VI-3 described above, of first generation or of third generation, and those of first or second or third generation comprising a spacer and/or the dendrites of which are tetra-ethylene glycols, are also preferred compounds of the invention.

For example, the second-generation complexes comprising a butanediamine spacer, corresponding to the complexes of formulae VI-1 to VI-3 above, have the following formulae VI-4 to VI-6:

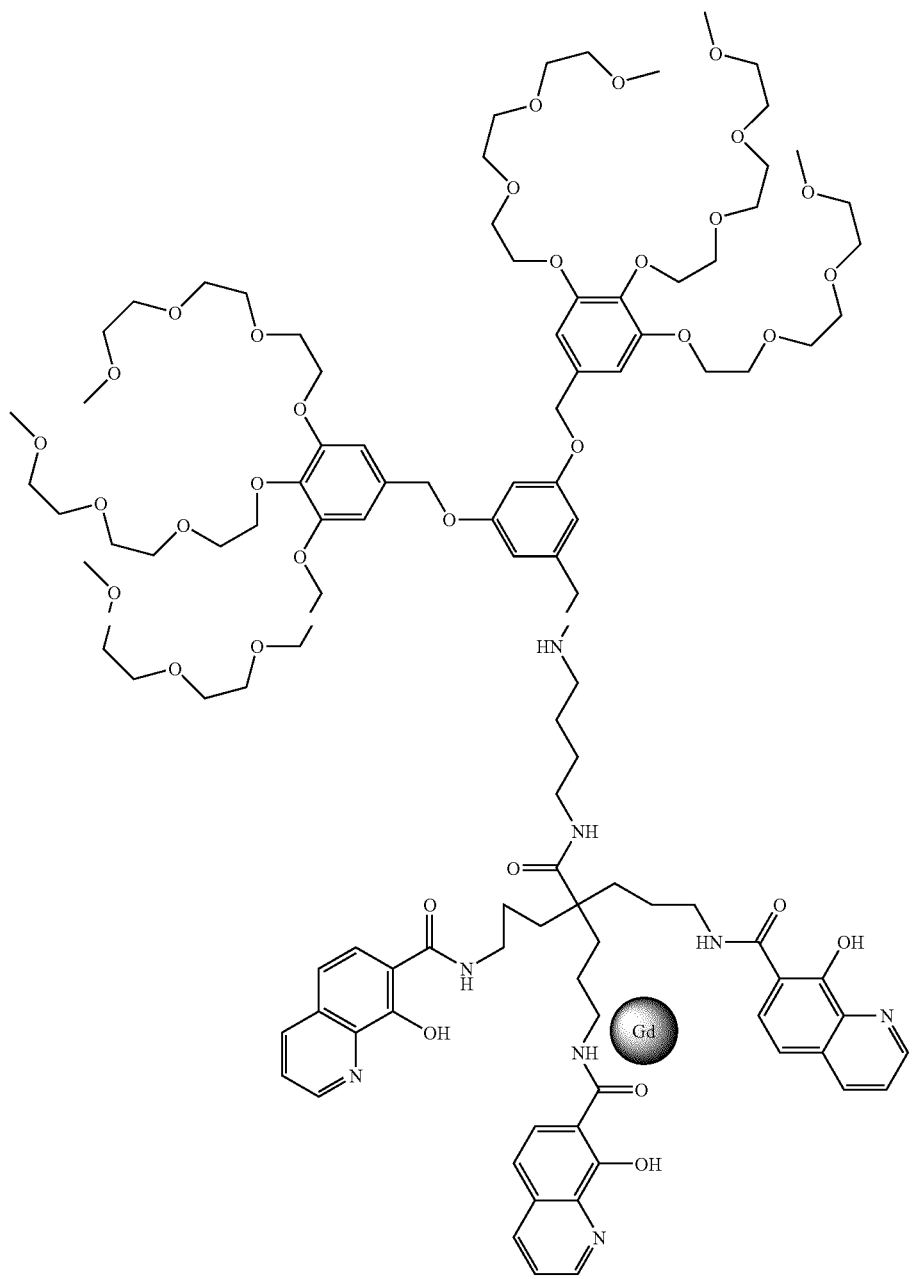
Formula VI-4

-continued
Formula VI-5
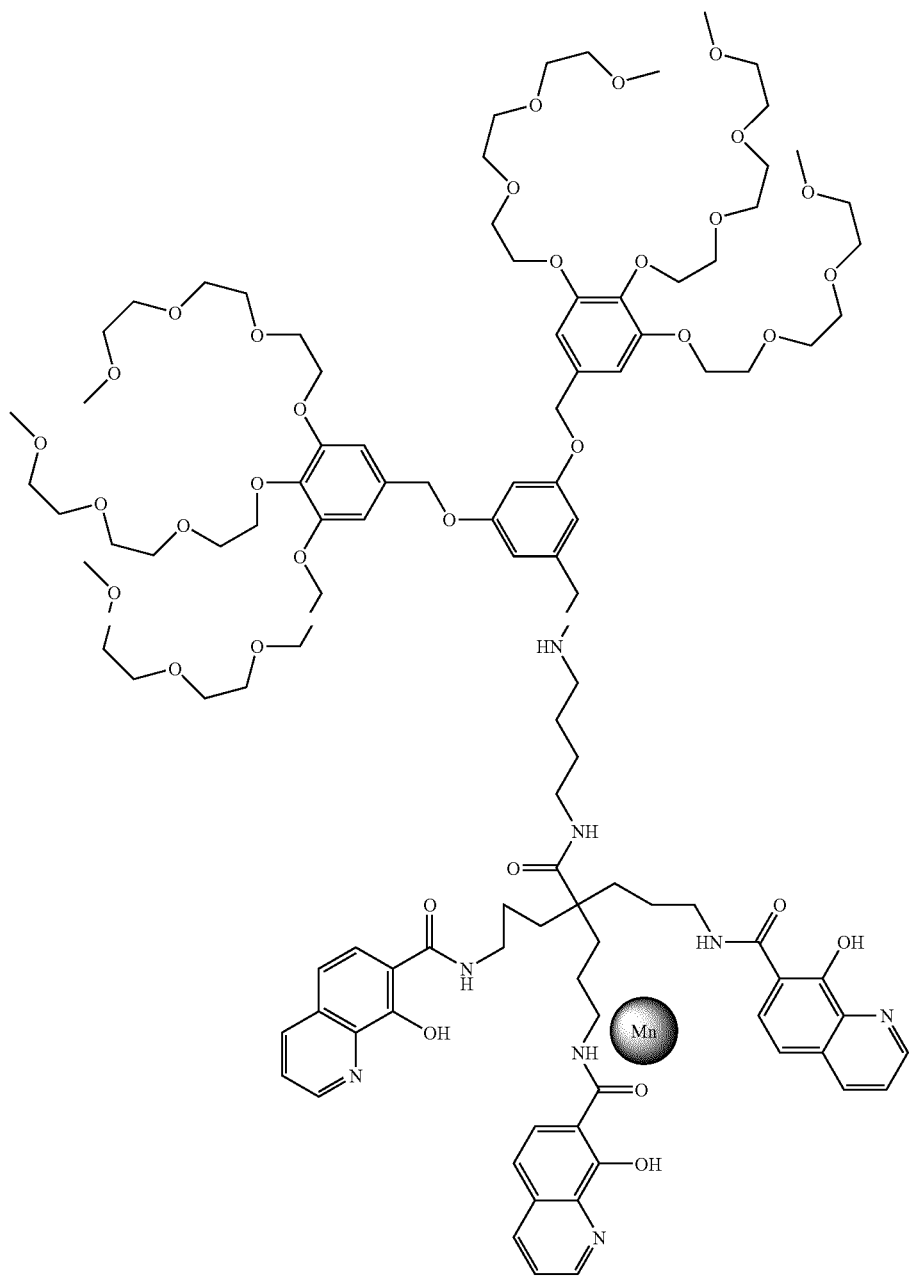

Formula VI-6

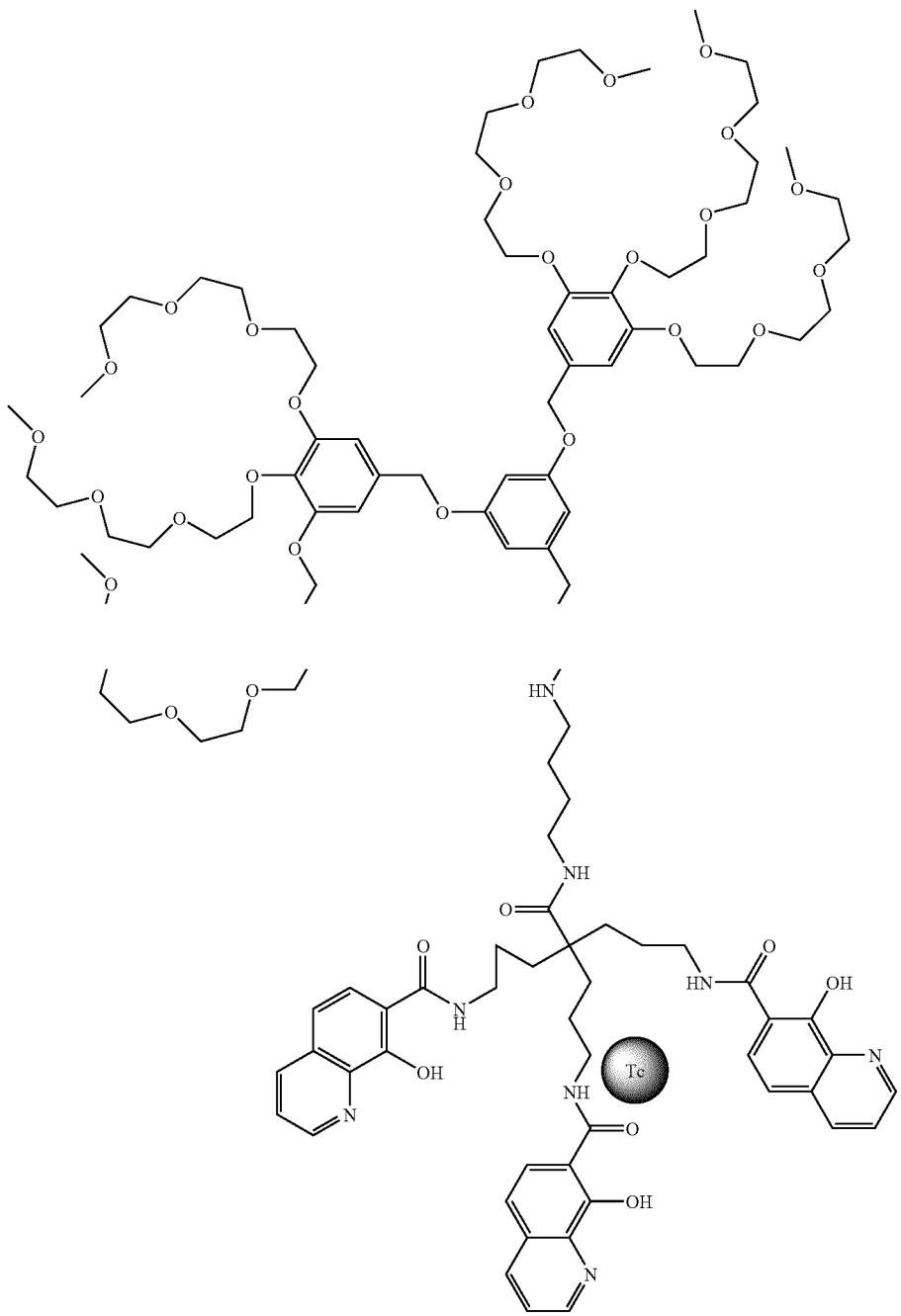

Furthermore, these complexes have the same stability as those in which the chelating agent is a catechol-derived tripod.

The complexes described in the above text, although having considerable advantages, are not specific for a particular organ.

In order to enable them to cross the blood-brain barrier, in a third embodiment of the invention, the lipophilicity of the complexes of the invention is increased by functionalizing at least one dendrite of the dendritic structure with a hydrophobic group. This group is preferably a tert-butyl group.

Thus, the third embodiment of the invention concerns dendritic chelated complexes having general formula I, in which $X_1$ is a tert-butyl group and p1 is an integer equal to 0 to 12, limits included.

More particularly, in this third embodiment of the invention, a preferred complex is a complex of general formula I, in which n=p2=p3=p4=0, the marker M is $Gd^{3+}$, each dendrite of the dendritic structure [D] is a polyethylene glycol chain having 3 ethylene glycol units, m=1, C is diethylenetriamine-pentaacetic acid, $X_1$ is a tert-butyl (tBu) group, p1=3, B is $Na^+$ and z=1. This complex has formula VII-1 below:

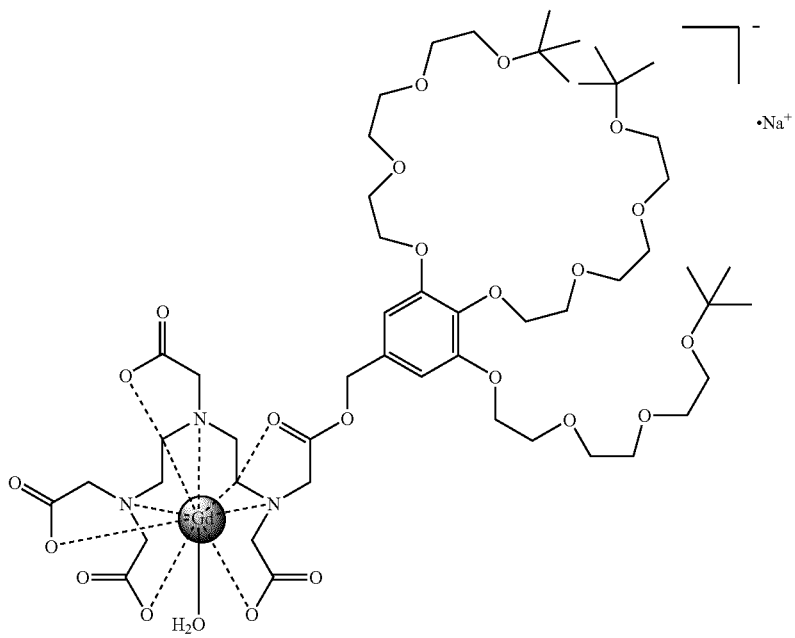

Formula VII-1

Another preferred complex according to the third embodiment of the invention is a complex of general formula I, in which n=p2=p3=p4=0, the marker M is $Mn^{2+}$, each dendrite of the dendritic structure [D] is a polyethylene glycol chain having 3 ethylene glycol units, m=1, C is diethylenetriaminepentaacetic acid, $X_1$ is a tert-butyl (tBu) group, p1=3, B is $Na^+$ and z=2. This complex has the following formula VII-2:

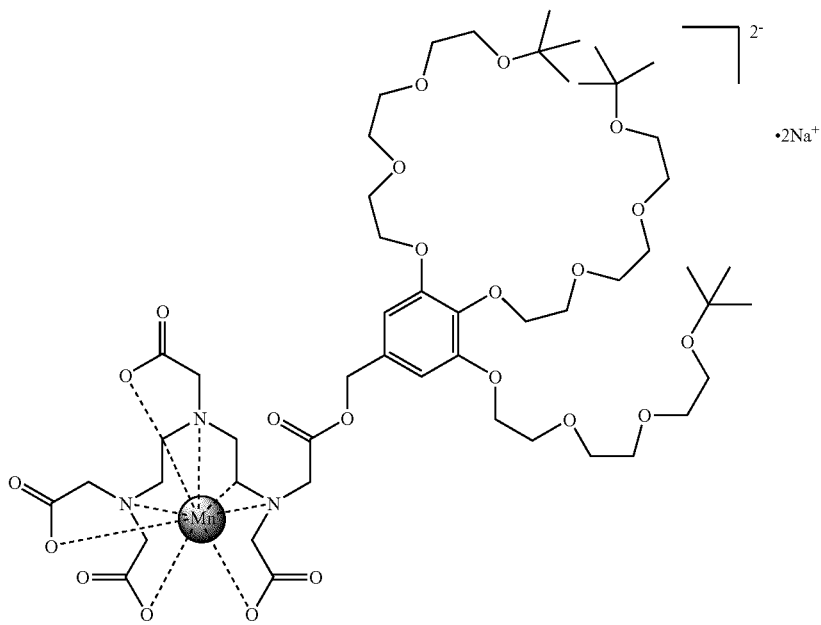

Formula VII-2

Another preferred complex according to the third embodiment of the invention is a complex of general formula I, in which n=p2=p3=p4=0, the marker M is $99mTc^{3+}$, each dendrite of the dendritic structure [D] is a polyethylene glycol chain having 3 ethylene glycol units, m=1, C is diethylenetriaminepentaacetic acid, $X_1$ is a tert-butyl (tBu) group, p1=3, B is $Na^+$ and z=1. This complex has the following formula VII-3:

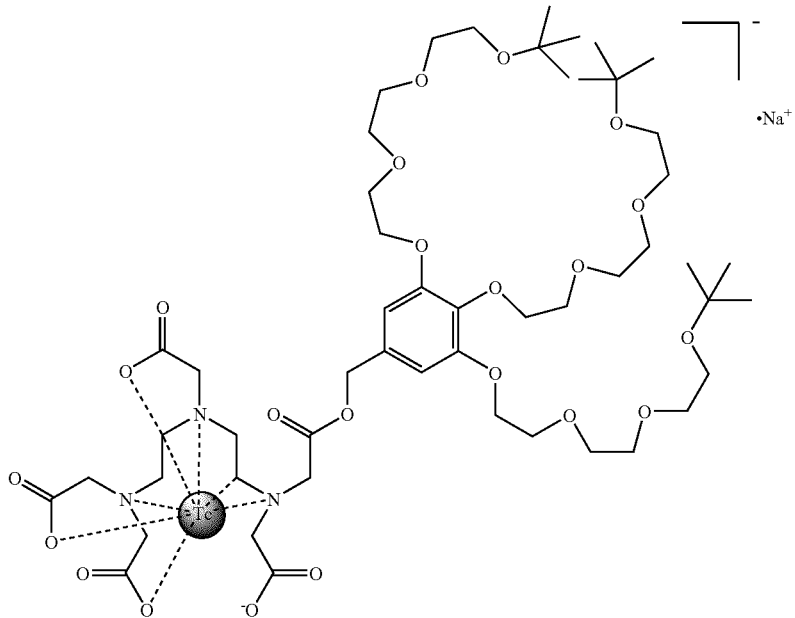

Formula VII-3

Of course, the complexes of the invention comprising a second-generation (G2) dendritic structure, i.e. m=2, are also part of the preferred complexes according to the third embodiment of the invention.

These complexes are:
the complex of general formula I, in which n=p2=p3=p4=0, the marker M is $Gd^{3+}$, each dendrite of the dendritic structure [D] is a polyethylene glycol chain having 3 ethylene glycol units, m=2, C is diethylenetriaminepentaacetic acid, $X_1$ is a tert-butyl (tBu) group, p1=6, B is $Na^+$ and z=1. This complex has the following formula VIII-1:

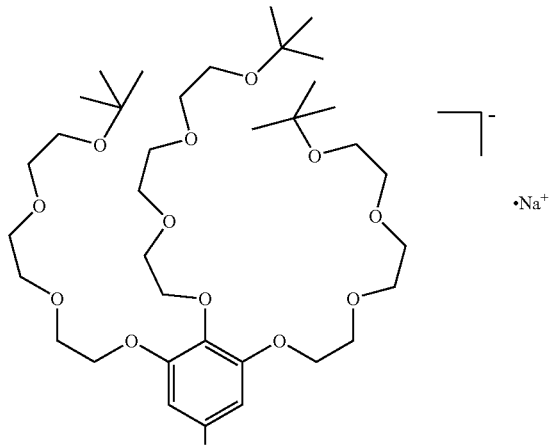

Formula VIII-1

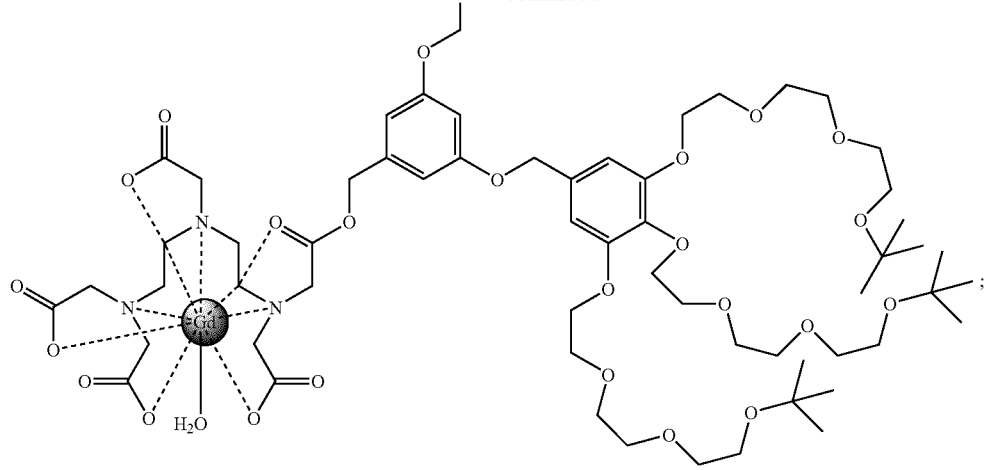
the complex of general formula I, in which n=p2=p3=p4=0, M is $Mn^{2+}$, each dendrite of the dendritic structure [D] is a polyethylene glycol chain having 3 ethylene glycol units, m=2, C is diethylenetriaminepentaacetic acid, $X_1$ is a tert-butyl (tBu) group, p1=6, B is $Na^+$ and z=2. This complex has the following formula VIII-2:
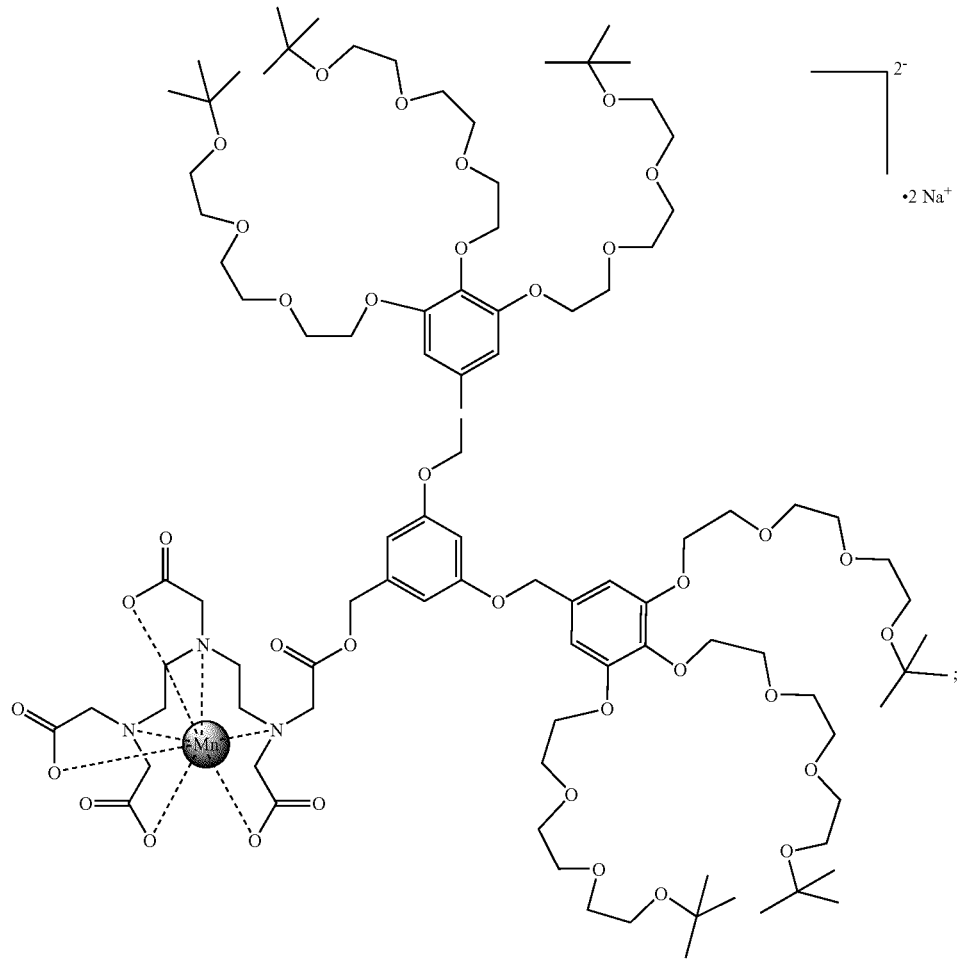
Formula VIII-2 the complex having general formula I, in which n=p2=p3=p4=0, M is 99mTc³⁺, each dendrite of the dendritic structure [D] is a polyethylene glycol chain having 3 ethylene glycol units, m=2, C is diethylenetriaminepentaacetic acid, $X_1$ is a tert-butyl (tBu) group, p1=6, B is Na⁺ and z=1. This complex has the following formula VIII-3:

ity in the brain of healthy mice, and have also shown a more selective profile than that obtained with the commercially available product routinely used, which is calcium trisodium pentetate, sold by Cis-Bio International, in the form of the kit referenced TCK-6.

Complexes of the invention according to the third embodiment, in which the dendrites are tert-butylated tetraethylene

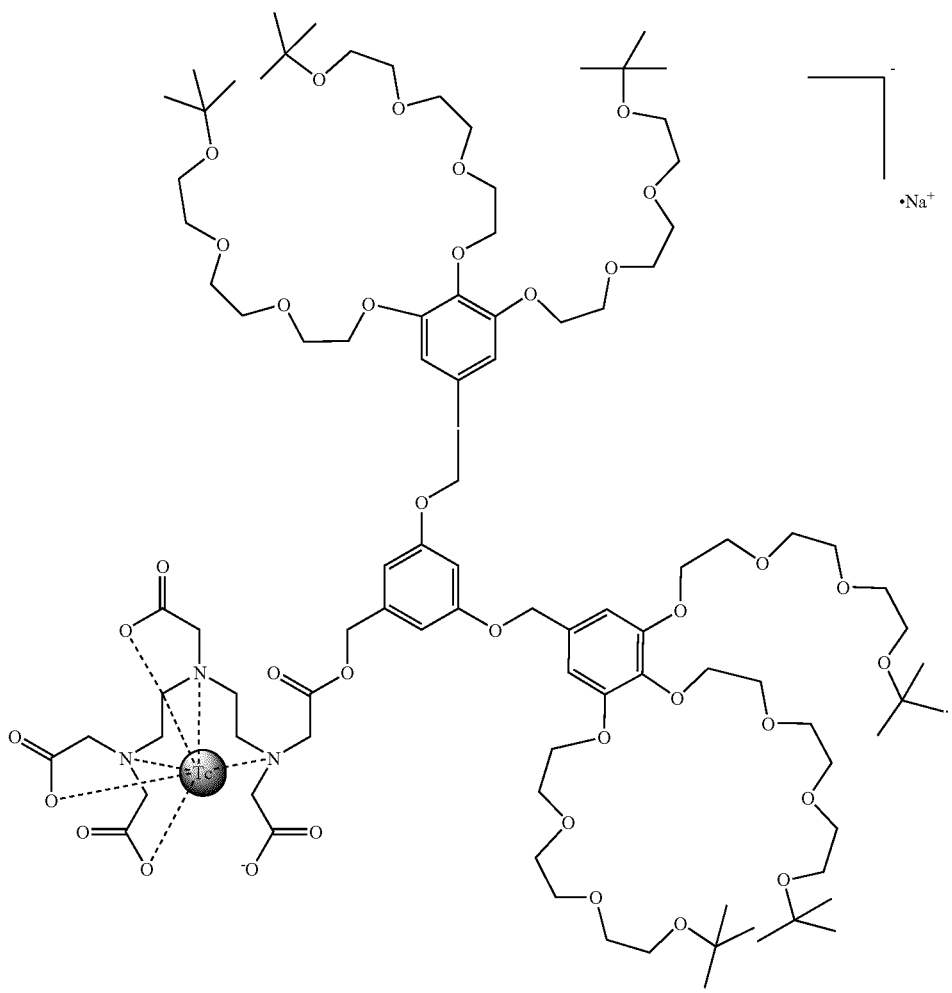

Formula VIII-3

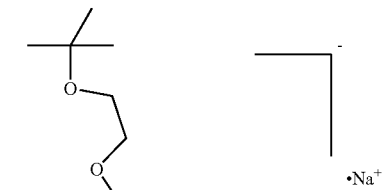

Of course, the complexes corresponding to those of formulae VIII-1 to VIII-3, which are third-generation, i.e. in which m=4, and/or in which the dendrites are tetraethylene glycol chains, and the complexes corresponding to those of formulae IX-1 to IX-3, which are first- or second- or third-generation, comprising a spacer, are also preferred compounds according to the third embodiment of the invention.

The complexes according to the third embodiment of the invention, in which at least one dendrite is functionalized with a tert-butyl group, are particularly preferred in the invention since these complexes cross the blood-brain barrier.

Studies have been carried out on healthy mice using the complexes comprising dendrites with tert-butylated endings, according to the invention, in which the marker is 99mTc³⁺, by nuclear medicine techniques where micromolar concentrations are routinely used.

These experiments have shown that these complexes cross the blood-brain barrier, as shown by counting the radioactivglycol chains and the marker is Gd³⁺ or Mn²⁺, have also been tested by MRI. In these complexes, the considerable reduction in water-solubility brought about by the tert-butyl groups is partly compensated for by the length of the chain of the dendrites, thereby enabling these complexes to have sufficient water-solubility for use in MRI, where millimolar concentrations are necessary.

It has been noted that these complexes also cross the blood-brain barrier.

In order to obtain vectorization of the complexes according to the invention to the brain, one or more dendrites of the dendritic structure of these complexes can be functionalized by an agent which binds to dopaminergic receptors. Such an agent that is preferred in the invention is L-dopamine.

Thus, according to a fourth embodiment of the invention, the complexes that are particularly preferred in the invention for use as a contrast agent having specificity for the brain are the complexes of general formula I, in which the dendrites of each dendritic structure [D] are functionalized with L-dopamine and a group for increasing lipophilicity, such as a tert-butyl group.

Thus, the preferred complexes according to the fourth embodiment of the invention are the following complexes:

the complex of general formula I, in which n=p3=p4=0, each dendrite of the dendritic structure [D] is a polyethylene glycol chain having 3 ethylene glycol units, C is diethylenetriaminepentaacetic acid, M is $Gd^{3+}$, m=1, $X_1$ is a tert-butyl (tBu) group, p1=2, $X_2$ is L-dopamine, p2=1, B is $Na^+$ and z=1. This complex has the following formula IX-1:

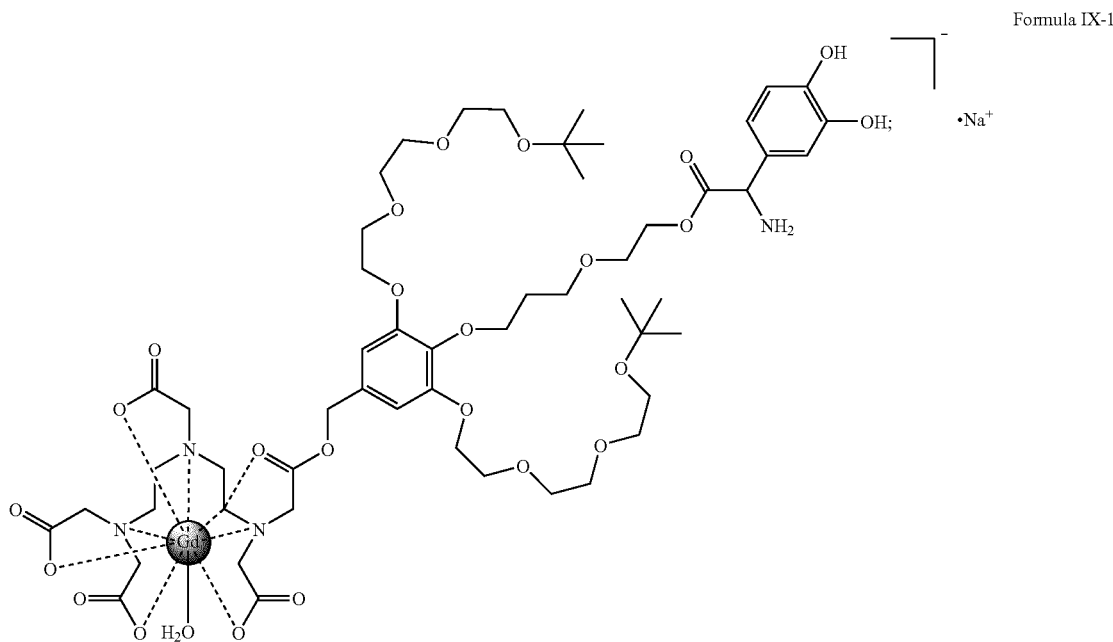

Formula IX-1 the complex of general formula I, in which n=p3=p4=0, each dendrite of the dendritic structure [D] is a polyethylene glycol chain having 3 ethylene glycol units, C is diethylenetriaminepentaacetic acid, M is $Mn^{2+}$, m=1, $X_1$ is a tert-butyl (tBu) group, p1=2, $X_2$ is L-dopamine, p2=1, B is $Na^+$ and z=2. This complex has the following formula IX-2:

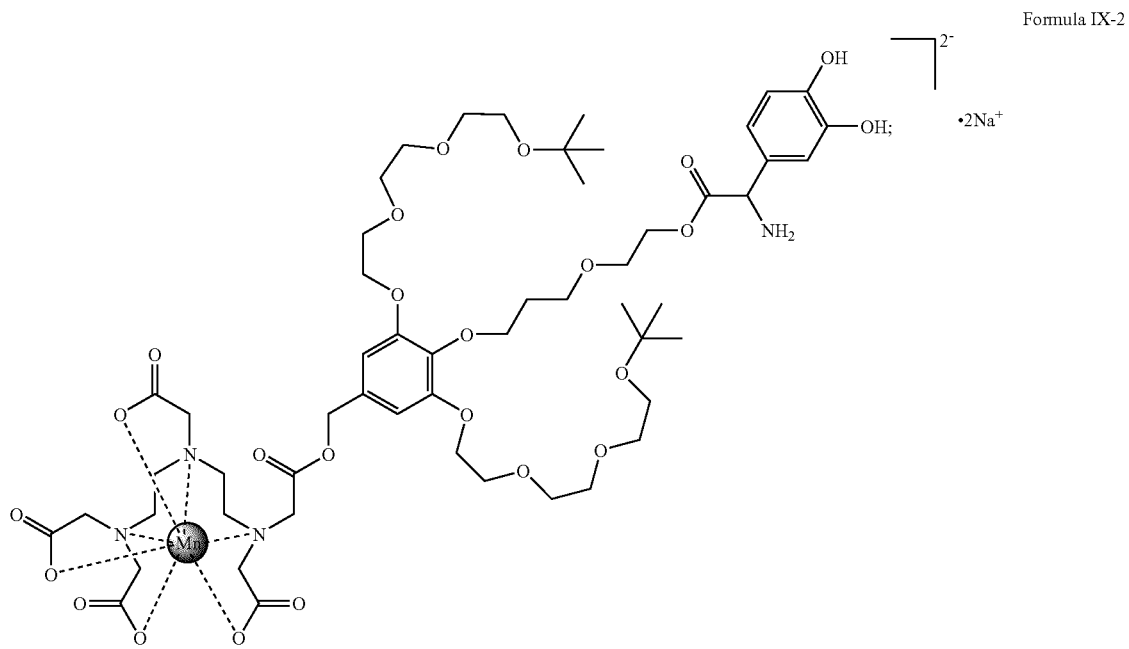

Formula IX-2 the complex of formula I, in which n=p3=p4=0, each dendrite of the dendritic structure [D] is a polyethylene glycol chain having 3 ethylene glycol units, C is diethylenetriaminepentaacetic acid, M is 99mTc³⁺, m=1, $X_1$ is a tert-butyl (tBu) group, p1=2, $X_2$ is L-dopamine, p2=1, B is Na⁺ and z=1. This complex has the following formula IX-3:

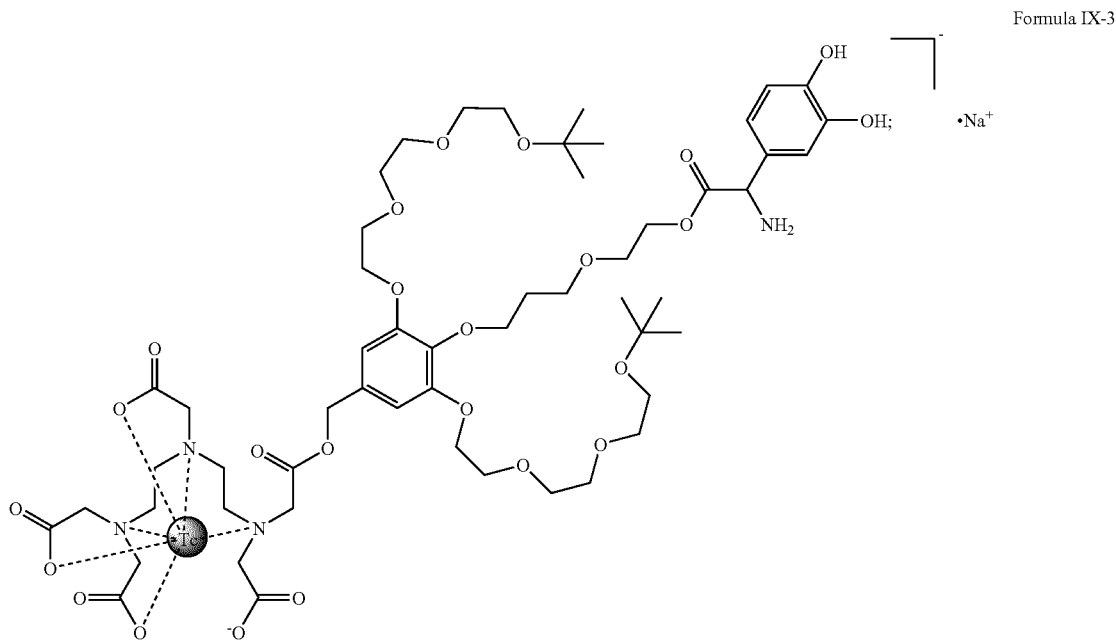

Formula IX-3 the complex of general formula I, in which n=p3=p4=0, each dendrite of the dendritic structure [D] is a polyethylene glycol chain having 3 ethylene glycol units, C is diethylenetriaminepentaacetic acid, M is Gd³⁺, m=2, $X_1$ is a tert-butyl (tBu) group, p1=4, $X_2$ is L-dopamine, p2=2, B is Na⁺ and z=1. This complex has the following formula X-1:

Formula X-1

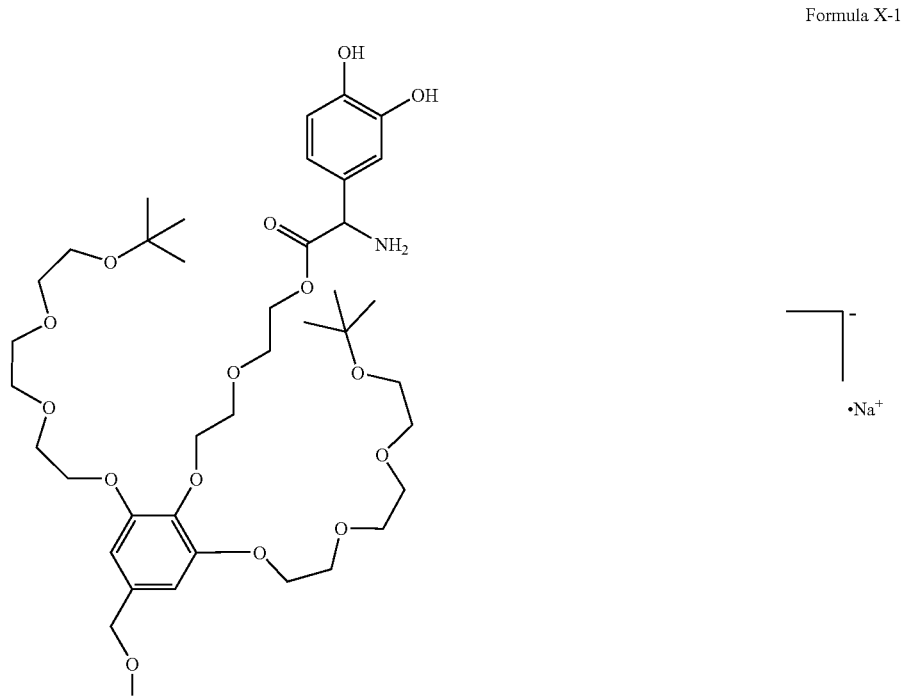

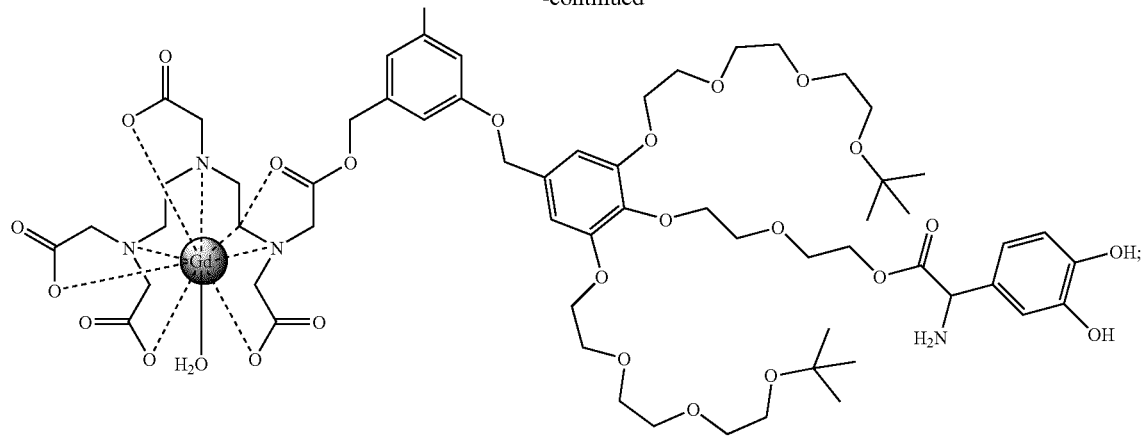
the complex of general formula I, in which n=p3=p4=0, each dendrite of the dendritic structure [D] is a polyethylene glycol chain having 3 ethylene glycol units, C is diethylenetriaminepentaacetic acid, M is $Mn^{2+}$, m=2, $X_1$ is a tert-butyl (tBu) group, p1=4, $X_2$ is L-dopamine, p2=2, B is $Na^+$ and z=2. This complex has the following formula X-2:
Formula X-2
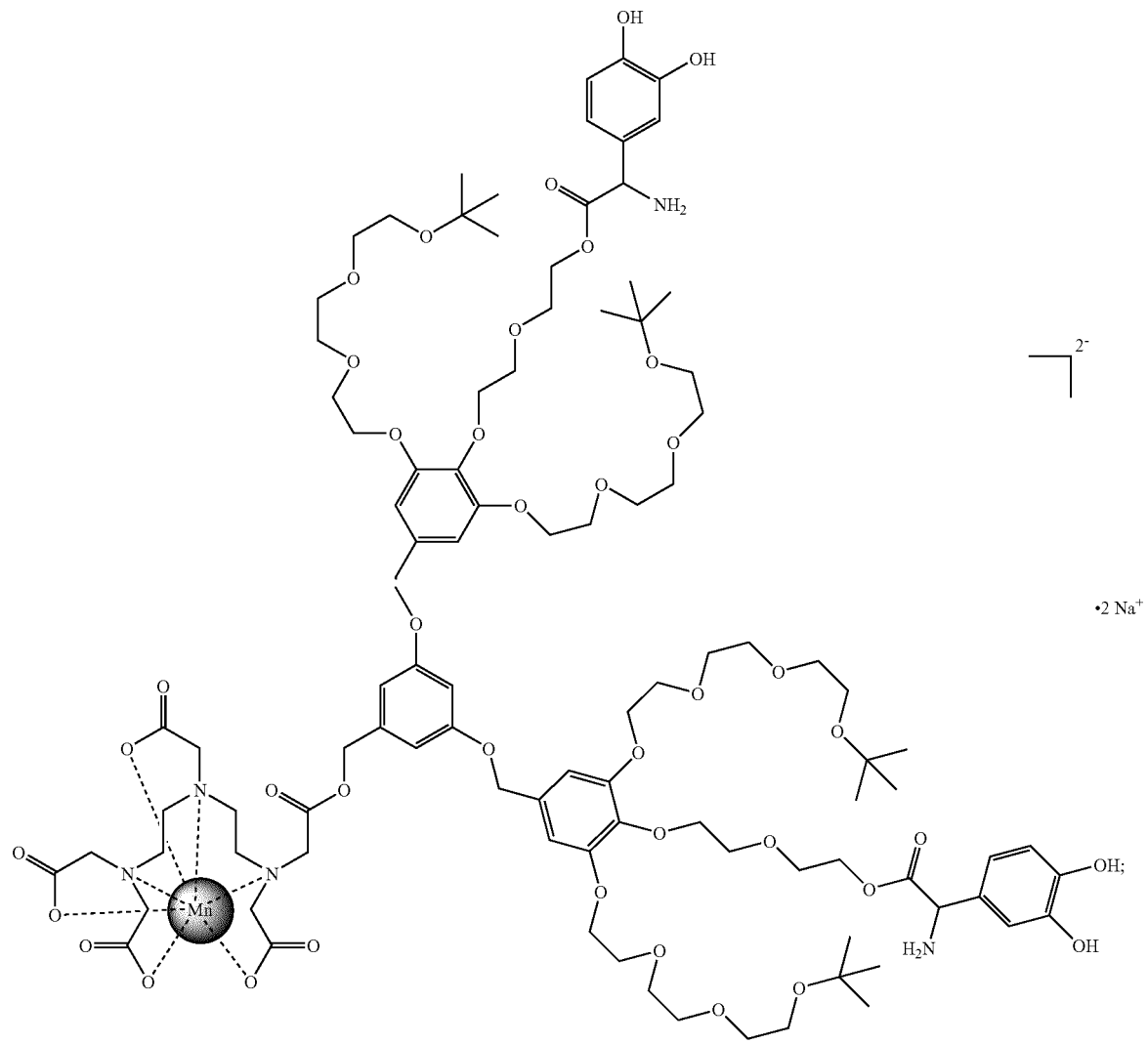

the complex of general formula I, in which n=p3=p4=0, each dendrite of the dendritic structure [D] is a polyethylene glycol chain having 3 ethylene glycol units, C is diethylenetriaminepentaacetic acid, M is 99mTc$^{3+}$, m=2, $X_1$ is a tert-butyl (tBu) group, p1=4, $X_2$ is L-dopamine, p2=2, B is Na$^+$ and z=1. This complex has the following formula X-3:

In this fifth embodiment, the complexes of the invention have a chelate structure which is derived from diethylenetriaminepentaacetic acid (DTPA), a tripod of catechol type, or alternatively a tripod of 8-hydroxyquinoline type. Their dendritic structure has at least four dendrites functionalized with a lipophilic group of tert-butyl (tBu) type, and at least one other dendrite functionalized with a group which confers Formula X-3

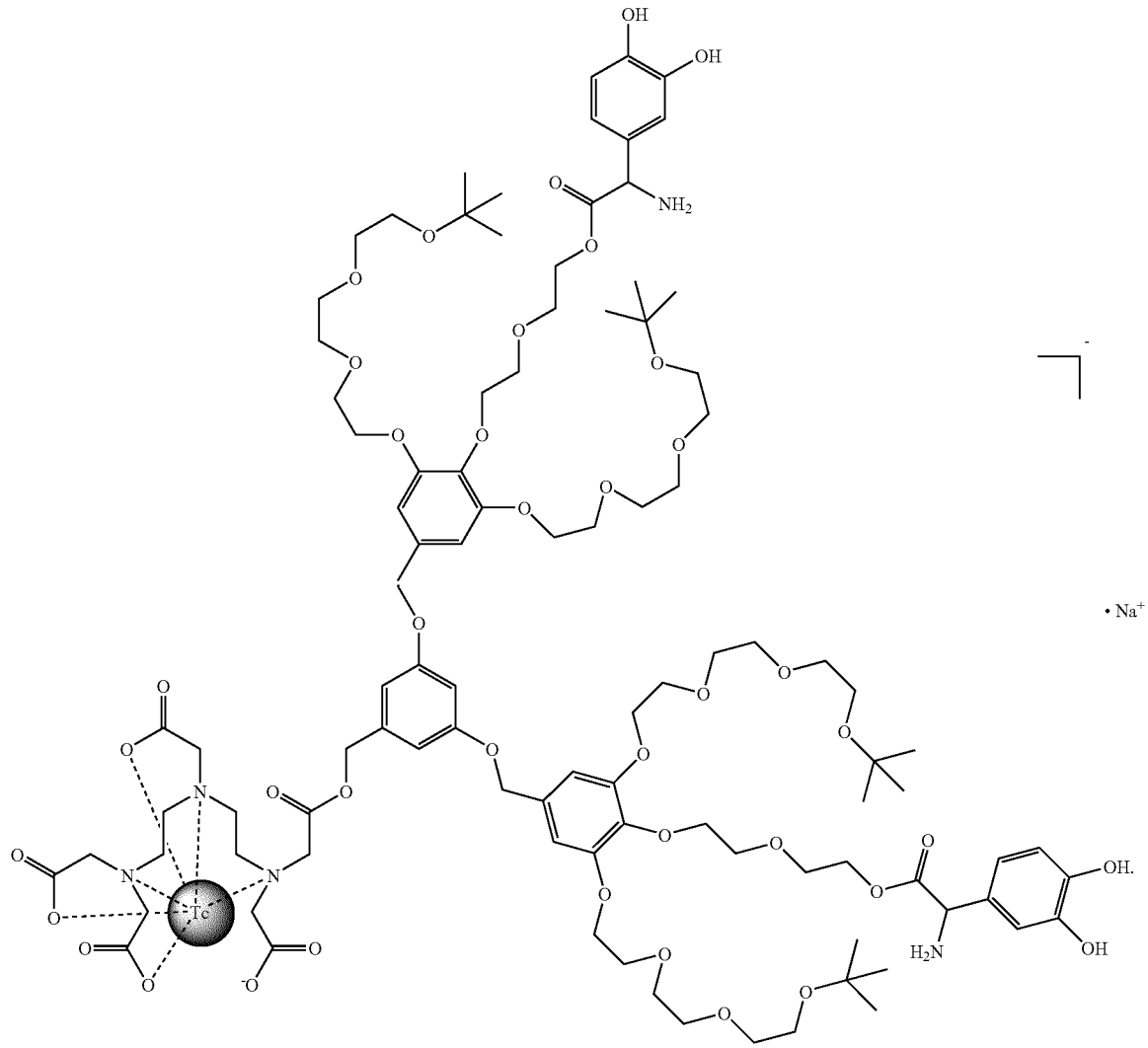

The complexes corresponding to those of formula IX-1 to X-3 above, but in which the dendrites are tetraethylene glycol chains and/or of third generation and/or comprising a spacer according to the invention, are also preferred complexes of the fourth embodiment of the invention.

According to a fifth embodiment of the invention, which is particularly preferred, the complexes of the invention have high stability in the organism, cross the blood-brain barrier, have vectorization to the brain and have a therapeutic activity for neurodegenerative diseases, thereby making them particularly advantageous compounds with therapeutic activity.

thereon a specificity for the brain, and at least one other dendrite functionalized with a therapeutic agent for neurodegenerative diseases.

Thus, the preferred complexes according to the fifth embodiment of the invention are the complexes of general formula I, in which each dendrite of the dendritic structure [D] is a polyethylene glycol chain having 3 ethylene glycol units, the chelating agent C is either diethylenetriaminepentaacetic acid, or a catechol-derived tripod, or an 8-hydroxyquinoline-derived tripod, m=2, the marker M is either Gd$^{3+}$, or Mn$^{2+}$, or 99mTc$^{3+}$, $X_1$ is a tert-butyl group, p1=4, $X_2$ is L-dopamine, p2=1, $X_3$ is a therapeutic agent for neurodegenerative diseases, such as memantine, p3=1, p4=0, n=0, B is Na$^+$ and z=0, 1, 2, 3, or 4, of formula A below:

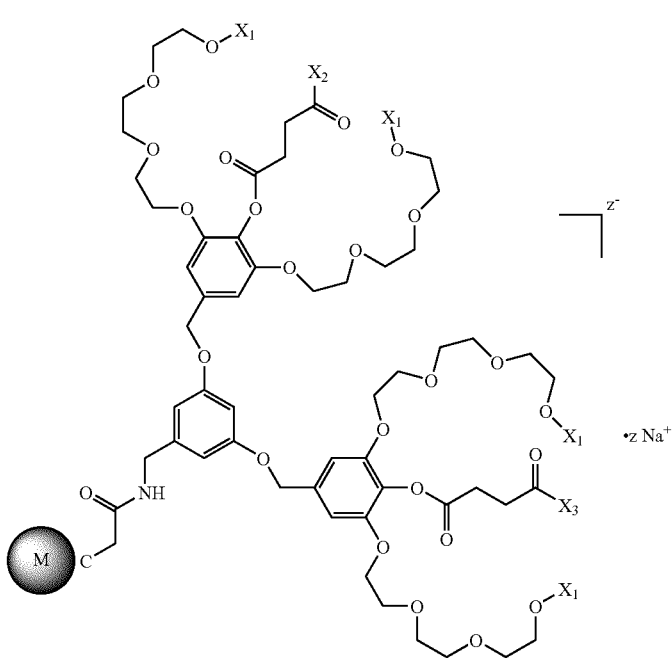

Formula A

The complexes corresponding to those of formula A above, in which the dendrites are tetraethylene glycol chains and/or which comprise a spacer according to the invention and/or which are of third or first generation, are also preferred compounds of the invention according to the fifth embodiment of the invention.

All the complexes of the invention can be synthesized by a method comprising from 6 to 19 steps starting from triethylene glycol using methyl 3,4,5-trihydroxybenzoate or hydroxybenzyl alcohol.

Thus, other subjects of the invention are the methods for synthesizing the complexes of formula I.

The method for synthesizing the dendritic chelated complexes according to the first embodiment of the invention, in which the chelate is DTPA, the dendrites are not functionalized, and comprising a second-generation (G2, m=2) dendritic structure [D], of formulae II-1 to II-3, comprises the following steps:

a) reaction of triethylene glycol monomethyl ether with tosyl chloride,
b) reaction of the tosylate obtained in step a) with methyl 3,4,5-trihydroxybenzoate,
c) reduction of the product obtained in step b), preferably with LiAlH$_4$, so as to obtain the corresponding alcohol,
d) bromination of the product obtained in step c),
e) reaction of the product obtained in step d) with methyl 3,5-dihydroxybenzoate,
f) reduction of the product obtained in step e), preferably with LiAlH$_4$,
g) reaction of the product obtained in step f) with diethylenetriaminepentaacetic dianhydride,
h) reaction of the product obtained in step g) with Gd chloride or Mn chloride or pertechnetate.

Another subject of the invention is the method for synthesizing the complexes according to the second embodiment of the invention, in which the dendrites of the complex are not functionalized but the DTPA chelate is replaced with a catechol-derived or 8-hydroxyquinoline-derived tripod, in order to increase the stability of these complexes, and comprising a first-generation (G1, m=1) dendritic structure [D], of formulae III-1 to III-3, IV-1 to IV-3, comprising the following steps:

Formulae III-1 to III-3:
a) allylation of 2,3-dihydroxybenzoic acid with allyl bromide,
b) saponification of the product obtained in step a) in order to obtain the corresponding acid,
c) fluorination of the product obtained in step b) in order to obtain the corresponding acid fluoride,
a') reduction of the trinitrile tripod in order to obtain the triamine tripod,
b') coupling reaction between the tripod obtained in step a') and the product obtained in step c),
c') deprotection, with tetrabutylammonium fluoride, TBAF, of the alcohol function of the product obtained in b'),
d') Swern oxidation of the product obtained in c') in order to obtain the corresponding carboxylic acid,
e') coupling reaction between the product obtained in d') and 1,4-butanediamine, monoprotected with a tert-butylcarboxyl function, Boc,
f') deprotection of the amine function of the product obtained in e'),
a") synthesis of triethylene glycol monomethyl ether,
b") reaction of the triethylene glycol monomethyl ether with tosyl chloride, c") reaction of the tosylate obtained in step b") with methyl 3,4,5-trihydroxybenzoate, d") saponification of the product obtained in step c") in order to obtain the corresponding acid, a''') coupling reaction between the product obtained in f') and that obtained in d"), b''') deallylation of the catechol functions, c''') reaction of the product obtained in step b") with Gd chloride or Mn chloride or pertechnetate.

Yet another subject of the invention is a method for synthesizing the complexes of formulae IV-1 to IV-3, which comprises the following steps:

a) allylation of 8-hydroxyquinoline-7-carboxylic acid methyl ester with allyl bromide, b) saponification of the product obtained in step a) in order to obtain the corresponding acid, c) fluorination of the product obtained in step b) in order to obtain the corresponding acid fluoride, a') reduction of the trinitrile tripod in order to obtain the triamine tripod, b') coupling reaction between the tripod obtained in step a') and the product obtained in step c), c') deprotection, with TBAF, of the alcohol function of the product obtained in b'), d') Swern oxidation of the product obtained in c') in order to give the corresponding carboxylic acid, e') coupling reaction between the product obtained in d') and 1,4-butanediamine, monoprotected with a Boc function, f') deprotection of the amine function of the product obtained in e'), a") synthesis of triethylene glycol monomethyl ether, b") reaction of the triethylene glycol monomethyl ether with tosyl chloride, c") reaction of the tosylate obtained in step b") with methyl 3,4,5-trihydroxybenzoate, d") saponification of the product obtained in step c") in order to obtain the corresponding acid, a''') coupling reaction between the product obtained in f') and that obtained in d"), b''') deallylation of the alcohol functions, c''') reaction of the product obtained in step b''') with Gd chloride or Mn chloride or pertechnetate.

In the same manner, another subject of the invention is the method for synthesizing the complexes according to the invention in which the DTPA chelate is replaced with a catechol-derived or 8-hydroxyquinoline-derived tripod, in order to increase the stability of these complexes, and comprising a second-generation (G2, m=2) dendritic structure [D], of formulae V-1 to V-3, VI-1 to VI-3, comprising the following steps:

Formulae V-1 to V-3:

a) allylation of 2,3-dihydroxybenzoic acid with allyl bromide, b) saponification of the product obtained in step a) in order to obtain the corresponding acid, c) fluorination of the product obtained in step b) in order to obtain the corresponding acid fluoride, a') reduction of the trinitrile tripod in order to obtain the triamine tripod, b') coupling reaction between the tripod obtained in step a') and the product obtained in step c), c') deprotection, with TBAF, of the alcohol function of the product obtained in b'), d') Swern oxidation of the product obtained in c') in order to give the corresponding carboxylic acid, e') coupling reaction between the product obtained in d') and 1,4-butanediamine, monoprotected with a Boc function, f') deprotection of the amine function of the product obtained in e'), a") synthesis of triethylene glycol monomethyl ether, b") reaction of the triethylene glycol monomethyl ether with tosyl chloride, c") reaction of the tosylate obtained in step b") with methyl 3,4,5-trihydroxybenzoate, d") reduction of the product obtained in step c"), preferably with LiAlH$_4$, so as to obtain the corresponding alcohol, e") bromination of the product obtained in step d"), f") reaction of the product obtained in step e") with methyl 3,5-dihydroxybenzoate, g") saponification of the product obtained in step f") in order to obtain the corresponding acid, a''') coupling reaction between the product obtained in f') and that obtained in g"), b''') deallylation of the catechol functions, c''') reaction of the product obtained in step b''') with Gd chloride or Mn chloride or pertechnetate.

Another subject of the invention is the method for synthesizing the compounds of the invention of formulae VI-1 to VI-3, which comprises the following steps:

a) allylation of 8-hydroxyquinoline-7-carboxylic acid methyl ester with allyl bromide, b) saponification of the product obtained in step a) in order to obtain the corresponding acid, c) fluorination of the product obtained in step b) in order to obtain the corresponding acid fluoride, a') reduction of the trinitrile tripod in order to obtain the triamine tripod, b') coupling reaction between the tripod obtained in step a') and the product obtained in step c), c') deprotection, with TBAF, of the alcohol function of the product obtained in b'), d') Swern oxidation of the product obtained in c') in order to give the corresponding carboxylic acid, e') coupling reaction between the product obtained in d') and 1,4-butanediamine, monoprotected with a Boc function, f') deprotection of the amine function of the product obtained in e'), a") synthesis of triethylene glycol monomethyl ether, b") reaction of the triethylene glycol monomethyl ether with tosyl chloride, c") reaction of the tosylate obtained in step b") with methyl 3,4,5-trihydroxybenzoate, d") reduction of the product obtained in step c"), preferably with LiAlH$_4$, so as to obtain the corresponding alcohol, e") bromination of the product obtained in step d"), f") reaction of the product obtained in step e") with methyl 3,5-dihydroxybenzoate, g") saponification of the product obtained in step f") in order to obtain the corresponding acid, a"') coupling reaction between the product obtained in f') and that obtained in g"), b"') deallylation of the alcohol functions, c"') reaction of the product obtained in step b"') with Gd chloride or Mn chloride or pertechnetate.

Another subject of the invention is the method for synthesizing the complexes of the invention of formulae VII-1 to VII-3, in which the chelate is DTPA and the dendrites of the complex are functionalized with tert-butyl groups, in order to increase the lipophilicity of these complexes, and comprising a first-generation (G1, m=1) dendritic structure [D], comprising the following steps:

a) synthesis of tert-butoxytriethylene glycol from tert-butanol, b) reaction of the product obtained in step a) with tosyl chloride, c) reaction of the tosylate obtained in step b) with methyl 3,4,5-trihydroxybenzoate, d) reduction of the product obtained in step c), preferably with LiAlH$_4$, so as to obtain the corresponding alcohol, e) reaction of the product obtained in step d) with diethylenetriaminepentaacetic dianhydride, f) reaction of the product obtained in step e) with Gd chloride or Mn chloride or pertechnetate.

In the same manner, another subject of the invention is the method for synthesizing the complexes according to the invention in which the chelate is DTPA and the dendrites of the complex are of formulae VIII-1 to VIII-3, functionalized with tert-butyl groups, in order to increase the lipophilicity of these complexes, and comprising a second-generation (G2, m=2) dendritic structure [D], comprising the following steps:

a) synthesis of tert-butoxytriethylene glycol from tert-butanol, b) reaction of the product obtained in step a) with tosyl chloride, c) reaction of the tosylate obtained in step b) with methyl 3,4,5-trihydroxybenzoate, d) reduction of the product obtained in step c), preferably with LiAlH$_4$, so as to obtain the corresponding alcohol, e) bromination of the product obtained in step d), f) reaction of the product obtained in step e) with methyl 3,5-dihydroxybenzoate, g) reduction of the product obtained in step f), preferably with LiAlH$_4$, so as to obtain the corresponding alcohol, h) reaction of the product obtained in step g with diethylenetriaminepentaacetic dianhydride, i) reaction of the product obtained in step h) with Gd (III) chloride or Mn (III) chloride or pertechnetate.

Another subject of the invention is the method for synthesizing the complexes according to the invention (of formulae IX-1 to IX-3) in which the chelate is DTPA and the dendrites of the complex are functionalized with L-dopamine and a group for increasing lipophilicity, such as a tert-butyl group, and comprising a first-generation (G1, m=1) dendritic structure [D], comprising the following steps:

a) synthesis of tert-butoxytriethylene glycol from tert-butanol, b) reaction of the product obtained in step a) with tosyl chloride, a') reaction of methyl 3,4,5-trihydroxybenzoate with acetic anhydride, b') reaction of the product obtained in step a') with allyl bromide, c') basic hydrolysis of the product obtained in step b') with potassium carbonate, d') reaction of the product obtained in step c') with the tosylate obtained in step b), e') deprotection of the alcohol function of the product obtained in step d'), a") protection of L-dopamine with fluorenylmethoxycarbonyl chloride, Fmoc, b") reaction of the product obtained in step a") with allyl bromide, c") reaction of the product obtained in step b") with morpholine, d") esterification of the product obtained in step c"), e") saponification of the product obtained in step d"), f") esterification of the product obtained in step e") with the product obtained in step e'), g") reduction of the product obtained in step f") so as to obtain the corresponding alcohol, h") reaction of the product obtained in step g") with diethylenetriaminepentaacetic dianhydride, i") reaction of the product obtained in step h") with Gd (III) chloride, Mn (II) chloride or pertechnetate.

In the same manner, another subject of the invention is the method for synthesizing the complexes according to the invention (of formulae X-1 to X-3) in which the chelate is DTPA and the dendrites of the complex are functionalized with L-dopamine and a group for increasing lipophilicity, such as a tert-butyl group, and comprising a second-generation (G2, m=2) dendritic structure [D], comprising the following steps:

a) synthesis of tert-butoxytriethylene glycol from tert-butanol, b) reaction of the product obtained in step a) with tosyl chloride, a') reaction of methyl 3,4,5-trihydroxybenzoate with acetic anhydride, b') reaction of the product obtained in step a') with allyl bromide, c') basic hydrolysis of the product obtained in step b'), preferably with potassium carbonate, d') reaction of the product obtained in step c') with the tosylate obtained in step b), e') deprotection of the alcohol function of the product obtained in step d'), a") protection of L-dopamine with Fmoc chloride, b") reaction of the product obtained in step a") with allyl bromide, c") reaction of the product obtained in step b") with morpholine, d") esterification of the product obtained in step c"), e") saponification of the product obtained in step d"), f") esterification of the product obtained in step e") with the product obtained in step e'), g") reduction of the product obtained in step f"), preferably with LiAlH$_4$, so as to obtain the corresponding alcohol, h") bromination of the product obtained in step g"), i") reaction of the product obtained in step h") with methyl 3,5-dihydroxybenzoate, j") reduction of the product obtained in step i"), preferably with LiAlH$_4$, so as to obtain the corresponding alcohol, k") reaction of the product obtained in step j") with diethylenetriaminepentaacetic dianhydride, l") reaction of the product obtained in step k") with Gd (III) chloride, Mn (II) chloride or pertechnetate.

Another subject of the invention is the method for synthesizing the complexes according to the invention (of formula A) in which the chelate is either DTPA or a catechol-derived tripod or an 8-hydroxyquinoline-derived tripod, and the dendrites of the complex are functionalized with L-dopamine, with memantine and with a group for increasing lipophilicity, such as a tert-butyl group, and comprising a second-generation (G2, m=2) dendritic structure [D], comprising the following steps:

a) reaction of methyl 3,5-dihydroxybenzoate with allyl bromide, a') synthesis of tert-butoxytriethylene glycol from tert-butanol, b') reaction of the product obtained in step a') with tosyl chloride, a") reaction of methyl 3,4,5-trihydroxybenzoate with acetic anhydride, b") reaction of the product obtained in step a") with allyl bromide, c") basic hydrolysis of the product obtained in step b"), preferably with potassium carbonate, d") reaction of the product obtained in step c") with the tosylate obtained in step b'), e") deprotection of the alcohol function of the product obtained in step d"), a''') protection of L-dopamine with Fmoc chloride, b''') reaction of the product obtained in step a''') with allyl bromide, c''') reaction of the product obtained in step b''') with morpholine, d''') esterification of the product obtained in c'''), e''') saponification of the product obtained in step d'''), f''') esterification of the product obtained in step e''') with the product obtained in step e"), g''') reduction of the product obtained in step f''') so as to obtain the corresponding alcohol, h''') bromination of the product obtained in step g'''), i''') deprotection of the alcohol function of the product obtained in step h'''), a'''') esterification of the memantine, b'''') saponification of the product obtained in step a''''), c'''') esterification of the product obtained in step b''''), d'''') reduction of the product obtained in step c''''), preferably with LiAlH$_4$, e'''') bromination of the product obtained in step d''''), f'''') etherification of the product obtained in step e'''') with the product obtained in step a), g'''') deprotection of the alcohol function of the product obtained in step f''''), h'''') etherification of the product obtained in step g'''') with the product obtained in step i'''), i'''') reduction of the product obtained in step h''''), preferably with LiAlH$_4$, j'''') reaction of the product obtained in step i'''') with either diethylenetriaminepentaacetic dianhydride, or with the catechol tripod, or with the 8-hydroxyquinoline tripod.

The invention also relates to a pharmaceutical composition comprising at least one complex according to the invention or at least one complex obtained by means of a method according to the invention, in a pharmaceutically acceptable excipient.

This pharmaceutical composition may be used as a contrast agent for the detection, and understanding the mechanism, of neurodegenerative diseases such as Alzheimer's disease, Parkinson's disease and multiple sclerosis.

However, this pharmaceutical composition may also be used for treating or improving a neurodegenerative disease such as Alzheimer's disease, Parkinson's disease or multiple sclerosis, when the dendrites of the dendritic structure of the complexes according to the invention are functionalized with a therapeutic agent such as memantine (1,3-dimethyl-5-aminoadamantane).

In addition to the above arrangements, the invention also comprises other arrangements, which will emerge from the description which follows, and which refer to examples of methods of synthesizing the complexes of the invention.

It should be understood, however, that these examples are given only by way of illustration of the subject of the invention, of which they in no way constitute a limitation.

Materials and Methods of Analysis Used

The $^1$H and $^{13}$C NMR spectra were recorded on a Brucker AM300 spectrometer (300 MHz). The internal reference for the spectra corresponds to the peak of the non-deuterated solvent (CDCl$_3$: 7.27 ppm, CD$_2$Cl$_2$: 5.32 ppm).

All the commercially available products and reactants were used without prior treatment and come from the companies SIGMA-Aldrich, ACROS and STREM Chemicals.

EXAMPLE 1

Synthesis of the Complexes of Formulae from II-1 to II-3

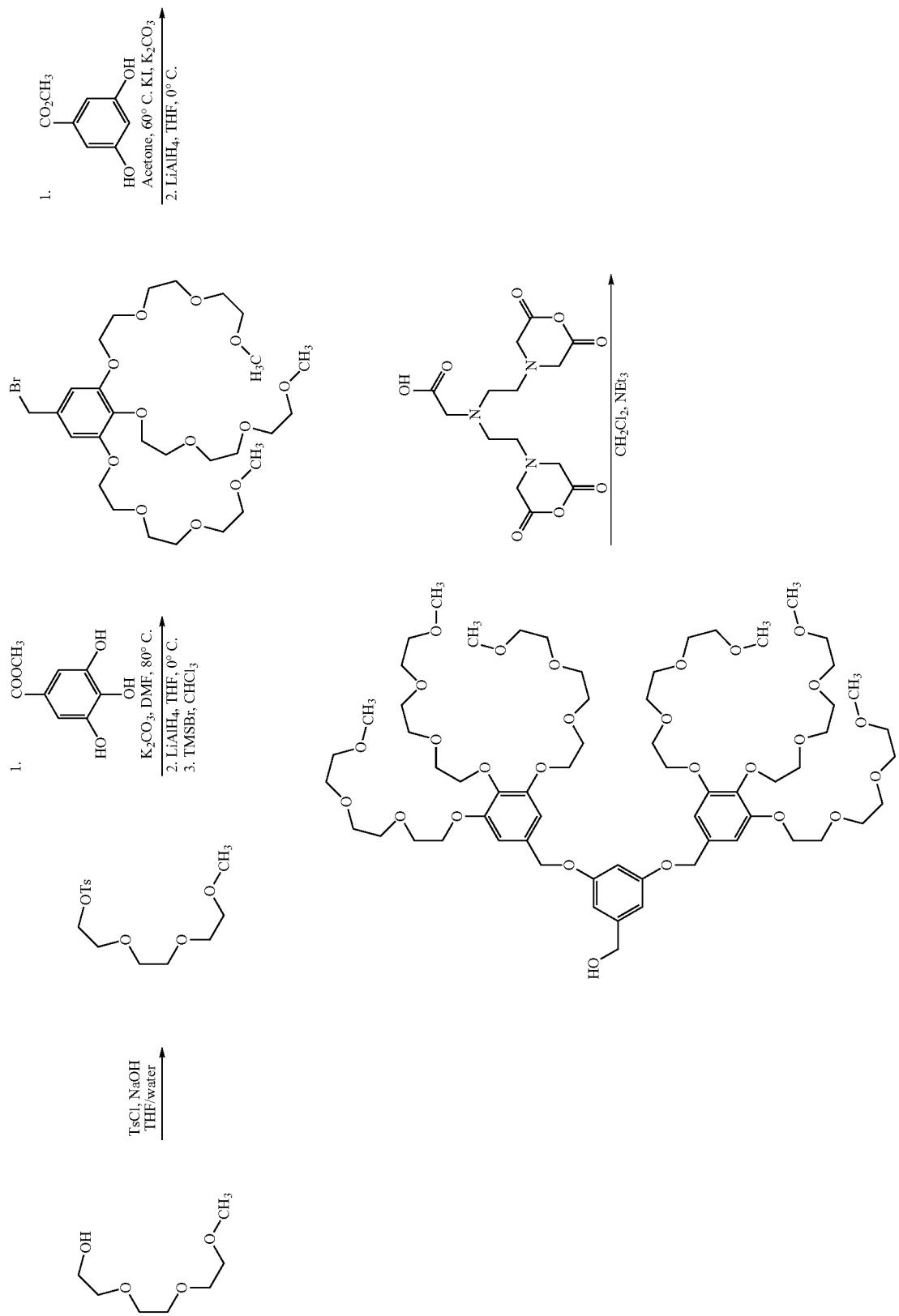

-continued
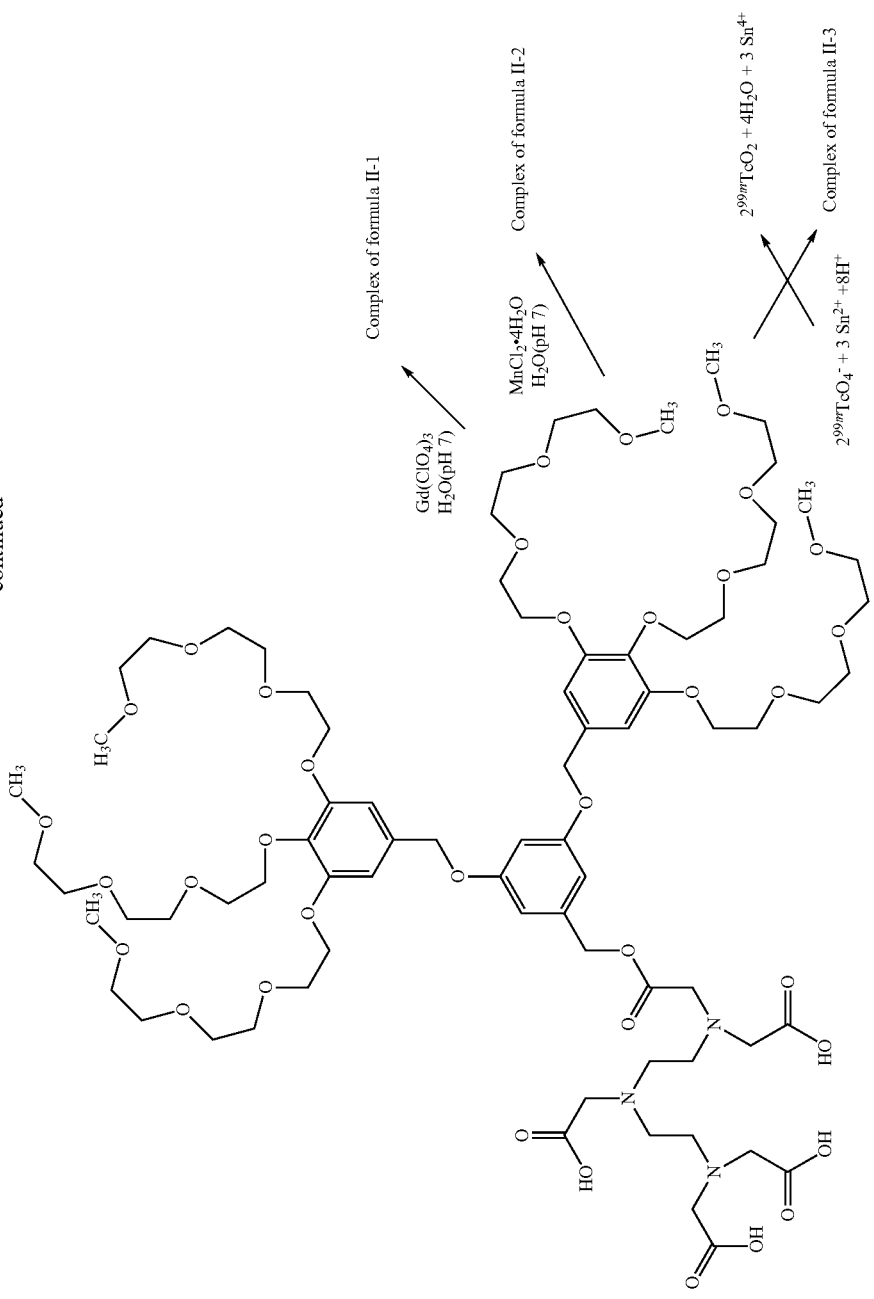

Step a): Reaction of Triethylene Glycol Monomethyl Ether with Tosyl Chloride

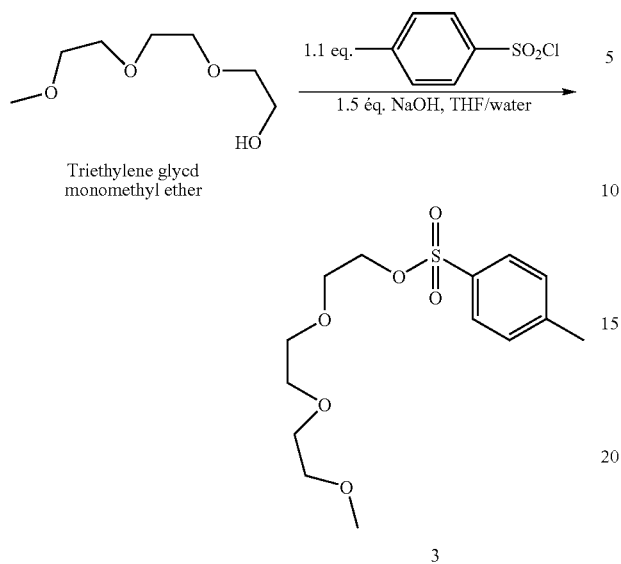

In a 500 ml round-bottomed flask, triethylene glycol monomethyl ether (20.00 g, 0.122 mol) is added to a solution of sodium hydroxide (7.33 g, 0.183 mol) in a distilled water/ THF mixture (20 ml/140 ml). The solution is cooled to 0° C. using an ice bath. A solution of tosyl chloride (25.50 g, 0.134 mol) in 40 ml of THF is then added dropwise, using a dropping funnel, over approximately 30 minutes. The reaction medium thus obtained is stirred at ambient temperature for 24 hours and then poured into an 800 ml beaker containing 200 ml of a saturated aqueous solution of NaCl, cooled to 0° C. Two phases are then observed. The yellowish upper phase, corresponding to the organic phase, is extracted using a separating funnel. It is subsequently washed with 500 ml of a saturated aqueous solution of NaCl. The initial aqueous phase is subsequently treated with 200 ml of $CH_2Cl_2$ and the new organic phase obtained, which is the lower phase this time ($d^{20}_{CH2Cl2}$=1.325), is recovered. The two organic phases thus obtained are combined, washed with a saturated aqueous solution of NaCl (500 ml), dried over anhydrous $MgSO_4$, filtered, and then evaporated using a rotary evaporator.
The product 3 is obtained with a yield of 94% (36.30 g, 0.113 mol). Colorless oil.

Step b): Reaction of the Tosylate Obtained in Step a) with Methyl 3,4,5-Trihydroxybenzoate

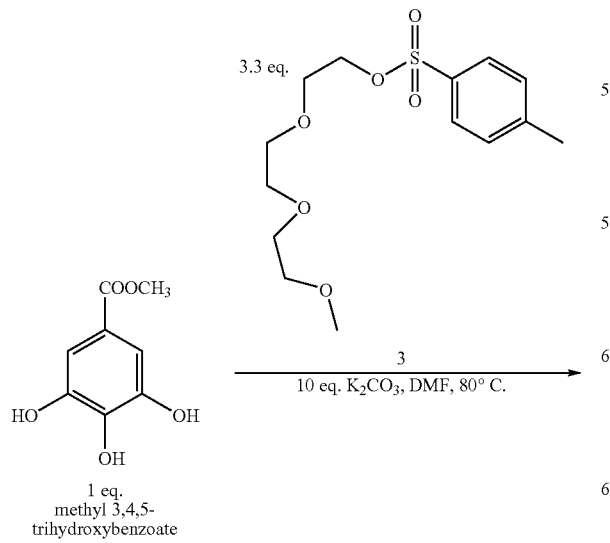

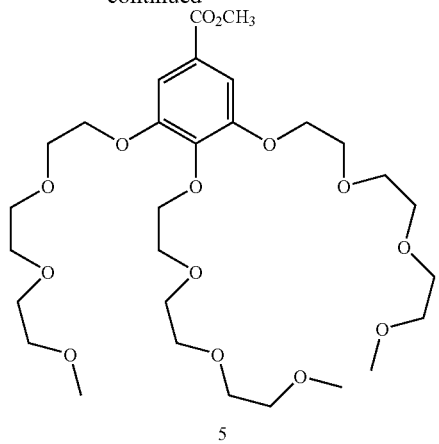

A solution of tosylate 3 (33.75 g, 0.106 mol) and of methyl 3,4,5-trihydroxybenzoate (5.95 g, 0.032 mol) and of $K_2CO_3$ (44.4 g, mol) in dimethylformamide (DMF) (100 ml) is stirred and heated at 80° C. using an oil bath for 72 hours.

After having stopped the heating, the reaction medium is cooled to ambient temperature and then filtered through Celite. After evaporation of the solvent, the residue of the filtrate is taken up in 300 ml of $CH_2Cl_2$. The organic phase thus obtained is washed with 3×300 ml of a saturated aqueous solution of NaCl, dried over anhydrous $MgSO_4$, then filtered and evaporated to dryness, so as to give 32.60 g of crude product to be purified.

Purification: chromatography column 4.5 cm in diameter, $V_{silica}$=500 ml, eluent: 1/1 $CH_2Cl_2$/acetone.

The product 5 is obtained with a yield of 90% (17.65 g, 0.026 mol).

Step c): Reduction of the Product Obtained in Step b), Preferably with $LiAlH_4$, so as to Obtain the Corresponding Alcohol

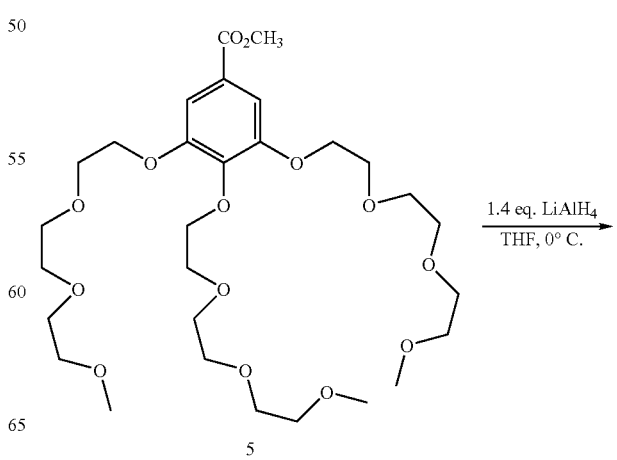

77
-continued

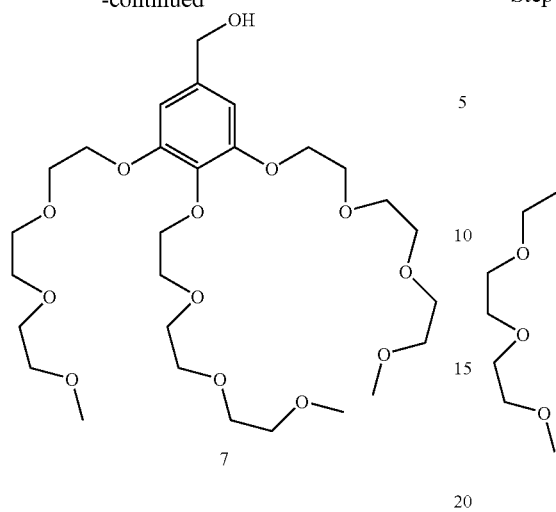

A 1M solution of LiAlH$_4$ in THF (34 ml, 0.034 mol) is added dropwise, very carefully, to a solution of product 5 (15.00 g, 0.024 mol) in 20 ml of anhydrous THF kept under argon and cooled to 0° C. with an ice bath. After stirring for 20 hours at ambient temperature, the reaction medium is cooled to 0° C. with an ice bath and the reaction is stopped by adding 20 ml of ethyl acetate (EtOAc), then 20 ml of methanol (MeOH) and, finally, 20 ml of water. The addition of ethyl acetate results in a violent reaction if it is not introduced slowly, the addition of water causes the salts to precipitate. The reaction medium is then filtered through Celite and then evaporated to dryness. The residue obtained is taken up in 200 ml of CH$_2$Cl$_2$, and washed with 3×200 ml of a saturated aqueous solution of NaCl. The organic phase obtained is dried over anhydrous MgSO$_4$, filtered, and evaporated to dryness.

The product 7 is obtained with a yield of 79% (11.18 g, 0.0188 mol).

78

Step d): Bromination of the Product Obtained in Step c)

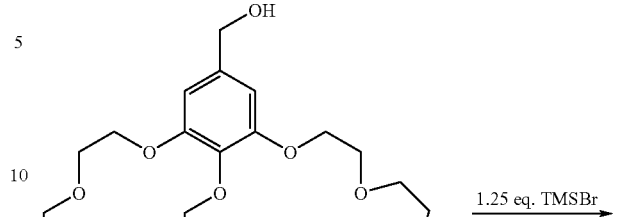

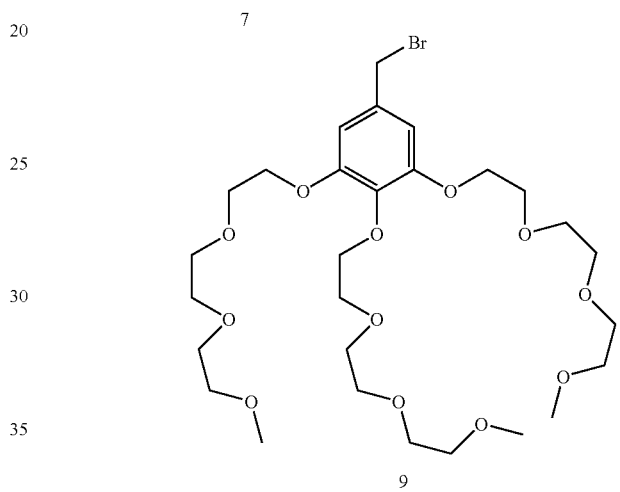

TMSBr (2.67 g, 2.3 ml, 0.017 mol) is added dropwise, using a syringe, to a solution of product 7 (8.30 g, 0.014 mol) in 10 ml of anhydrous CHCl$_3$ kept under an inert atmosphere (argon) and at 0° C. using an ice bath. After stirring for 48 hours, the solvent is evaporated off and the product 9 is obtained with a yield of 99% (9.20 g, 0.014 mol). No additional purification is necessary.

Step e): Reaction of the Product Obtained in Step d) with Methyl 3,5-Dihydroxybenzoate

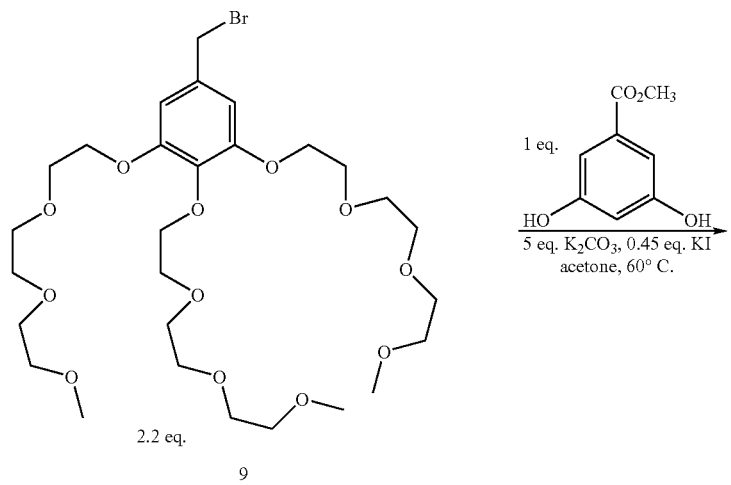

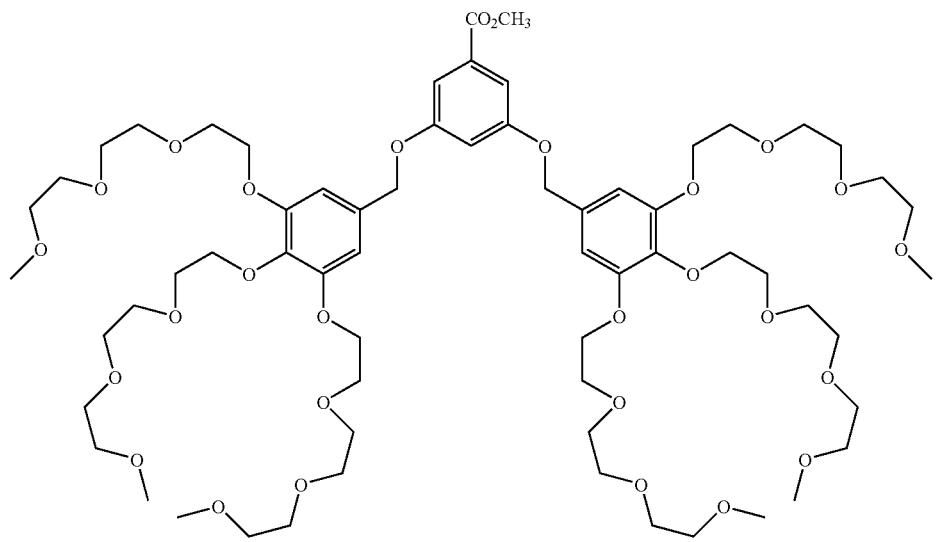

11

A solution of product 9 (3.00 g, 4.56 mmol), of methyl 3,5-dihydroxybenzoate (348 mg, 2.07 mmol), of $K_2CO_3$ (1.43 g, 10.37 mmol) and KI (15 mg, 0.93 mmol) in 50 ml of acetone is heated at 60° C. for 72 hours. The reaction medium is then cooled to ambient temperature and filtered through Celite, and the filtrate thus obtained is evaporated to dryness.

The residue is taken up in ml of $CH_2Cl_2$, and the organic phase obtained is washed with 3×0 ml of a saturated aqueous solution of NaCl, dried over anhydrous $MgSO_4$, filtered, and then evaporated to dryness so as to obtain g of crude product to be purified.

Purification: chromatography column 4.5 cm in diameter, $V_{silica}$=500 ml, eluent: $CH_2Cl_2$: acetone 1:2

The product 11 is obtained with a yield of 75% (5.00 g, 3.4 mmol). Yellowish oil.

Step f): Reduction of the Product Obtained in Step e), with $LiAlH_4$

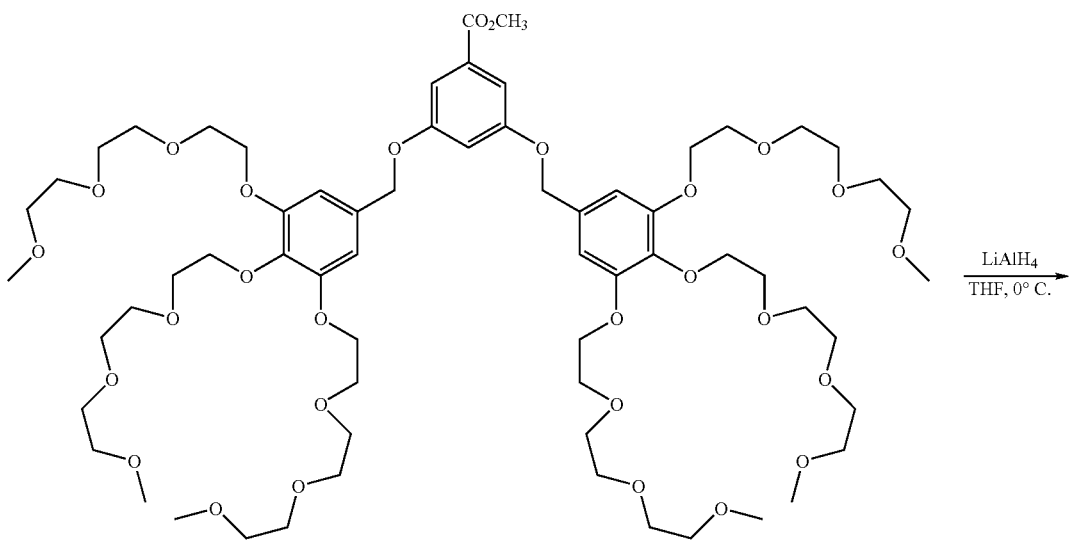

11

-continued

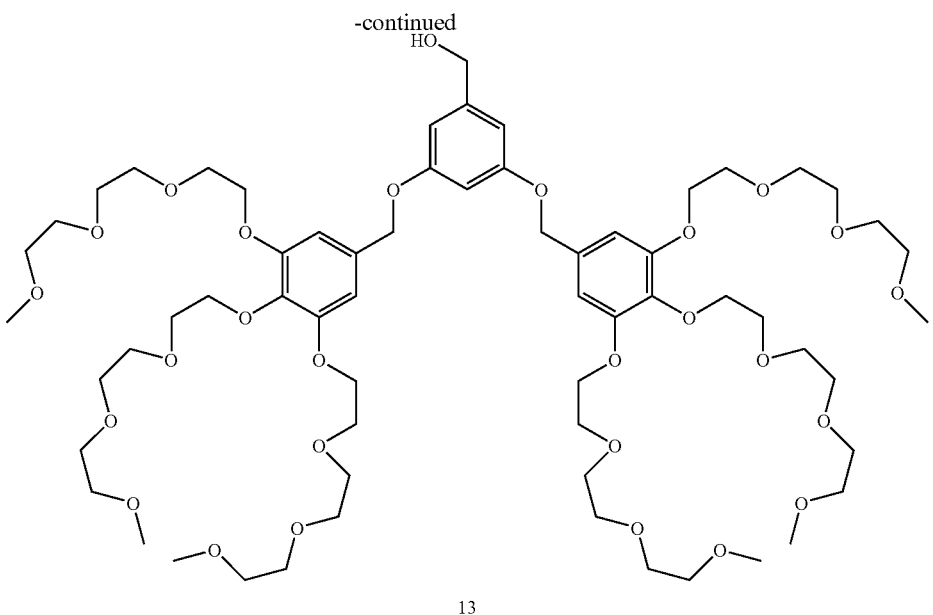

13

A 1M solution of LiAlH$_4$ in THF (6.35 ml, 6.35 mmol) is added dropwise, very carefully, to a solution of product 11 (6.00 g, 4.54 mmol) in 100 ml of anhydrous THF kept under argon and cooled to 0° C. with an ice bath. After stirring for 20 hours at ambient temperature, the reaction medium is cooled to 0° C. with an ice bath and the reaction is stopped by adding 20 ml of ethyl acetate (EtOAc), then 20 ml of methanol (MeOH) and, finally, 20 ml of water. The addition of ethyl acetate results in a violent reaction if it is not introduced slowly, the addition of water causes the salts to precipitate. The reaction medium is then filtered through Celite and then evaporated to dryness. The residue obtained is taken up in 50 ml of CH$_2$Cl$_2$, and washed with 3×50 ml of a saturated aqueous solution of NaCl. The organic phase obtained is dried over anhydrous MgSO$_4$, filtered, and evaporated to dryness. The product 13 is obtained with a yield of 78% (4.58 g, 3.54 mmol).

Step g): Reaction of the Product Obtained in Step f) with Diethylenetriaminepentaacetic Dianhydride

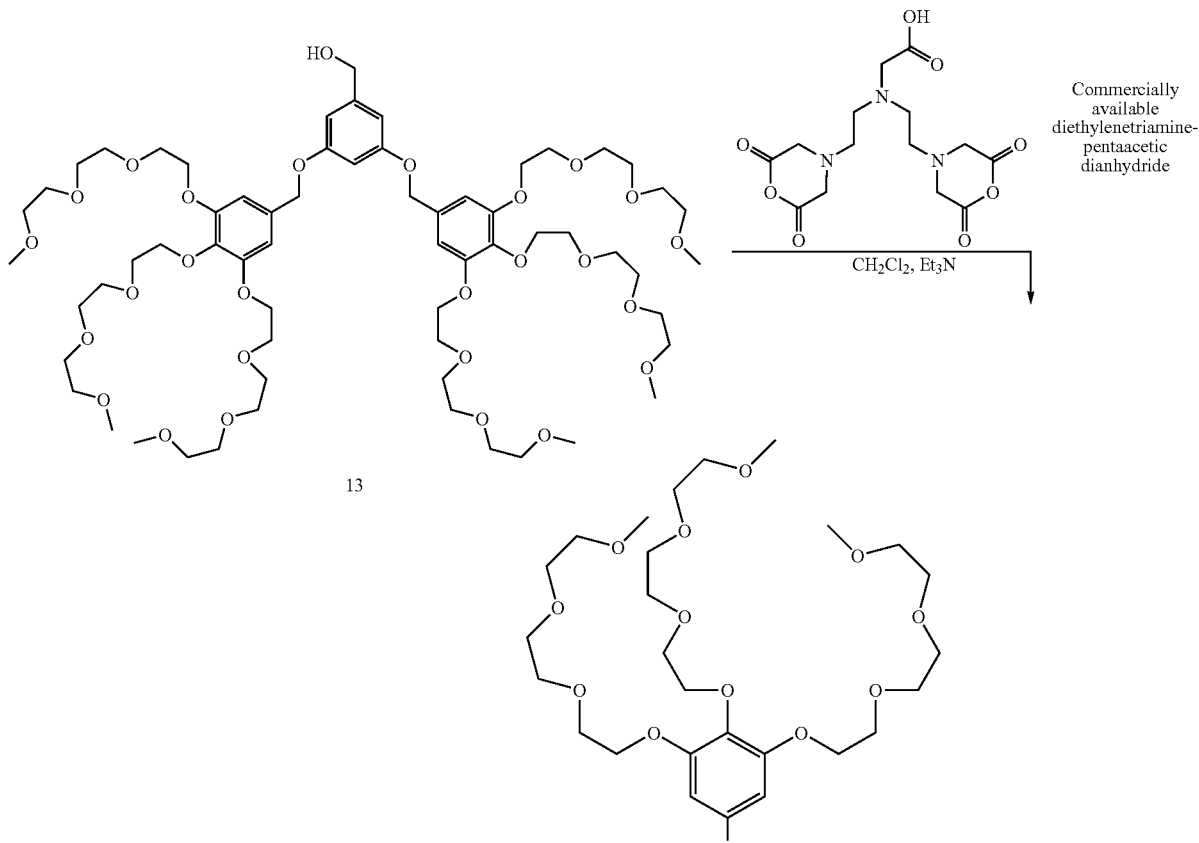

13

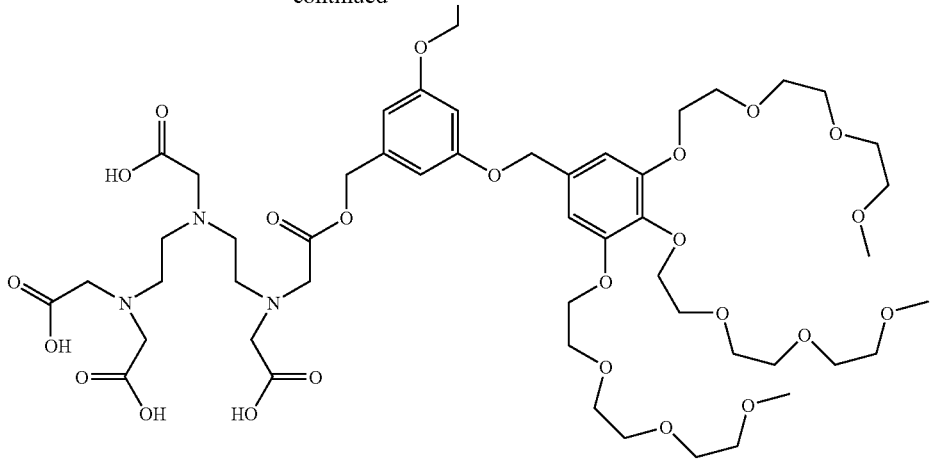

15

The diethylenetriaminepentaacetic dianhydride (63 mg, 0.177 mmol) and the product 13 (230 mg, 0.177 mmol) are solubilized in 17 ml of anhydrous methylene chloride, and the suspension obtained is stirred at 50° C. for 30 minutes. Triethylamine (0.247 ml, 1.77 mmol) is then added, and the reaction medium is stirred at 50° C. for 12 hours, before being cooled to ambient temperature, and concentrated to 5 ml. 30 ml of hexane are then added thereto, and the solution obtained is left in the fridge (+4° C.) overnight. The product that has precipitated is washed with hexane, dried under vacuum, and then purified with a flash chromatography column.

Purification: chromatography column 1 cm in diameter, $V_{silica}$=20 ml, eluent: $CH_2Cl_2$/50% MeOH The product 15 is obtained with a yield of 96% (284 mg, 0.17 mmol). Yellowish oil.

Step h) Reaction of the Product Obtained in Step g) with Gd Chloride or Mn chloride or Pertechnetate

- 1. Reaction of the product obtained in step g) with Gd chloride:

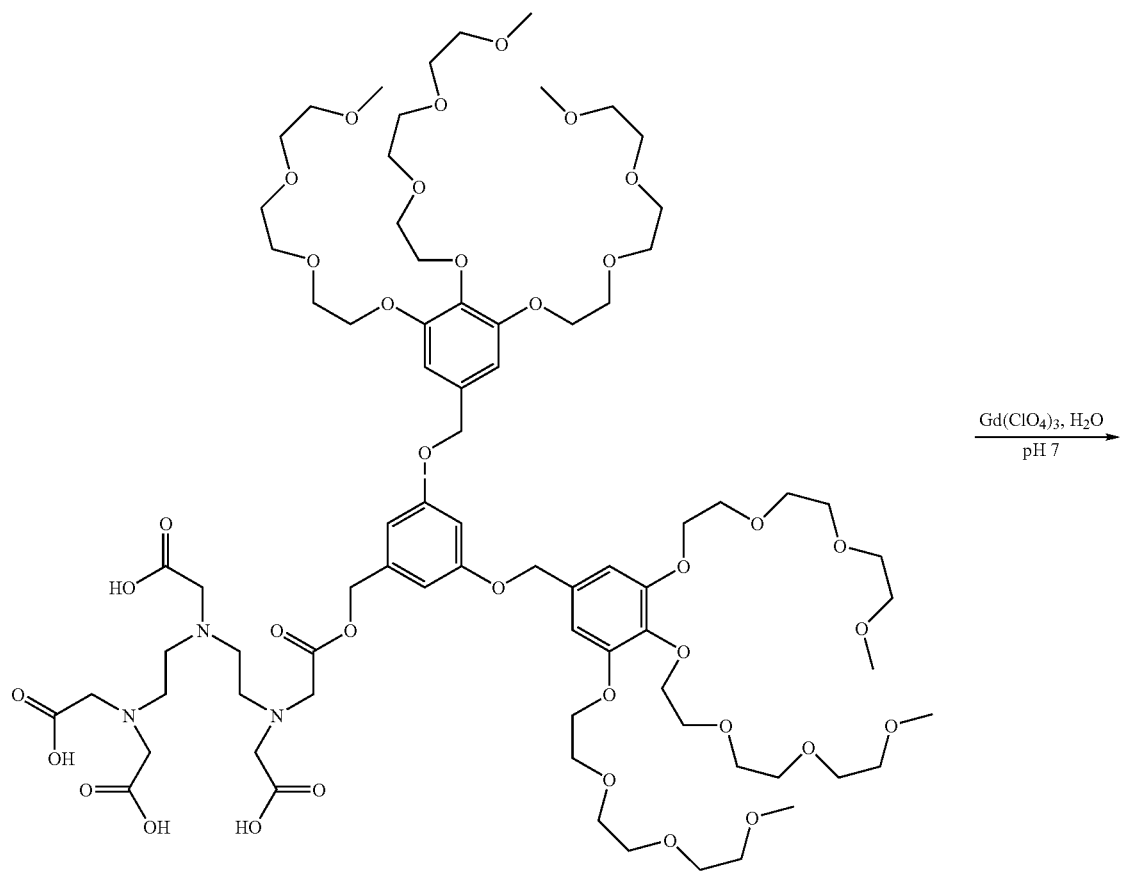

15

-continued

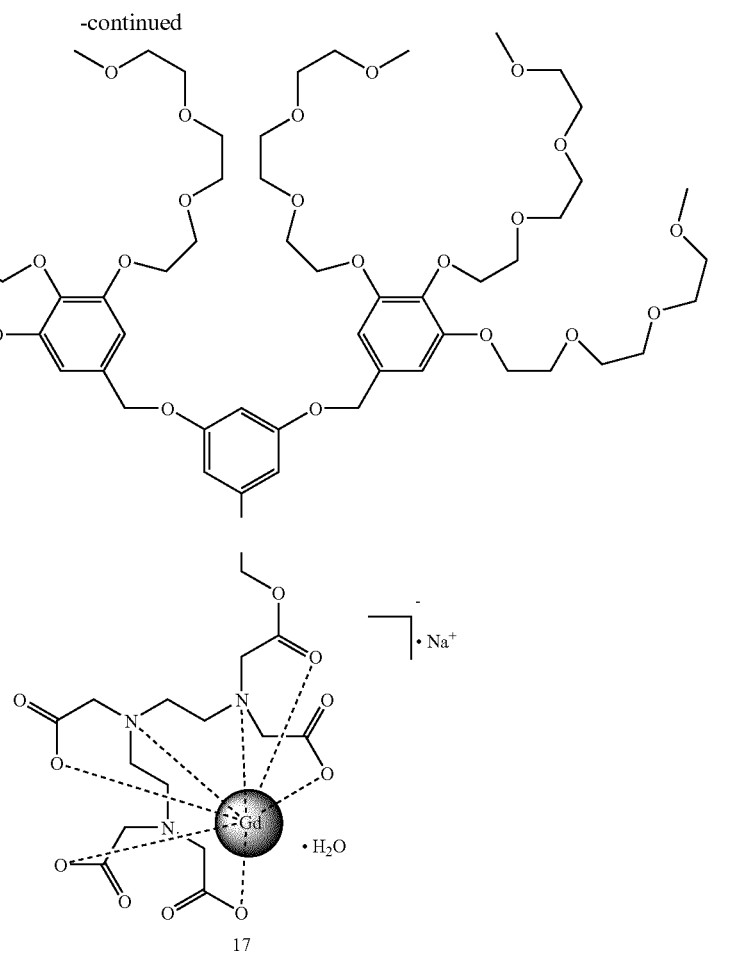

17

The ligand 15 (350 mg, 0.209 mmol) and Gd(ClO$_4$)$_3$ (191 mg of a 50% solution in water, 0.209 mmol) are dissolved in 10 ml of distilled water and the solution is stirred at ambient temperature for 12 hours while keeping the pH constant at 7 by adding a 1M solution of NaOH. The reaction medium is then treated with Chelex resin for 1 hour in order to remove the free Gd$^{3+}$ ions, and then filtered and lyophilized.

The complex 17 is obtained with a yield of 91% (351 mg, 0.19 mmol). Yellowish oil.

The complex of formula II-1 is obtained.

- 2. Reaction of the product obtained in step g) with Mn chloride:

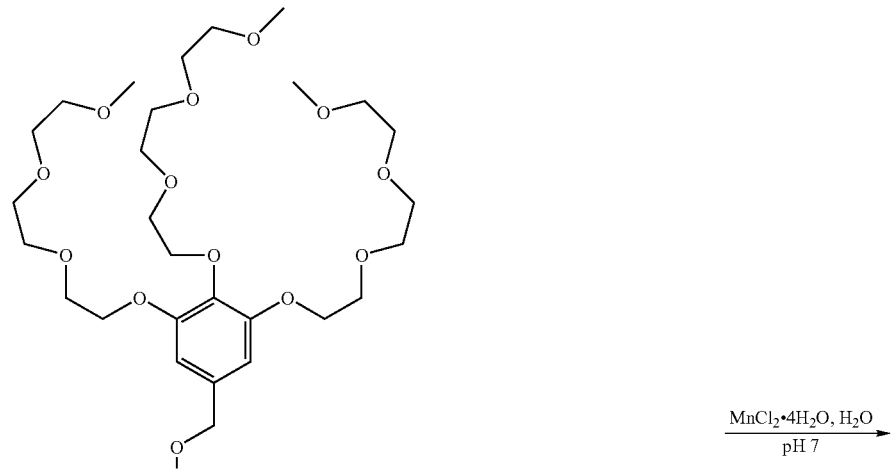

$$\xrightarrow[\text{pH 7}]{\text{MnCl}_2 \cdot 4\text{H}_2\text{O, H}_2\text{O}}$$

-continued

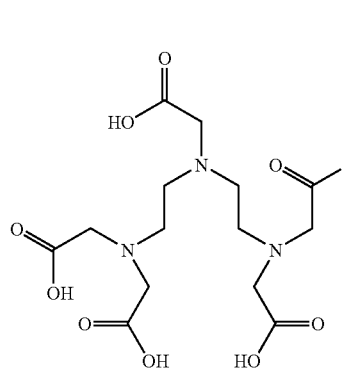
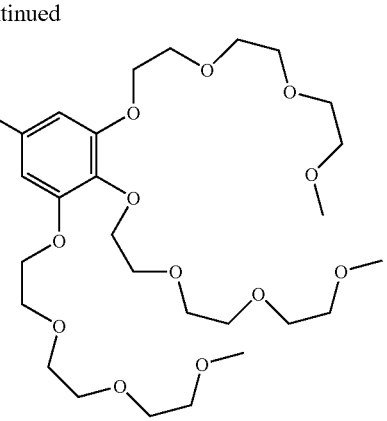

15

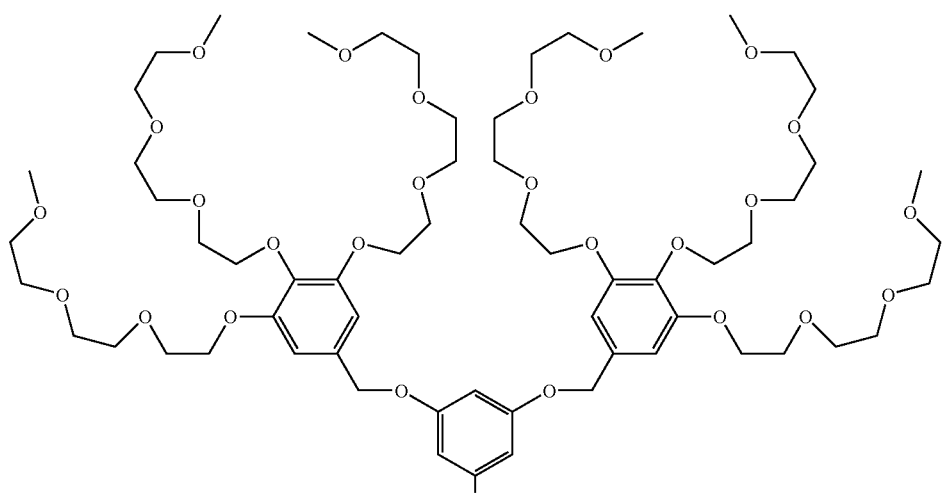

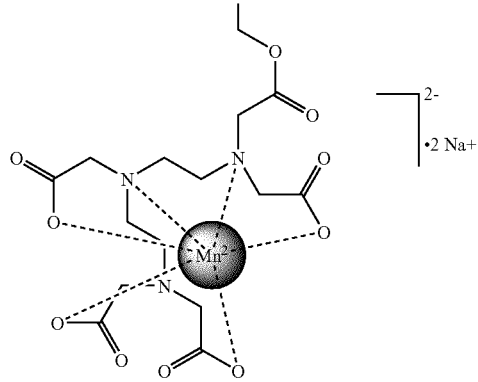

19

MnCl$_2$.4H$_2$O (37 mg, 0.185 mmol) is added to a solution of product 15 (310 mg, 0.185 mmol) in water (5 ml), stirred at ambient temperature. After stirring for 30 minutes, the impure complex 19 (presence of inorganic impurities of NaCl type) is lyophilized. A purification may be carried out in order to remove the sodium salts.

Purification: after lypophilization, the dry residue is taken up in a minimum amount of dichloromethane and the organic phase obtained is washed with a virtually saturated aqueous solution of NaCl, before being dried over anhydrous MgSO$_4$, filtered, and then evaporated to dryness.

The complex 19 is obtained with a yield of 90% (300 mg, 0.168 mmol).

The complex of formula II-2 is obtained.

- 3. Reaction of the product obtained in step g) with pertechnetate:

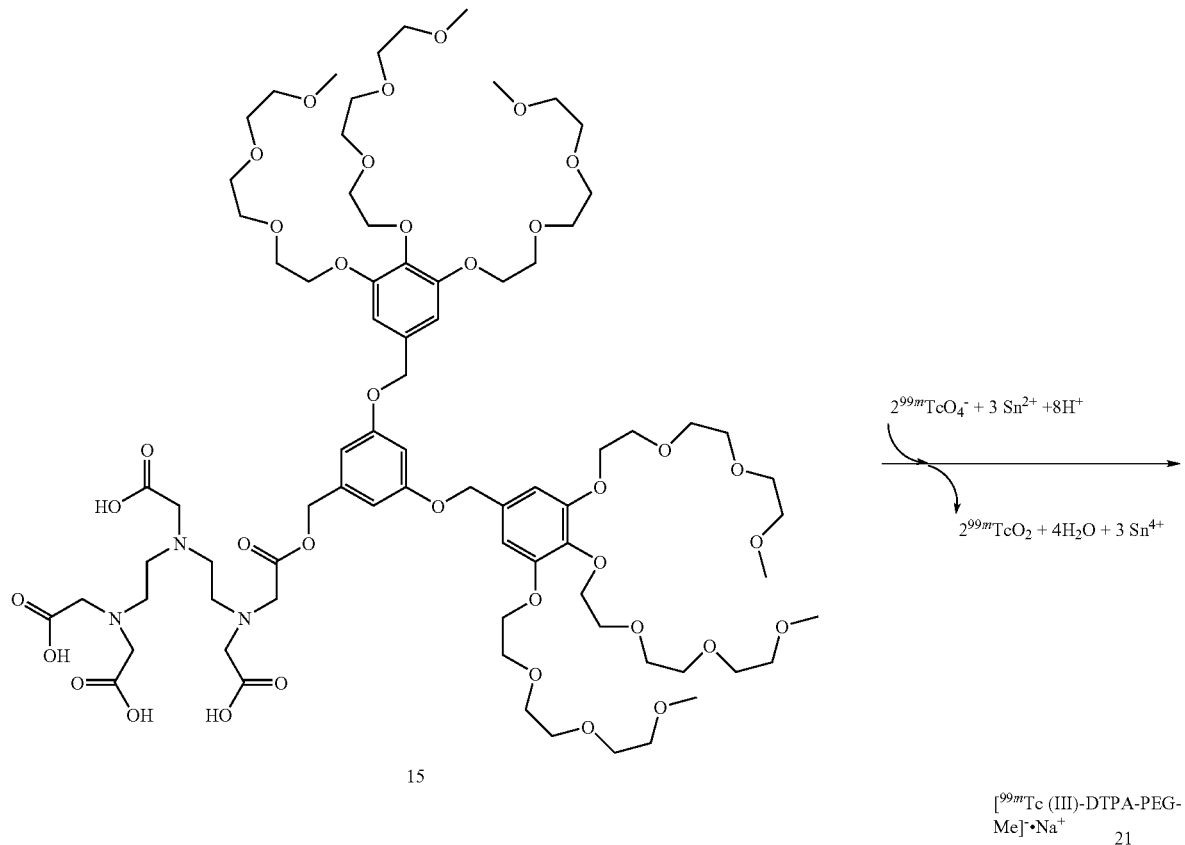

Manipulation carried out in a shielded nuclear medicine hood equipped with an activity meter:

185 MBq (5 mCi) of pertechnetate 99mTc$^{3+}$O$_4^-$ (2 to 4 ml) leaving the generator in solution in sterile, apyrogenic physiological saline are added to a vial containing 18 μmol of complex 15-CaNa$_3$ and 2 μmol of stannous chloride (Sn$^{2+}$) lyophilized from a stock solution.

The mixture is stirred gently and left to react for 2 minutes at ambient temperature.

The quality of the labeling is verified by chromatography on Whatman paper (3MM CHR) with methyl ethyl ketone as mobile phase: the labeled complex does not migrate (Rf=0) and the free pertechnetate migrates with the solvent front (Rf=1).

Under these conditions, the labeling is always greater than 98%.

The complex of formula II-3 is obtained.

EXAMPLE 2

Synthesis of the Compounds of Formulae from III-1 to III-3

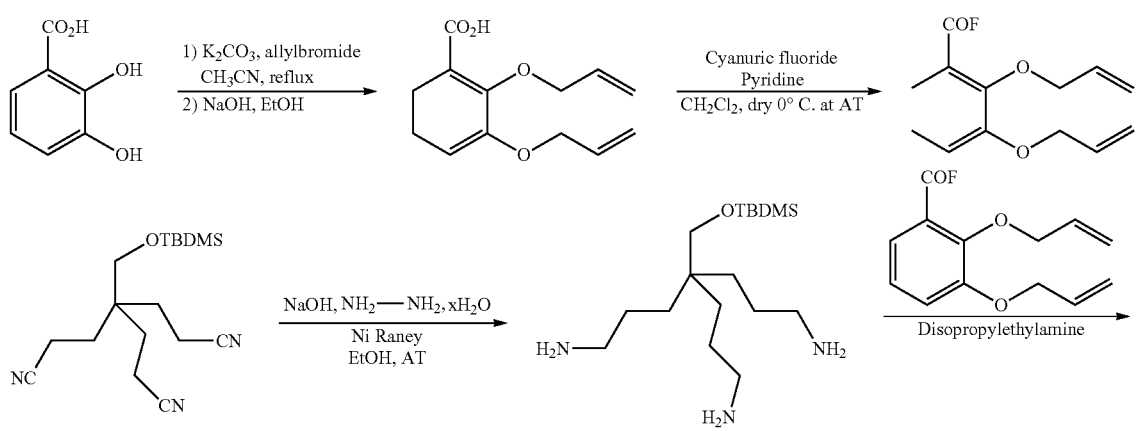

*New J. Chem.* 2000, 24, 281-288

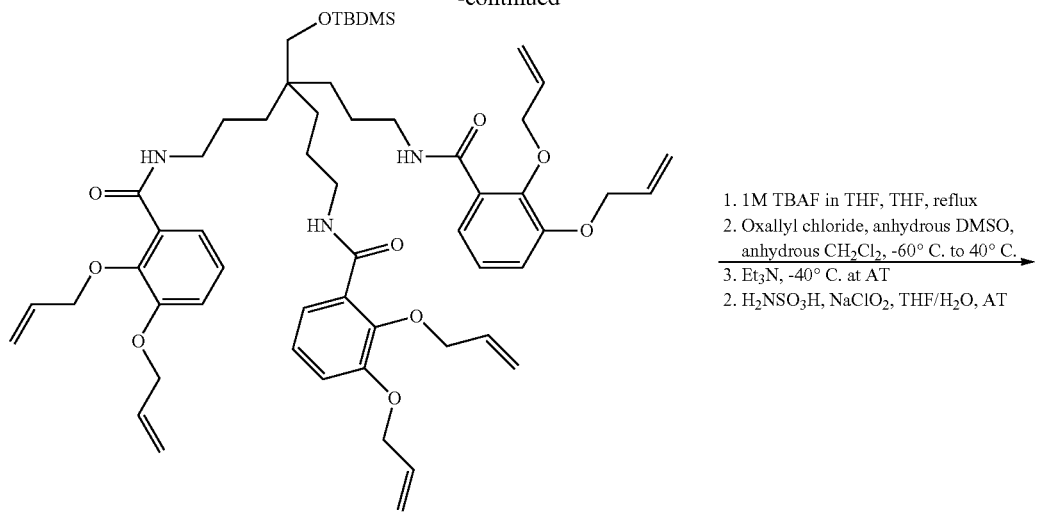
1. 1M TBAF in THF, THF, reflux
2. Oxallyl chloride, anhydrous DMSO, anhydrous CH$_2$Cl$_2$, -60° C. to 40° C.
3. Et$_3$N, -40° C. at AT
2. H$_2$NSO$_3$H, NaClO$_2$, THF/H$_2$O, AT
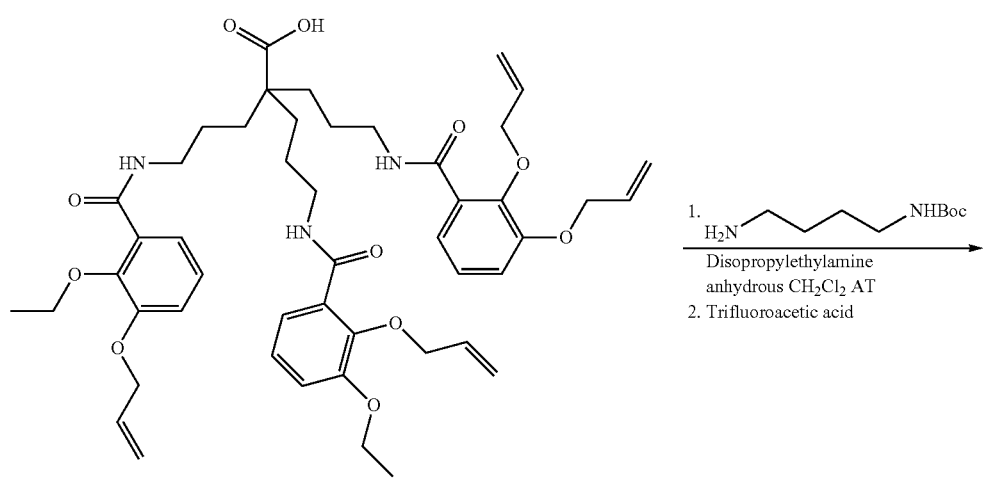
1. H$_2$N~~~~NHBoc
Disopropylethylamine
anhydrous CH$_2$Cl$_2$ AT
2. Trifluoroacetic acid
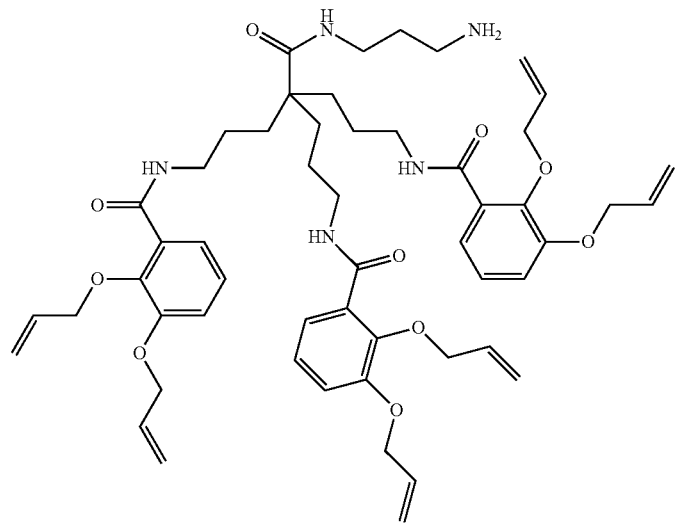

-continued
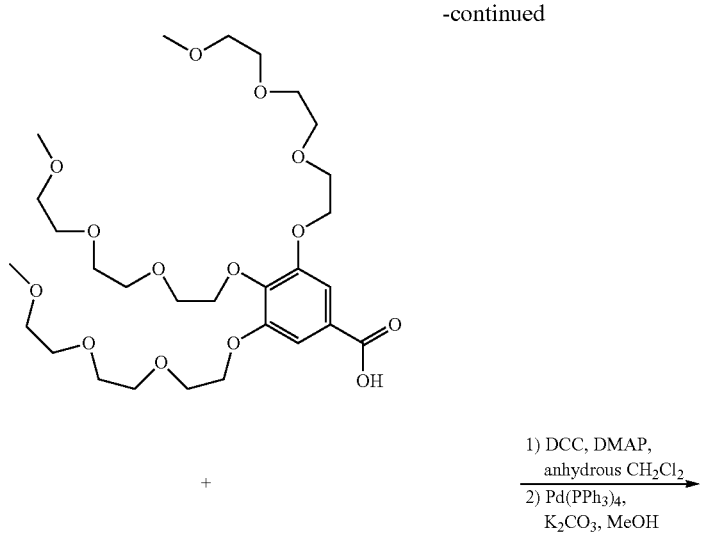
1) DCC, DMAP, anhydrous CH$_2$Cl$_2$
2) Pd(PPh$_3$)$_4$, K$_2$CO$_3$, MeOH
+
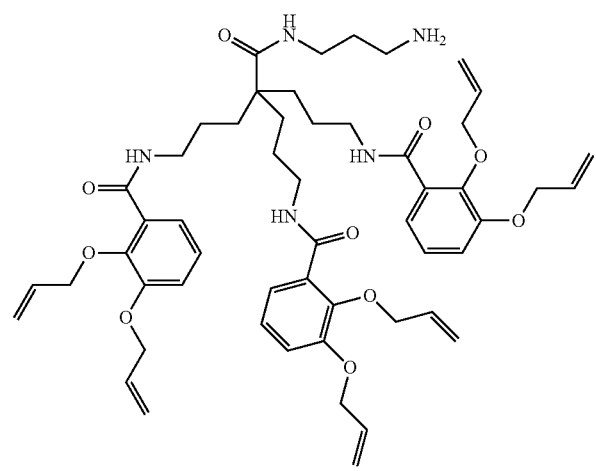
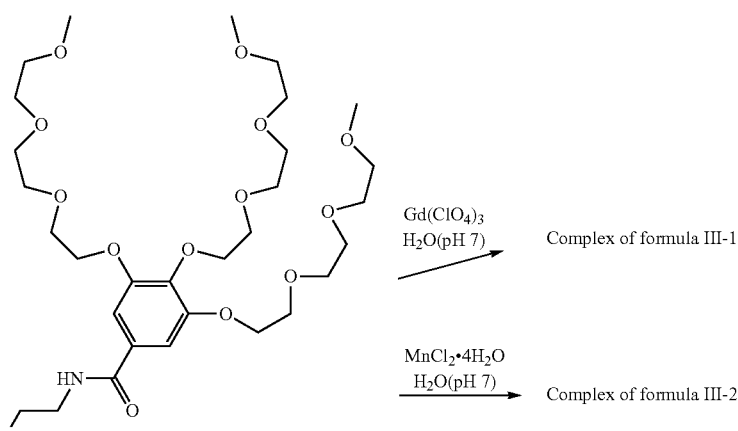
Gd(ClO$_4$)$_3$
H$_2$O(pH 7) → Complex of formula III-1
MnCl$_2$·4H$_2$O
H$_2$O(pH 7) → Complex of formula III-2

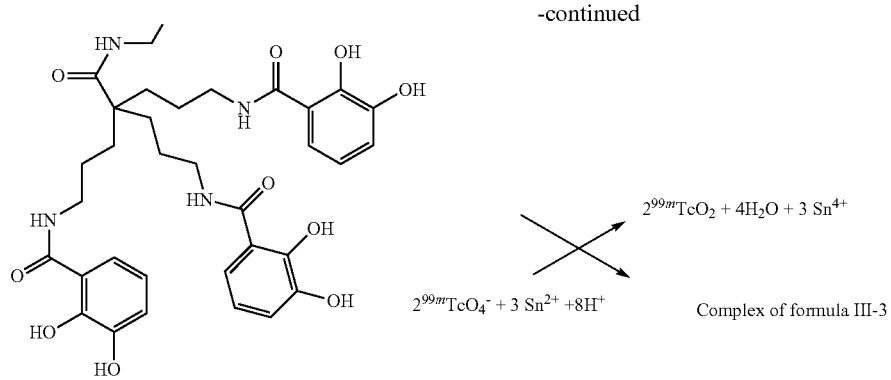
EXAMPLE 3
Synthesis of the Compounds of Formulae from IV-1 to IV-3
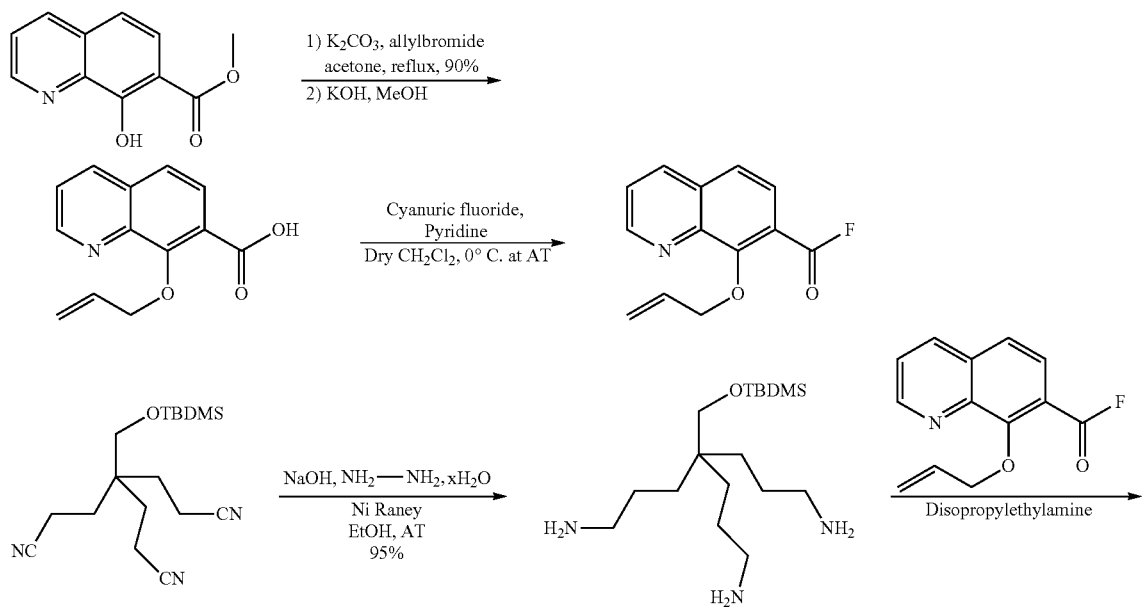
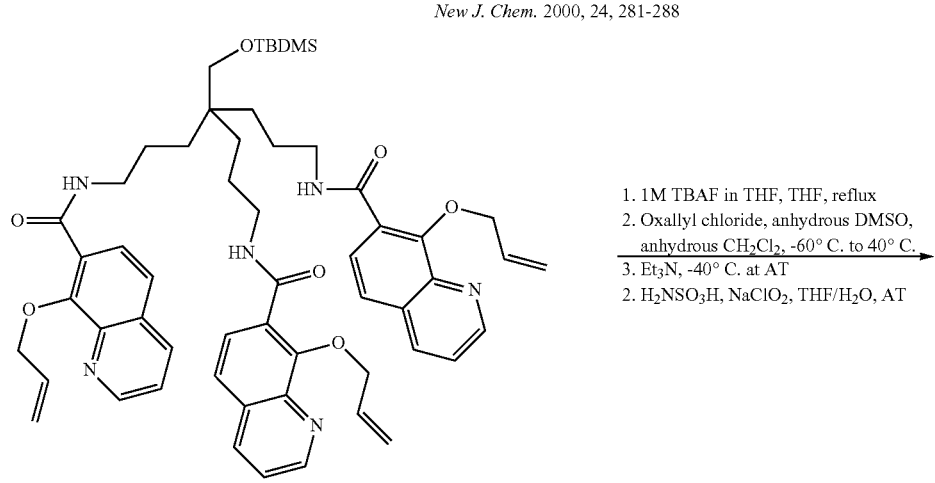

-continued
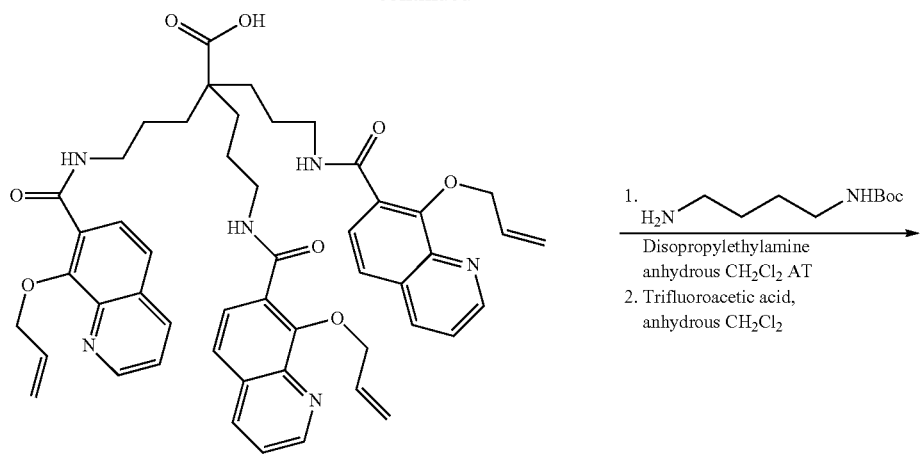
1. H₂N~~~NHBoc
   Diisopropylethylamine
   anhydrous CH₂Cl₂ AT
2. Trifluoroacetic acid,
   anhydrous CH₂Cl₂
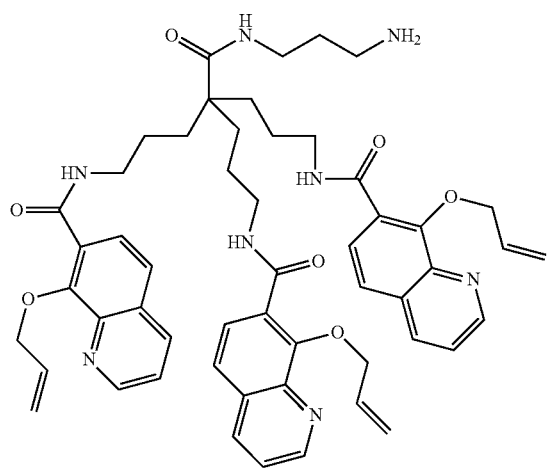
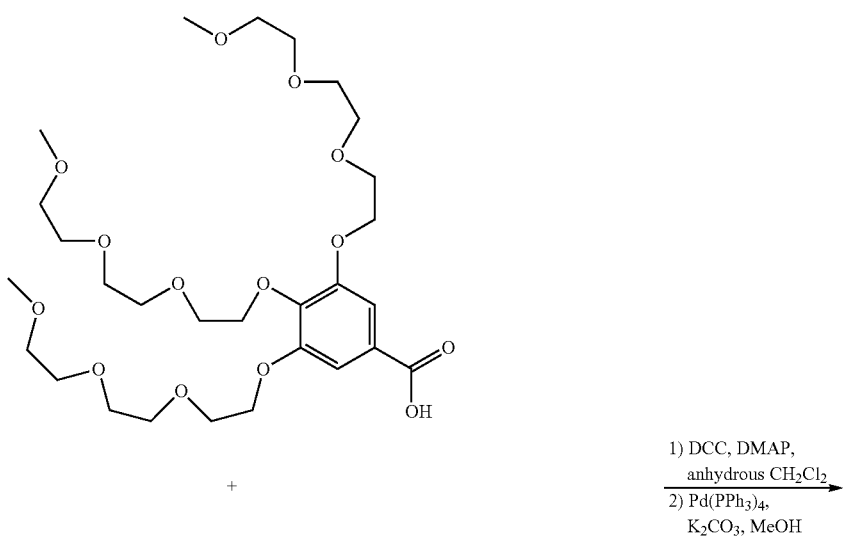
+
1) DCC, DMAP,
   anhydrous CH₂Cl₂
2) Pd(PPh₃)₄,
   K₂CO₃, MeOH -continued
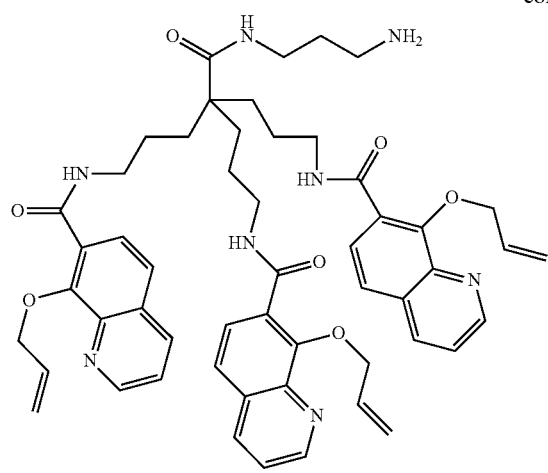
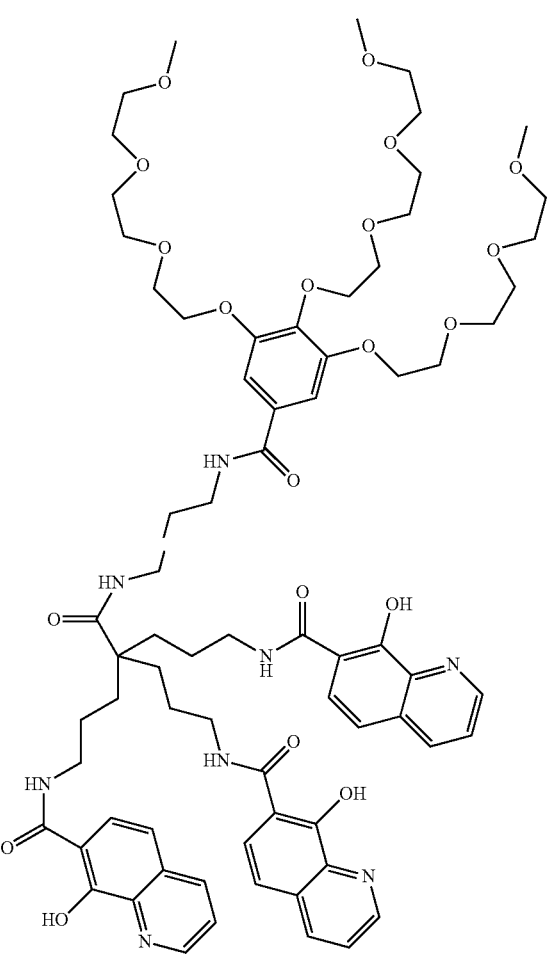
Gd(ClO₄)₃ / MnCl₂·4H₂O / $2^{99m}TcO_2 + 4H_2O + 3\ Sn^{4+}$
H₂O(pH 7) / H₂O(pH 7)
$2^{99m}TcO_4^- + 3\ Sn^{2+} + 8H^+$
Complex of formula IV-1   Complex of formula IV-2   Complex of formula IV-3

EXAMPLE 4
Synthesis of the Compounds of Formulae from V-1 to V-3
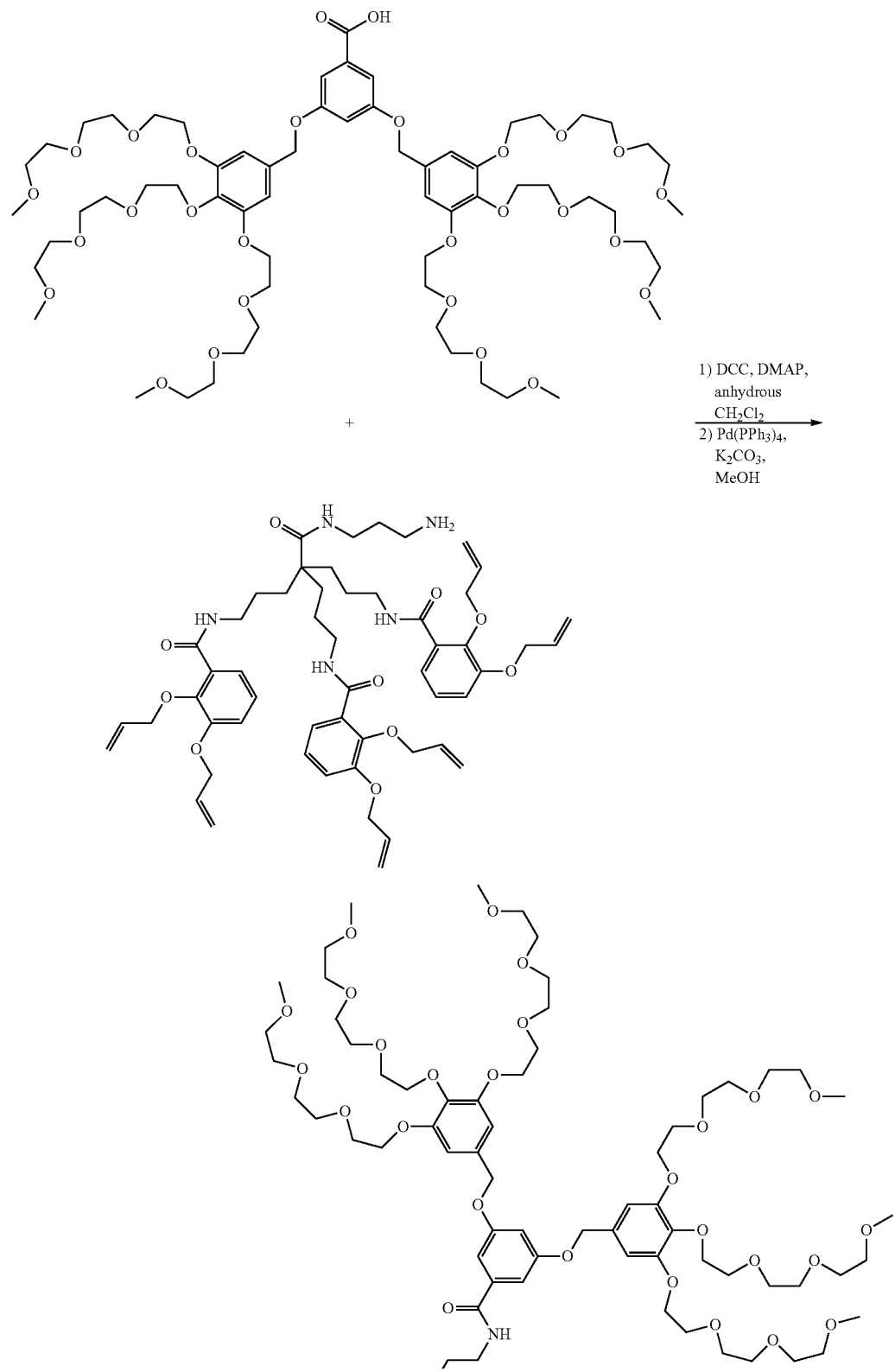

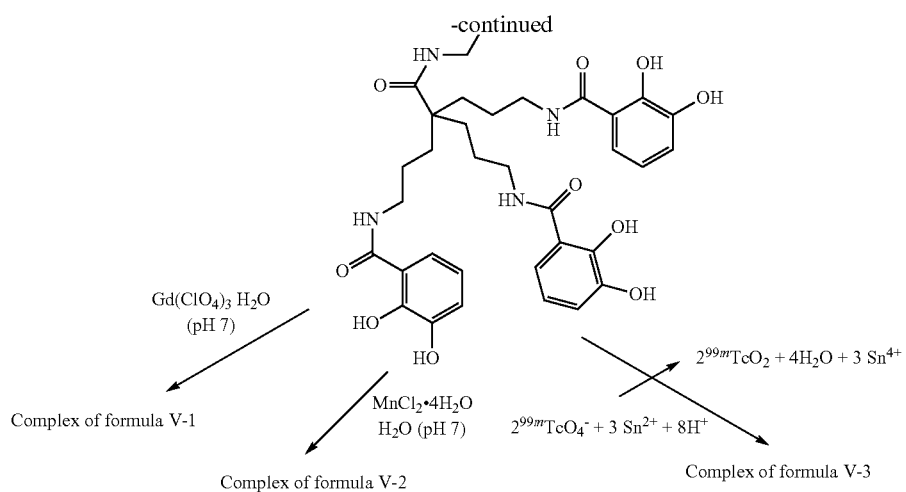
Complex of formula V-1 (Gd(ClO$_4$)$_3$ H$_2$O, pH 7)
Complex of formula V-2 (MnCl$_2$·4H$_2$O, H$_2$O (pH 7))
Complex of formula V-3 ($2^{99m}$TcO$_4^-$ + 3 Sn$^{2+}$ + 8H$^+$ → $2^{99m}$TcO$_2$ + 4H$_2$O + 3 Sn$^{4+}$)
EXAMPLE 5
Synthesis of the Compounds of Formulae from VI-1 to VI-3
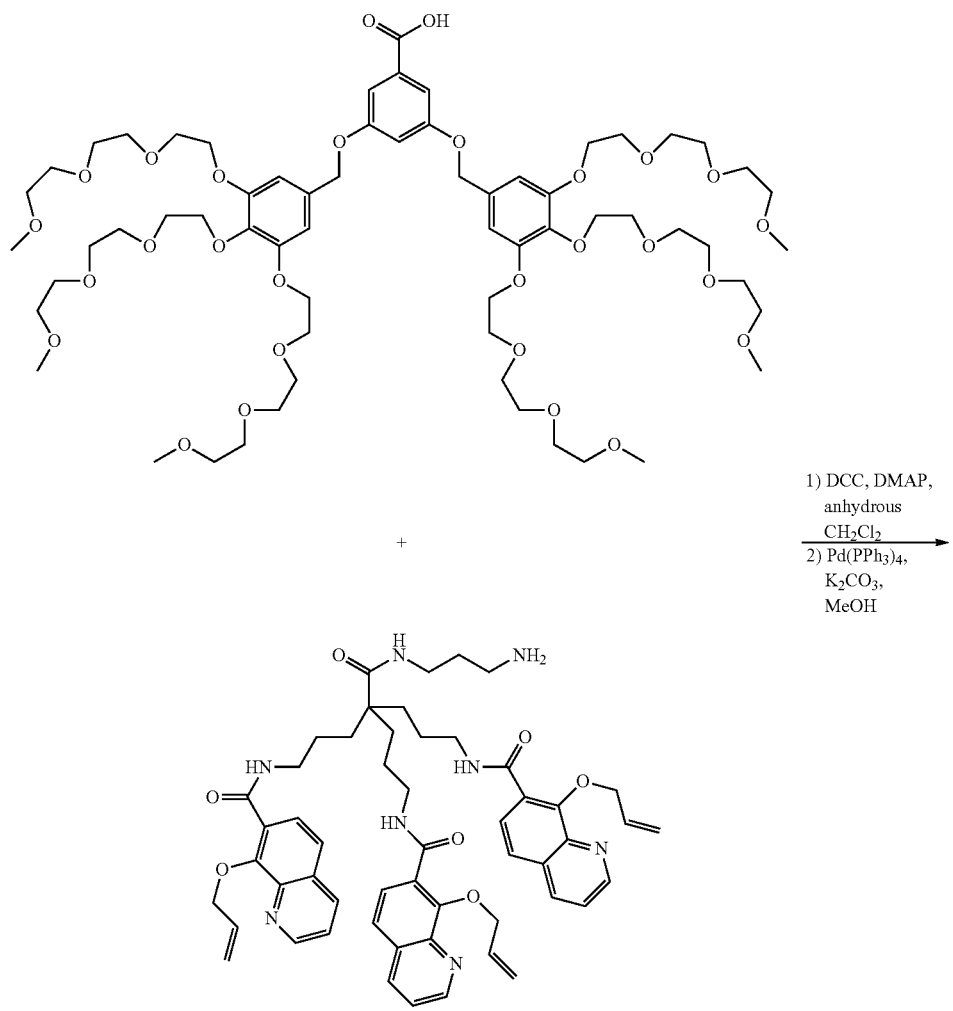
1) DCC, DMAP, anhydrous CH$_2$Cl$_2$
2) Pd(PPh$_3$)$_4$, K$_2$CO$_3$, MeOH -continued
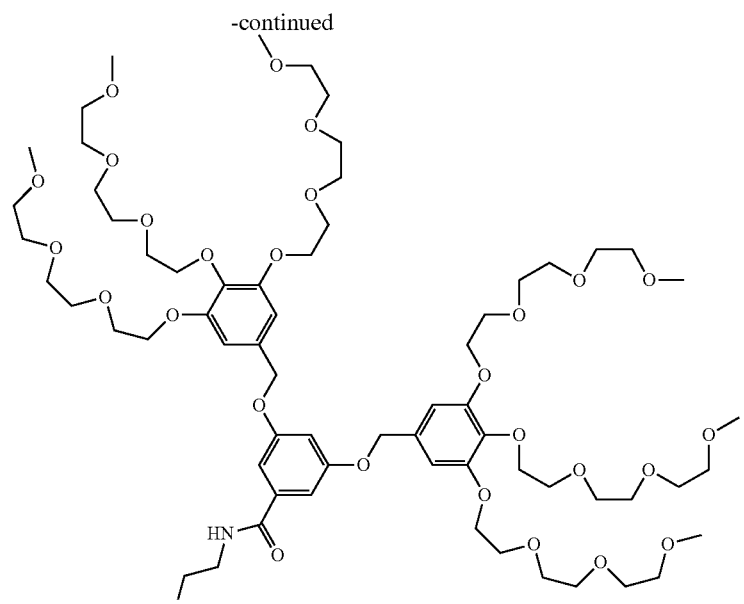
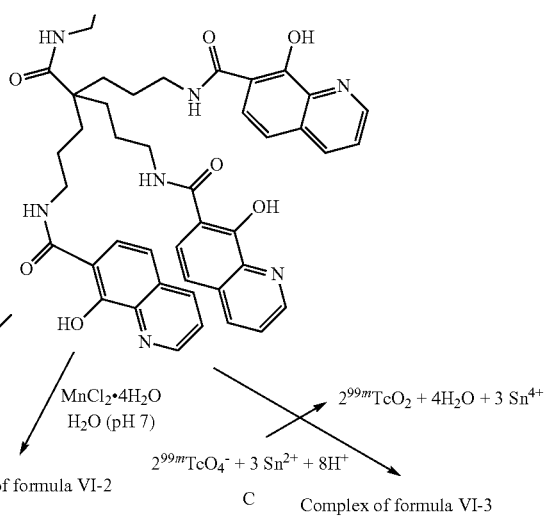
50
EXAMPLE 6
Synthesis of the Compounds of Formulae from VII-1 to VII-3
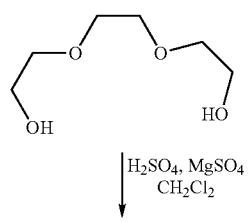

-continued
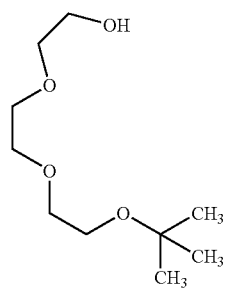 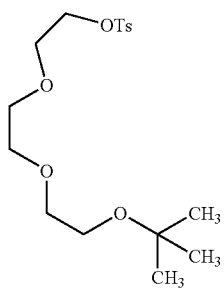 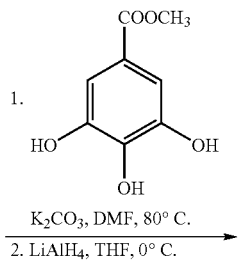
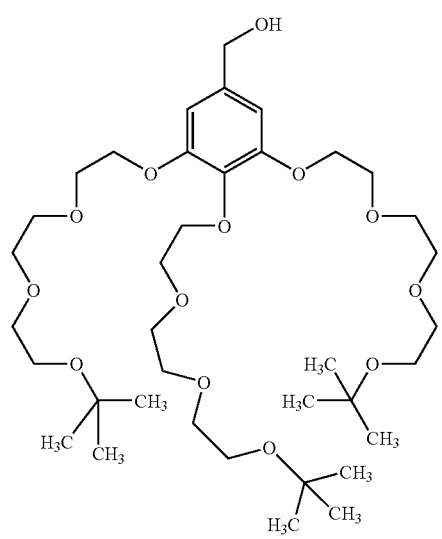 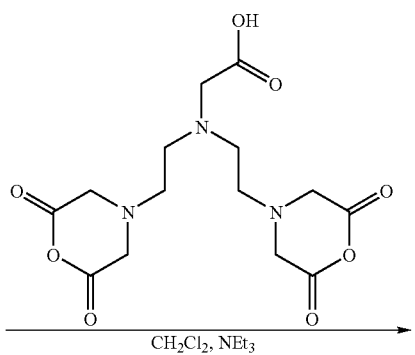
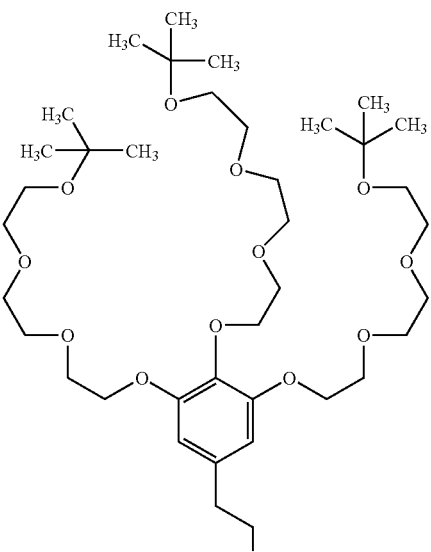

-continued

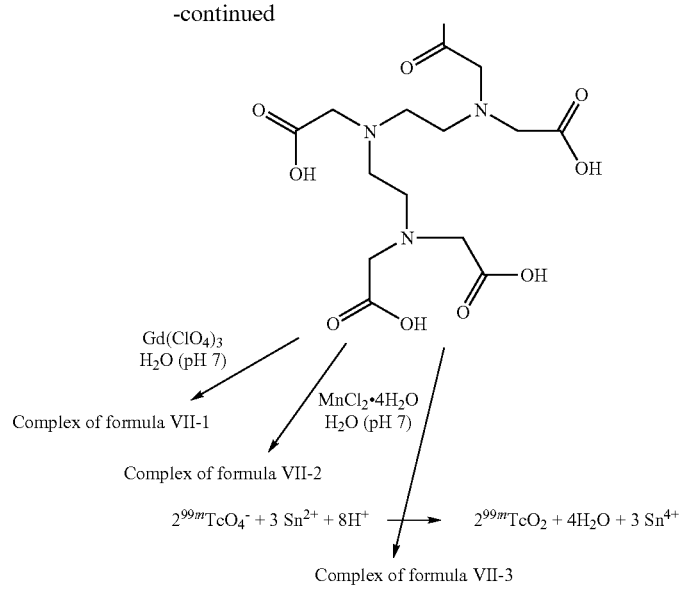

Complex of formula VII-1

Complex of formula VII-2

$2^{99m}TcO_4^- + 3\ Sn^{2+} + 8H^+ \longrightarrow 2^{99m}TcO_2 + 4H_2O + 3\ Sn^{4+}$ Complex of formula VII-3

Step a): Synthesis of Tert-Butoxytriethylene Glycol from Tert-Butanol

Step b): Reaction of the Product Obtained in Step a) with Tosyl Chloride

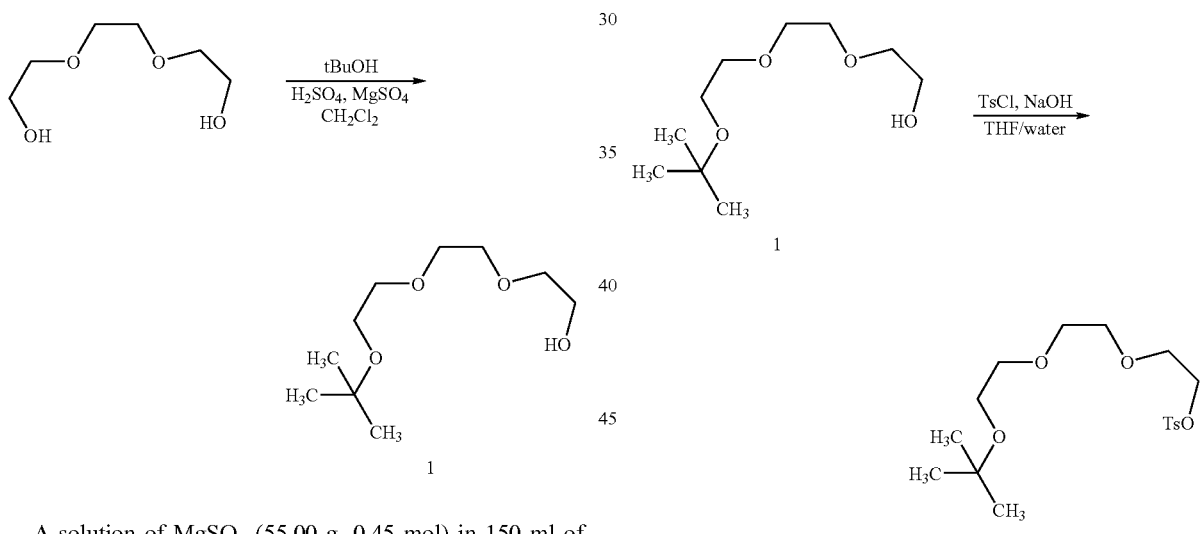

A solution of MgSO₄ (55.00 g, 0.45 mol) in 150 ml of dichloromethane is introduced into a two-necked round-bottomed flask equipped with a bulb condenser and stirred at ambient temperature. The assembly must imperatively be hermetically closed and under argon. Sulfuric acid H₂SO₄ (6.42 ml, 0.111 mol), triethylene glycol (15.00 ml, 0.111 mol) and then, very slowly, tert-butanol (52.80 ml, 0.556 mol) are then respectively introduced. The reaction medium is then stirred at ambient temperature for 19 hours and then refluxed for 2 hours. It is subsequently filtered and the organic phase is washed with water (300 ml) and then with a saturated aqueous solution of NaCl (2×300 ml), before being dried over anhydrous MgSO₄, filtered, and then evaporated to dryness.

Purification: chromatography column 3.5 cm in diameter, $V_{silica}$=400 ml, eluent: 95/5 CH₂Cl₂/MeOH The product 1 is obtained with a yield of 23% (5.29 g, 0.026 mol).

Tosyl chloride (1.85 g, 9.70 mmol) dissolved in 4 ml of THF is added dropwise to a solution of NaOH (0.53 g, 13.23 mmol) and of alcohol 1 (1.82 g, 8.82 mmol) in a water/THF mixture (2/14 ml) cooled to 0° C. After stirring for 68 hours at ambient temperature, the reaction medium is poured into 50 ml of a saturated aqueous solution of NaCl cooled to 0° C. The organic phase obtained is washed with a saturated aqueous solution of NaCl (100 ml), dried over anhydrous MgSO₄, filtered, and evaporated to dryness.

Purification: chromatography column 3.5 cm in diameter, $V_{silica}$=400 ml, eluent: CH₂Cl₂/MeOH 98:2

The product 2 is obtained with a yield of 67% (0.87 g, 5.89 mmol).

Step c): Reaction of the Tosylate Obtained in Step b) with Methyl 3,4,5-Trihydroxybenzoate

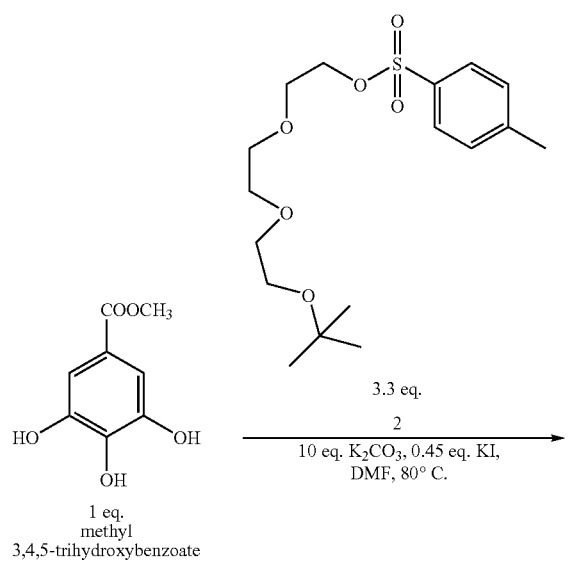

Step d): Reduction of the Product Obtained in Step c), Preferably with LiAlH₄, so as to Obtain the Corresponding Alcohol

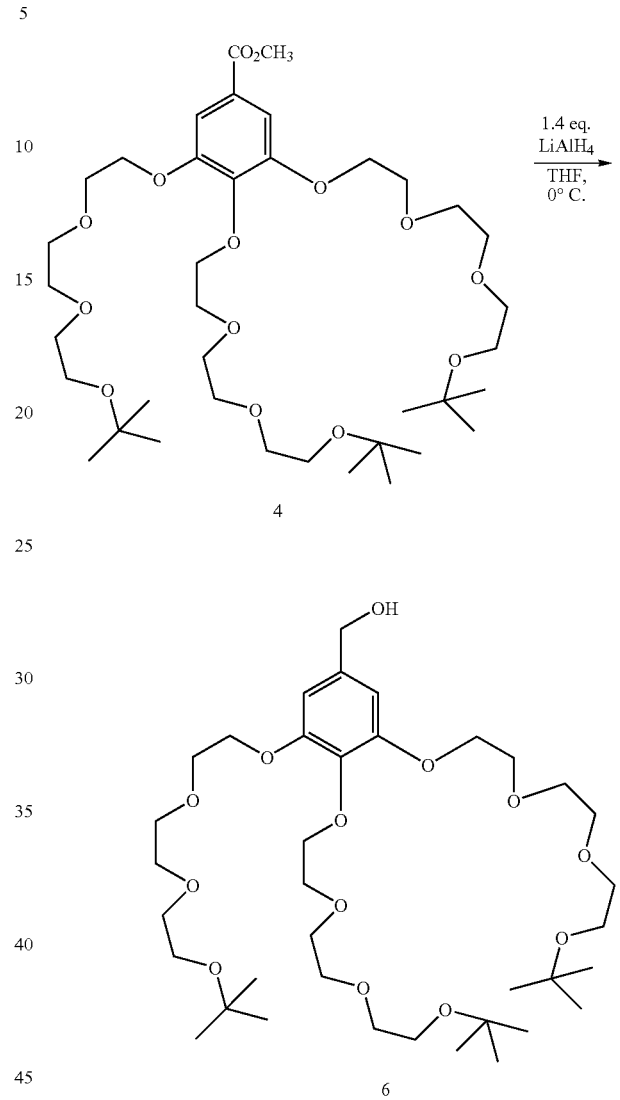

A solution of tosylate 2 (5.89 g, 16.28 mmol), of methyl 3,4,5-trihydroxybenzoate (0.91 g, 4.93 mmol), of $K_2CO_3$ (6.82 g, 0.163 mol) and of KI (0.37 g, 2.22 mmol) in dimethylformamide (DMF) (20 ml) is stirred and heated at 80° C., using an oil bath, for 72 hours.

After having stopped the heating, the reaction medium is cooled to ambient temperature and then filtered through Celite. After evaporation of the solvent, the residue of the filtrate is taken up in 300 ml of $CH_2Cl_2$. The organic phase thus obtained is washed with 3×300 ml of a saturated aqueous solution of NaCl, dried over anhydrous $MgSO_4$, then filtered, and evaporated to dryness so as to give 4.60 g of crude product to be purified.

Purification: chromatography column 4.0 cm in diameter, $V_{silica}$=400 ml, eluent: 98/2 $CH_2Cl_2$/MeOH The product 4 is obtained with a yield of 82% (2.96 g, 4.03 mmol).

A 1M solution of LiAlH₄ in THF (6.64 ml, 6.64 mmol) is added dropwise, very carefully, to a solution of product 4 (2.96 g, 4.03 mmol) in 4 ml of anhydrous THF kept under argon and cooled to 0° C. with an ice bath. After stirring for 20 hours at ambient temperature, the reaction medium is cooled to 0° C. with an ice bath and the reaction is stopped by adding 4 ml of ethyl acetate (EtOAc), then 4 ml of methanol (MeOH) and, finally, 4 ml of water. The addition of ethyl acetate results in a violent reaction if it is not introduced slowly, the addition of water causes the salts to precipitate. The reaction medium is then filtered through Celite and then evaporated to dryness. The residue obtained is taken up in 35 ml of $CH_2Cl_2$, and washed with 3×35 ml of a saturated aqueous solution of NaCl. The organic phase obtained is dried over anhydrous $MgSO_4$, filtered, and evaporated to dryness.

The product 6 is obtained with a yield of 88% (2.56 g, 3.55 mmol).

Step e): Reaction of the Product Obtained in Step d) with Diethylenetriaminepentaacetic Dianhydride

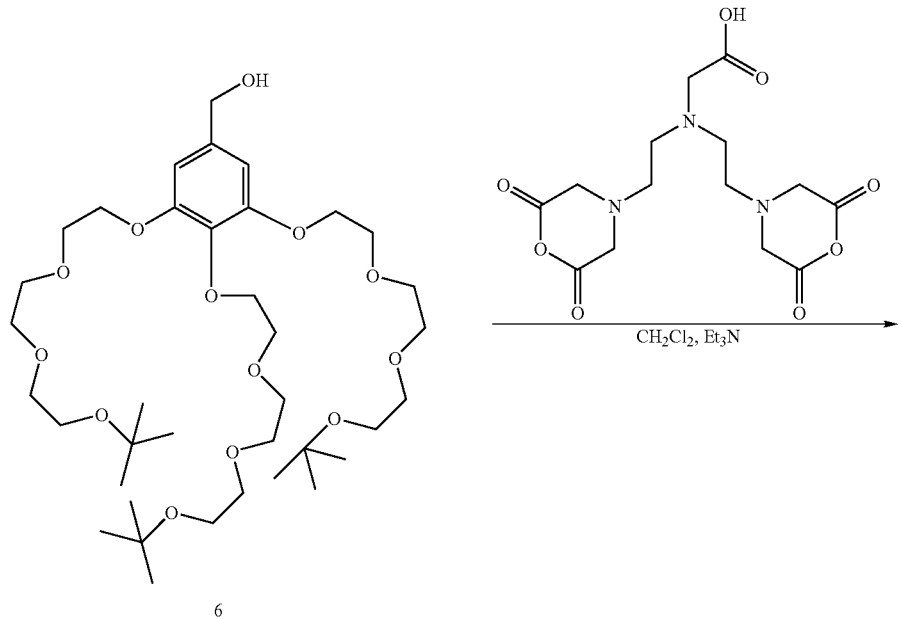

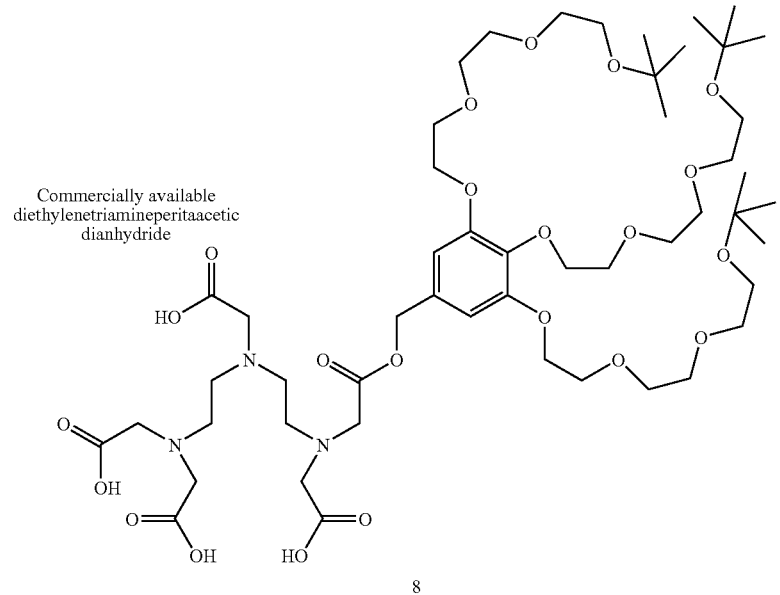

The diethylenetriaminepentaacetic dianhydride (1.23 g, 3.46 mmol) and the product 6 (2.50 g, 3.46 mmol) are solubilized in 50 ml of anhydrous methylene chloride, and the suspension obtained is stirred at 50° C. for 30 minutes. Triethylamine (4.82 ml, 34.6 mmol) is then added, and the reaction medium is stirred at 50° C. for 12 hours, before being cooled to ambient temperature and concentrated to 5 ml. 30 ml of hexane are then added thereto, and the solution obtained is left in the fridge (+4° C.) overnight. The product that has precipitated is washed with hexane, dried under vacuum, and then purified with a flash chromatography column.

Purification: chromatography column 1 cm in diameter, $V_{silica}$=20 ml, eluent: $CH_2Cl_2$/50% MeOH The product 8 is obtained with a yield of 95% (3.59 g, 3.28 mmol). Yellowish oil.

Step f): Reaction of the Product Obtained in Step e) with Gd Chloride or Mn Chloride or Pertechnetate
1. Reaction with Gd chloride
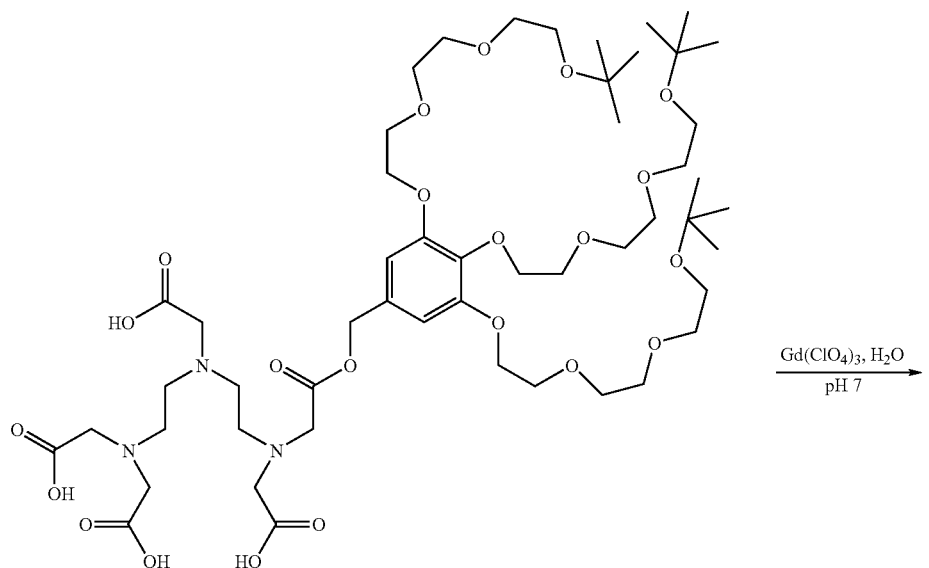
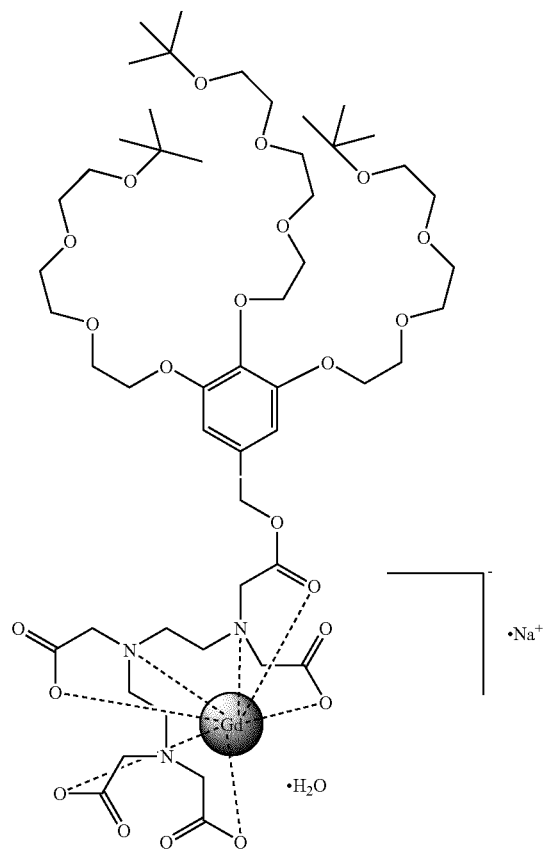

The ligand 8 (1.00 g, 0.91 mmol) and Gd(ClO$_4$)$_3$ (838 mg of a 50% solution in water, 0.91 mmol) are dissolved in 5 ml of distilled water, and the solution is stirred at ambient temperature for 12 hours while keeping the pH constant at 7 by adding a 1M solution of NaOH. The reaction medium is then treated with Chelex resin for 1 hour in order to remove the free Gd$^{3+}$ ions, and then filtered and lyophilized.

The complex 12 is obtained with a yield of 92% (1.07 g, 0.83 mmol). Yellowish oil.

The complex of formula VII-1 is obtained.

2. Reaction with Mn chloride

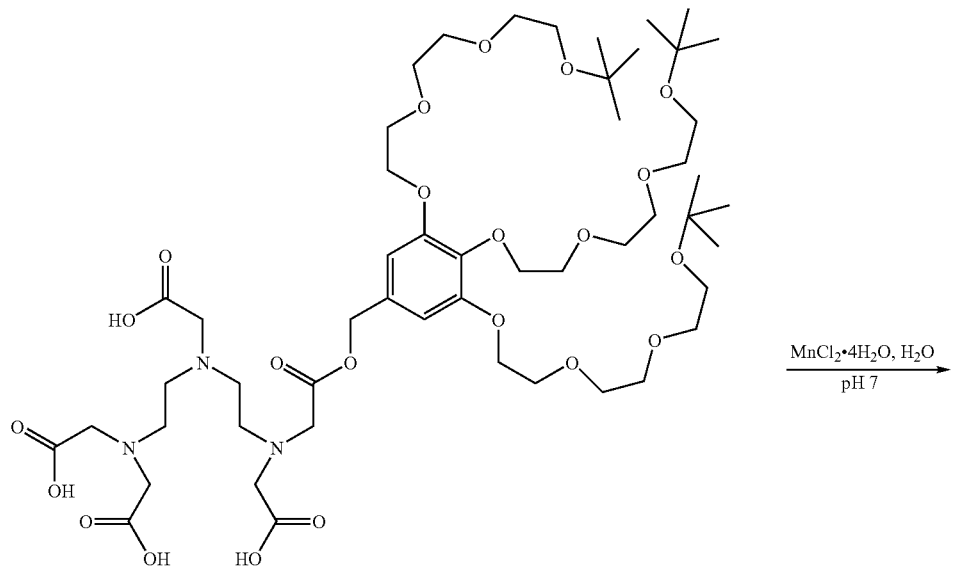

8

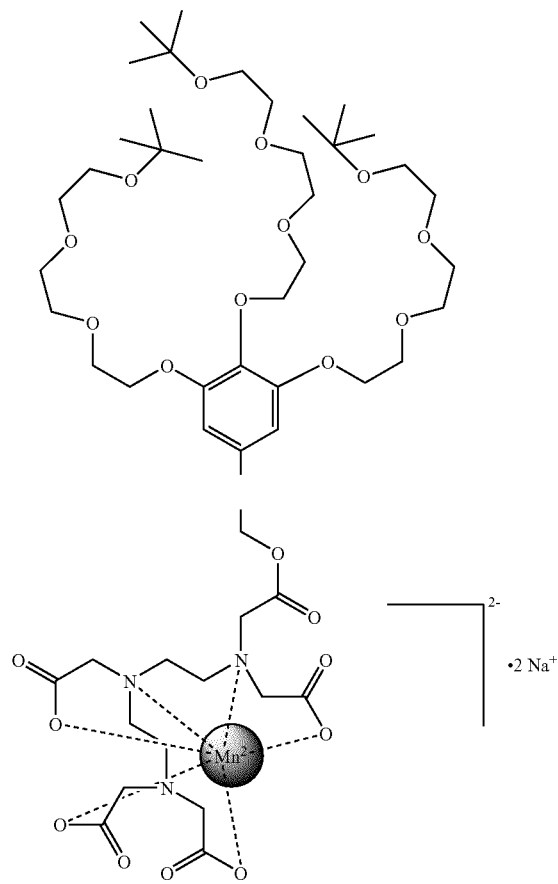

14

MnCl$_2$.4H$_2$O (182 mg, 0.91 mmol) is added to a solution of ligand 8 (1.00 g, 0.91 mmol) in water (25 ml), stirred at ambient temperature. After stirring for 30 minutes, the impure complex (presence of inorganic impurities of NaCl type) is lyophilized. A purification may be carried out in order to remove the sodium salts.

Purification: after lyophilization, the dry residue is taken up in a minimum amount of dichloromethane, and the organic phase obtained is washed with a virtually saturated aqueous solution of NaCl, before being dried over anhydrous MgSO$_4$, filtered, and then evaporated to dryness.

The compound 14 is obtained with a yield of 90% (978 mg, 0.82 mmol).

The complex of formula VII-2 is obtained.

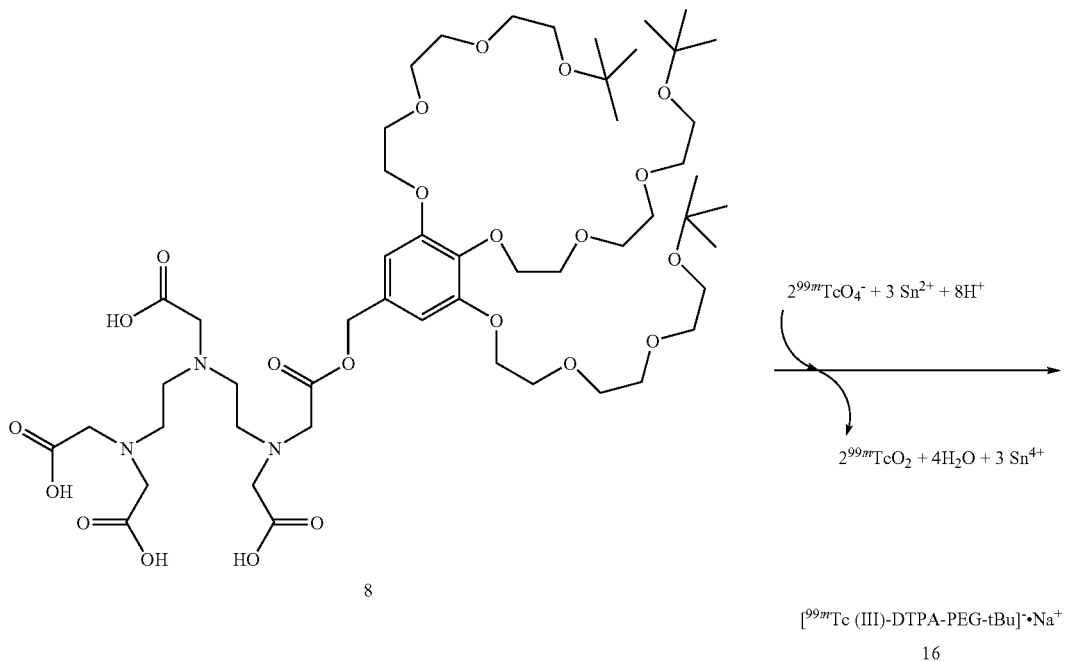

Manipulation carried out in a shielded nuclear medicine hood equipped with an activity meter:

185 MBq (5 mCi) of pertechnetate 99mTc$^{3+}$O$_4^-$ (2 to 4 ml) leaving the generator in solution in sterile, apyrogenic physiological saline are added to a vial containing 18 μmol of ligand 8-CaNa$_3$ and 2 μmol of stannous chloride (Sn$^{2+}$) lyophilized from a stock solution.

The mixture is stirred gently and left to react for 2 minutes at ambient temperature.

The quality of the labeling is verified by chromatography on Whatman paper (3MM CHR) with methyl ethyl ketone as mobile phase: the labeled complex does not migrate (Rf=0) and the free pertechnetate migrates with the solvent front (Rf=1).

Under these conditions, the labeling is always greater than 98%.

The complex of formula VII-3 is obtained.

EXAMPLE 7

Synthesis of the Compounds of Formulae from VIII-1 to VIII-3

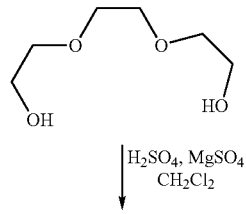

-continued
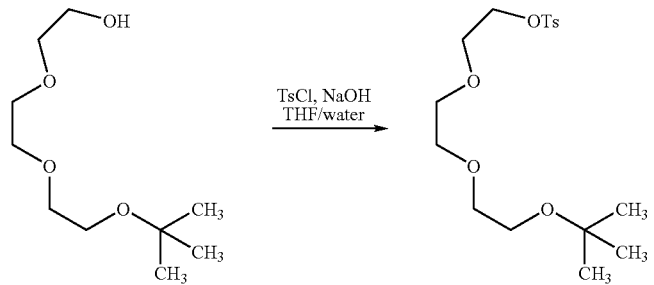
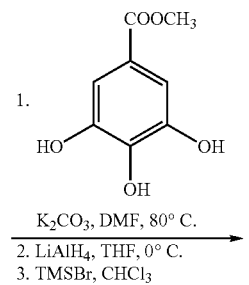
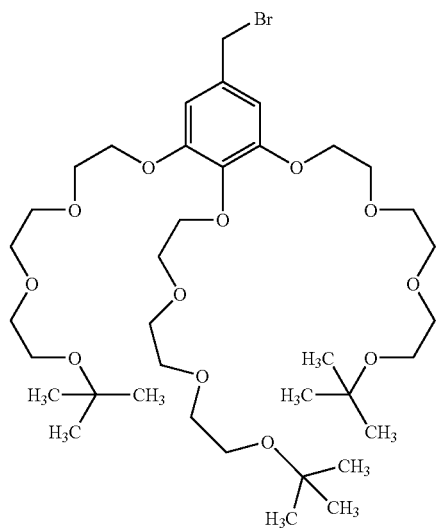
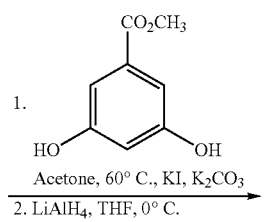
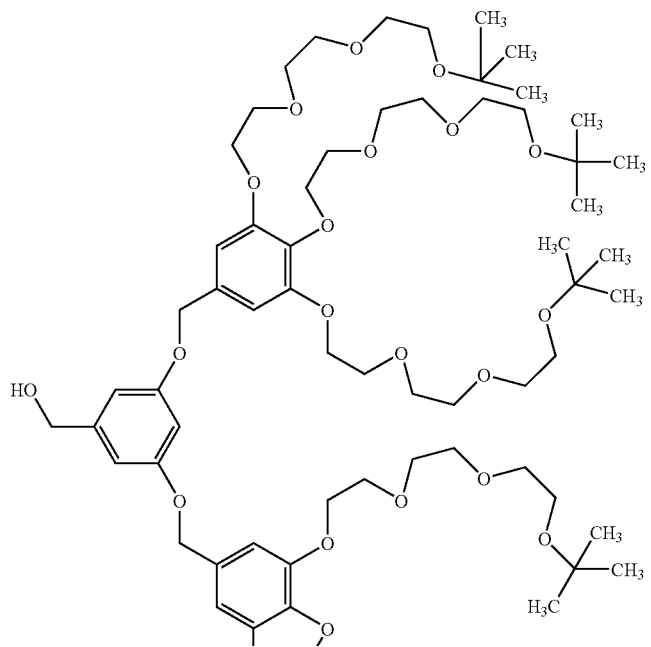
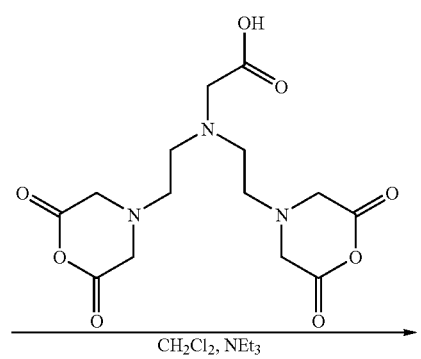

-continued

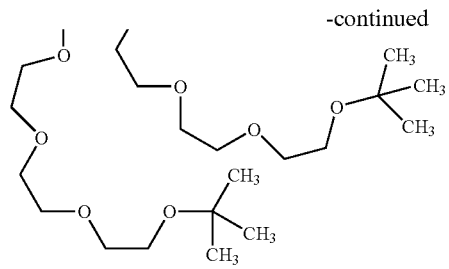

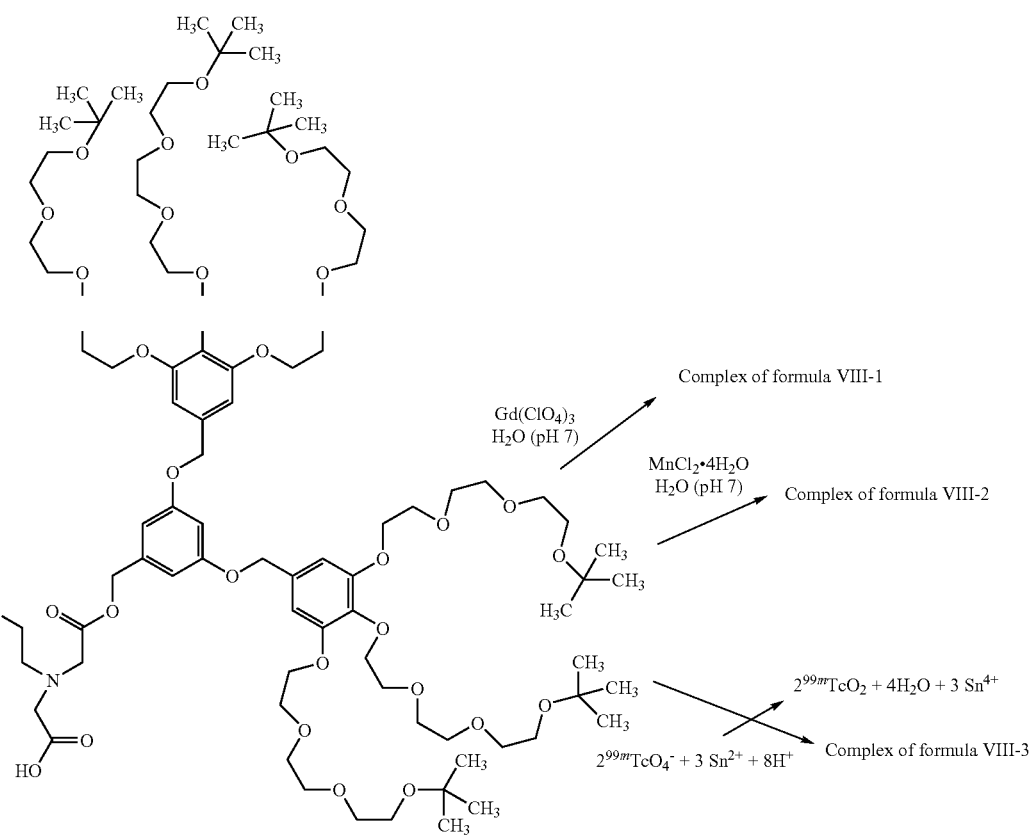

Step a): Synthesis of Tert-Butoxytriethylene Glycol from Tert-Butanol

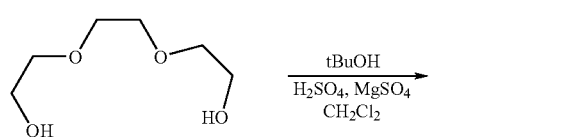

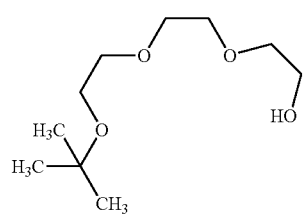

A solution of MgSO$_4$ (55.00 g, 0.45 mol) in 150 ml of dichloromethane is introduced into a two-necked round-bottomed flask equipped with a bulb condenser and stirred at ambient temperature. The assembly must imperatively be hermetically closed and under argon. Sulfuric acid H$_2$SO$_4$ (6.42 ml, 0.111 mol), triethylene glycol (15.00 ml, 0.111 mol) and then, very slowly, tert-butanol (52.80 ml, 0.556 mol) are then respectively introduced. The reaction medium is then stirred at ambient temperature for 19 hours and then at reflux for 2 hours. It is subsequently filtered, and the organic phase is washed with water (300 ml) and then with a saturated aqueous solution of NaCl (2×300 ml), before being dried over anhydrous MgSO$_4$, filtered, and then evaporated to dryness.

Purification: chromatography column at 3.5 cm in diameter, V$_{silica}$=400 ml, eluent: 95/5 CH$_2$Cl$_2$/MeOH The product 1 is obtained with a yield of 23% (5.29 g, 0.026 mol).

Step b): Reaction of the Product Obtained in Step a) with Tosyl Chloride

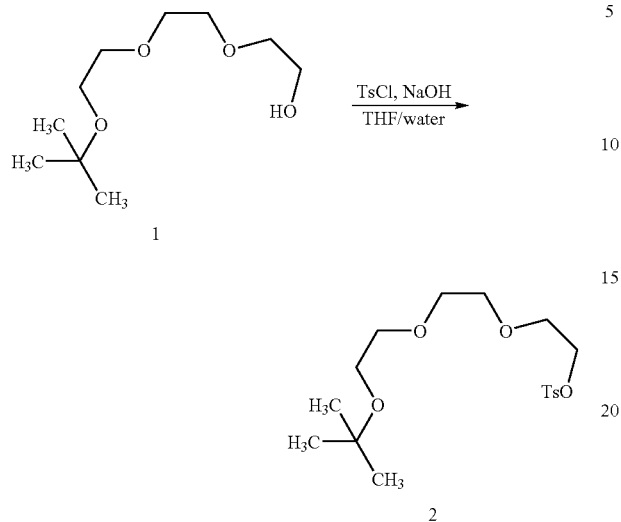

Tosyl chloride (1.85 g, 9.70 mmol) dissolved in 4 ml of THF is added dropwise to a solution of NaOH (0.53 g, 13.23 mmol) and of alcohol 1 (1.82 g, 8.82 mmol) in a water/THF mixture (2/14 ml) cooled to 0° C. After stirring for 68 hours at ambient temperature, the reaction medium is poured into 50 ml of a saturated aqueous solution of NaCl, cooled to 0° C. The organic phase obtained is washed with a saturated aqueous solution of NaCl (100 ml), dried over anhydrous $MgSO_4$, filtered, and evaporated to dryness.

Purification: chromatography column 3.5 cm in diameter, $V_{silica}$=400 ml, eluent: $CH_2Cl_2$/MeOH 98:2

The product 2 is obtained with a yield of 67% (0.87 g, 5.89 mmol).

Step c): Reaction of the Tosylate Obtained in Step b) with Methyl 3,4,5-Trihydroxybenzoate

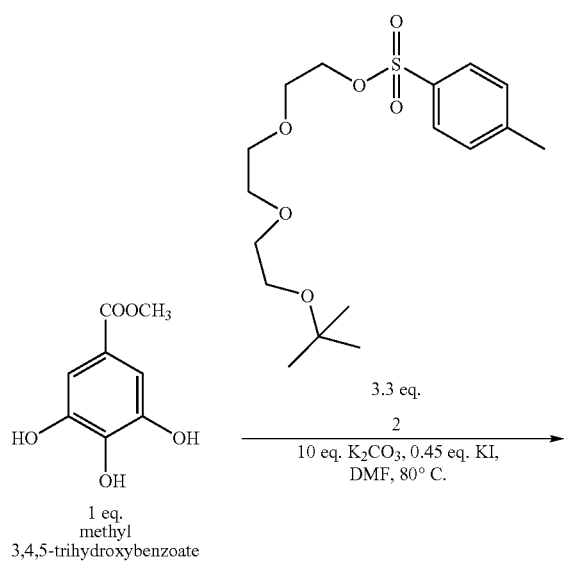

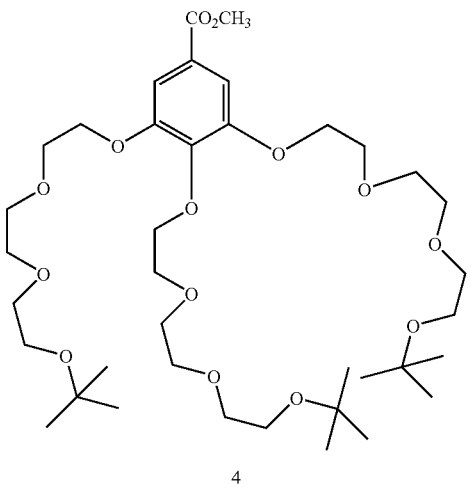

A solution of tosylate 2 (5.89 g, 16.28 mmol), of methyl 3,4,5-trihydroxybenzoate (0.91 g, 4.93 mmol), of $K_2CO_3$ (6.82 g, 0.163 mol) and of KI (0.37 g, 2.22 mmol) in dimethylformamide (DMF) (20 ml) is stirred and heated at 80° C., using an oil bath, for 72 hours.

After having stopped the heating, the reaction medium is cooled to ambient temperature and then filtered through Celite. After evaporation of the solvent, the residue of the filtrate is taken up in 300 ml of $CH_2Cl_2$. The organic phase thus obtained is washed with 3×300 ml of a saturated aqueous solution of NaCl, dried over anhydrous $MgSO_4$, then filtered and evaporated to dryness so as to give 4.60 g of crude product to be purified.

Purification: chromatography column 4.0 cm in diameter, $V_{silica}$=400 ml, eluent: 98/2 $CH_2Cl_2$/MeOH The product 4 is obtained with a yield of 82% (2.96 g, 4.03 mmol).

Step d): Reduction of the Product Obtained in Step c), Preferably with $LiAlH_4$, so as to Obtain the Corresponding Alcohol

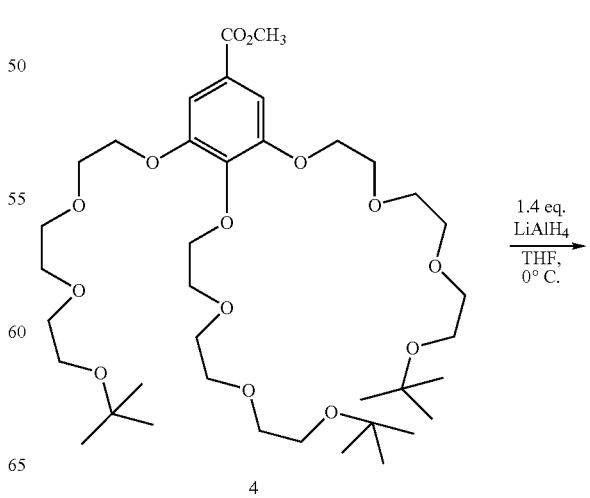

-continued

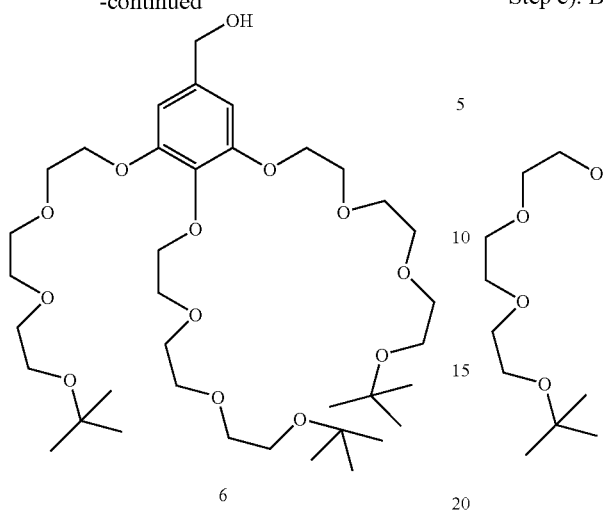

6

A 1M solution of LiAlH$_4$ in THF (6.64 ml, 6.64 mmol) is added dropwise, very carefully, to a solution of product 4 (2.96 g, 4.03 mmol) in 4 ml of anhydrous THF kept under argon and cooled to 0° C. with an ice bath. After stirring for 20 hours at ambient temperature, the reaction medium is cooled to 0° C. with an ice bath and the reaction is stopped by adding 4 ml of ethyl acetate (EtOAc), then 4 ml of methanol (MeOH) and, finally, 4 ml of water. The addition of ethyl acetate results in a violent reaction if it is not introduced slowly, the addition of water causes the salts to precipitate. The reaction medium is then filtered through Celite and then evaporated to dryness. The residue obtained is taken up in 35 ml of CH$_2$Cl$_2$, and washed with 3×35 ml of saturated aqueous solution of NaCl. The organic phase obtained is dried over anhydrous MgSO$_4$, filtered, and evaporated to dryness.

The product 6 is obtained with a yield of 88% (2.56 g, 3.55 mmol).

Step e): Bromination of the Product Obtained in Step d)

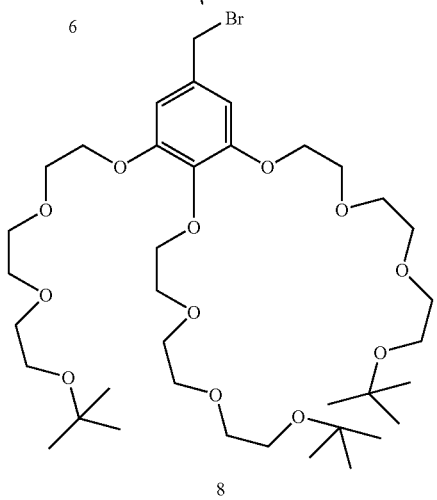

6

8

TMSBr (0.58 ml, 4.44 mmol) is added dropwise, using a syringe, to a solution of product 6 (2.56 g, 3.55 mmol) in 3 ml of anhydrous CHCl$_3$ kept under an inert atmosphere (argon) and at 0° C. using an ice bath. After stirring for 48 hours, the solvent is evaporated off and the product 8 is obtained with a yield of 90% (2.51 g, 3.19 mmol). No additional purification is necessary.

Step f): Reaction of the Product Obtained in Step e) with Methyl 3,5-Dihydroxybenzoate

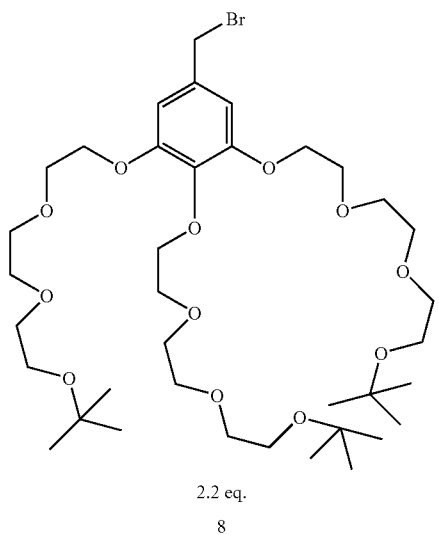

2.2 eq.
8

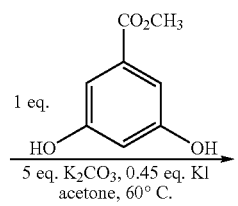

1 eq.

5 eq. K$_2$CO$_3$, 0.45 eq. KI
acetone, 60° C.

-continued

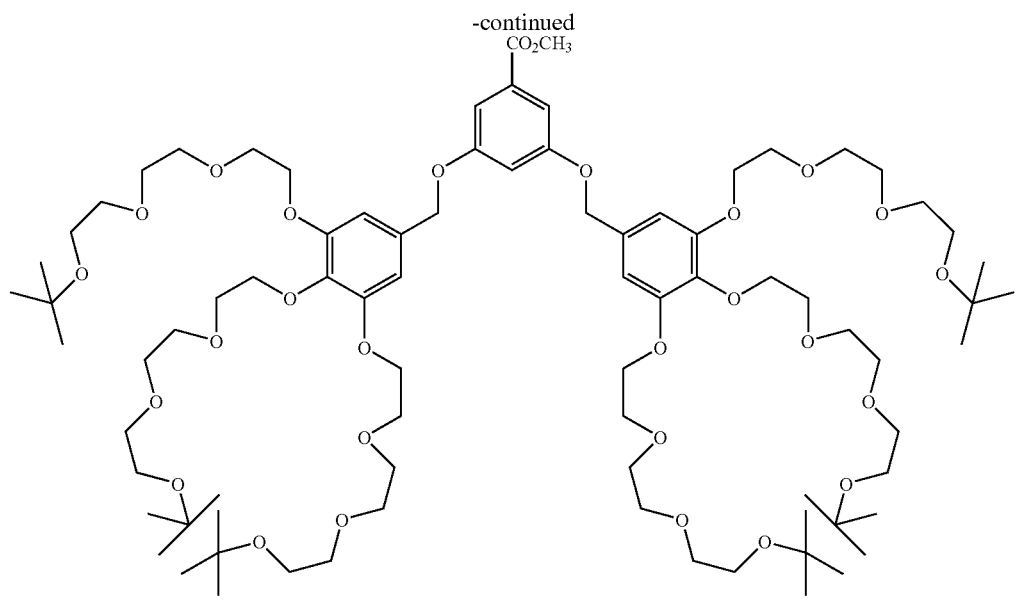

10

A solution of product 8 (2.51 g, 3.20 mmol), of 3,5-dihydroxybenzyl alcohol (0.25 g, 1.46 mmol), of $K_2CO_3$ (1.01 g, 7.28 mmol) and of KI (7 mg, 0.44 mmol) in 15 ml of acetone is heated at 60° C. for 72 hours. The reaction medium is then cooled to ambient temperature and filtered through Celite, and the filtrate thus obtained is evaporated to dryness.

The residue is taken up in 50 ml of $CH_2Cl_2$, and the organic phase obtained is washed with 3×50 ml of a saturated aqueous solution of NaCl, dried over anhydrous $MgSO_4$, filtered, and then evaporated to dryness so as to obtain 2.50 g of crude product to be purified.

Purification: chromatography column 4 cm in diameter, $V_{silica}$=450 ml, eluent: acetone The product 10 is obtained with a yield of 88% (1.98 g, 1.28 mmol). Yellowish oil.

Step g): Reduction of the Product Obtained in Step f) with $LiAlH_4$

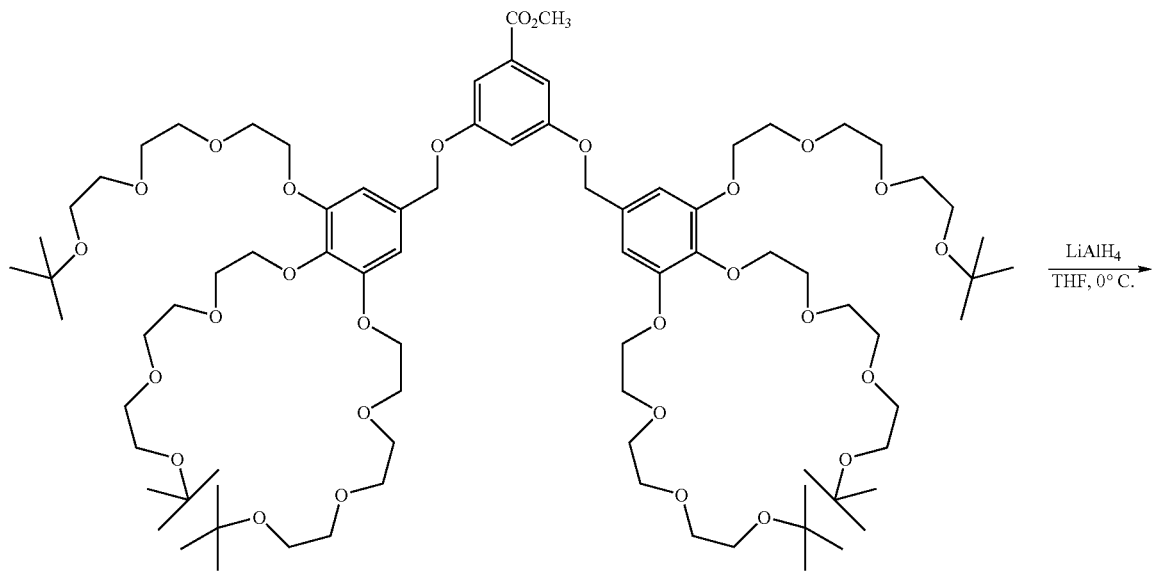

10

-continued

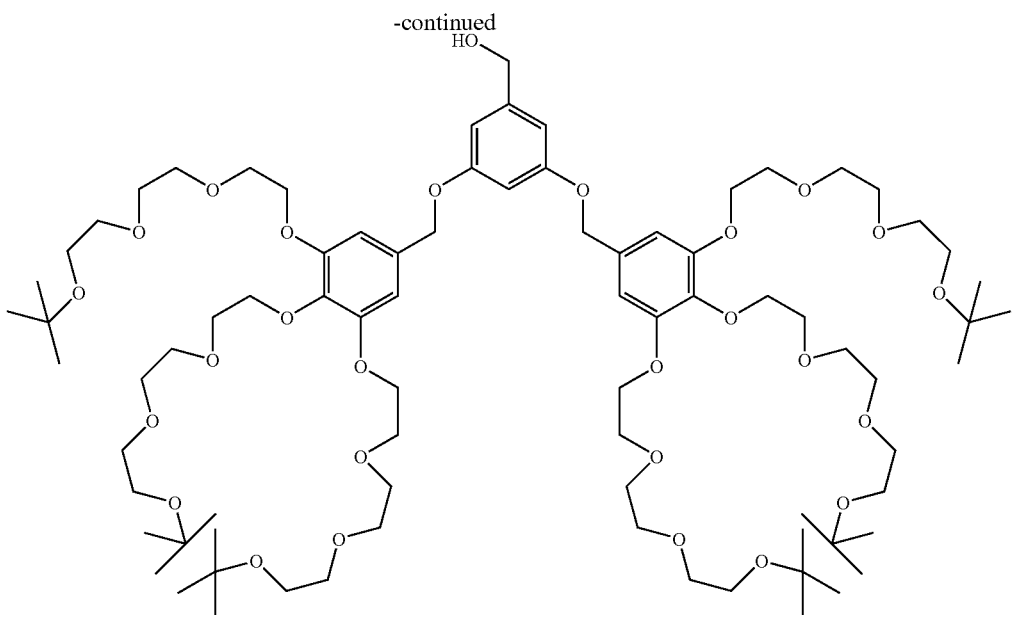

12

A 1M solution of LiAlH$_4$ in THF (1.73 ml, 1.73 mmol) is added dropwise, very carefully, to a solution of product 10 (1.95 g, 1.23 mmol) in 50 ml of anhydrous THF kept under argon and cooled to 0° C. with an ice bath. After stirring for 20 hours at ambient temperature, the reaction medium is cooled to 0° C. with an ice bath and the reaction is stopped by adding 10 ml of ethyl acetate (EtOAc), then 10 ml of methanol (MeOH) and, finally, 10 ml of water. The addition of ethyl acetate results in a violent reaction if it is not introduced slowly, the addition of water causes the salts to precipitate.

The reaction medium is then filtered through Celite and then evaporated to dryness. The residue obtained is taken up in 50 ml of CH$_2$Cl$_2$ and washed with 3×50 ml of a saturated aqueous solution of NaCl. The organic phase obtained is dried over anhydrous MgSO$_4$, filtered, and evaporated to dryness.

The product 12 is obtained with the yield of 92% (1.76 g, 1.13 mmol).

Step h): Reaction of the Product Obtained in Step g) with Diethylenetriaminepentaacetic Dianhydride.

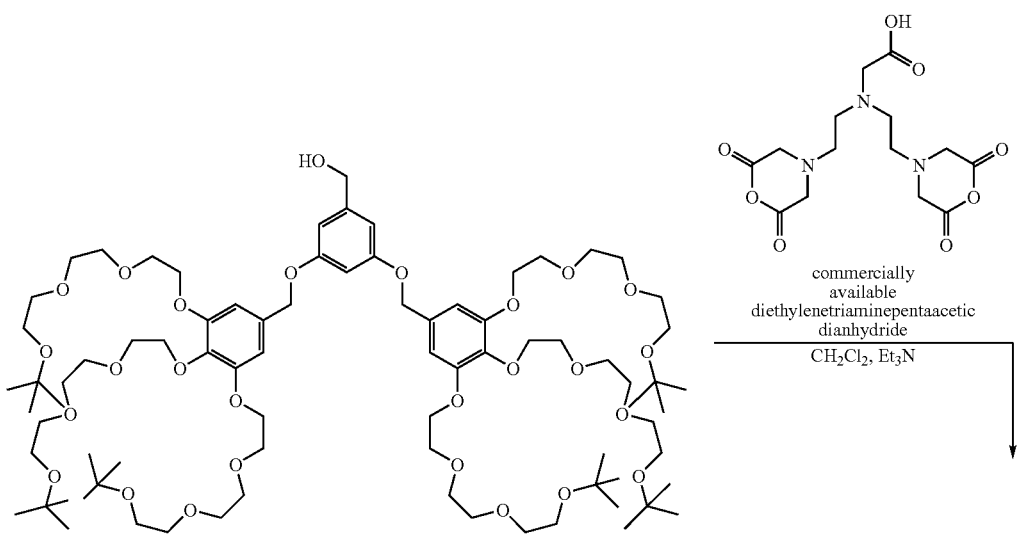

12

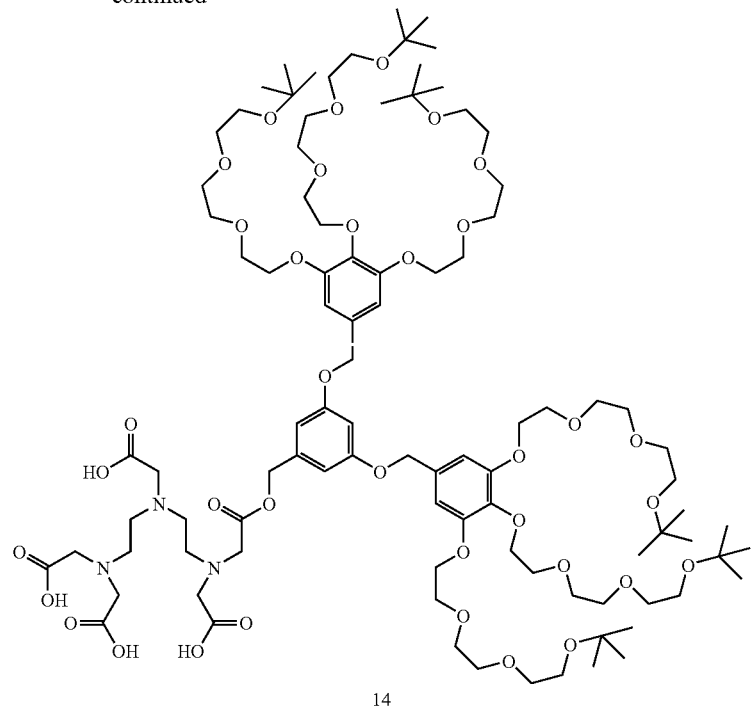

14

The diethylenetriaminepentaacetic dianhydride (115 mg, 0.32 mmol) and the product 12 (500 mg, 0.32 mmol) are dissolved in 35 ml of anhydrous methylene chloride, and the suspension obtained is stirred at 50° C. for 30 minutes. Triethylamine (0.45 ml, 3.2 mmol) is then added, and the reaction medium is stirred at 50° C. for 12 hours, before being cooled to ambient temperature and concentrated to 5 ml. 30 ml of hexane are then added thereto, and the solution obtained is left in the fridge (+4° C.) overnight. The product that has precipitated is washed with hexane, dried under vacuum, and then purified with a flash chromatography column.

Purification: chromatography column 1 cm in diameter, $V_{silica}$=20 ml, eluent: $CH_2Cl_2$/50% MeOH The product 14 is obtained with a yield of 89% (553 mg, 0.28 mmol). Yellowish oil.

Step i): Reaction of the Product Obtained in Step g) with Gd (III) Chloride or Mn (II) Chloride or Pertechnetate 1. Reaction with Gd chloride

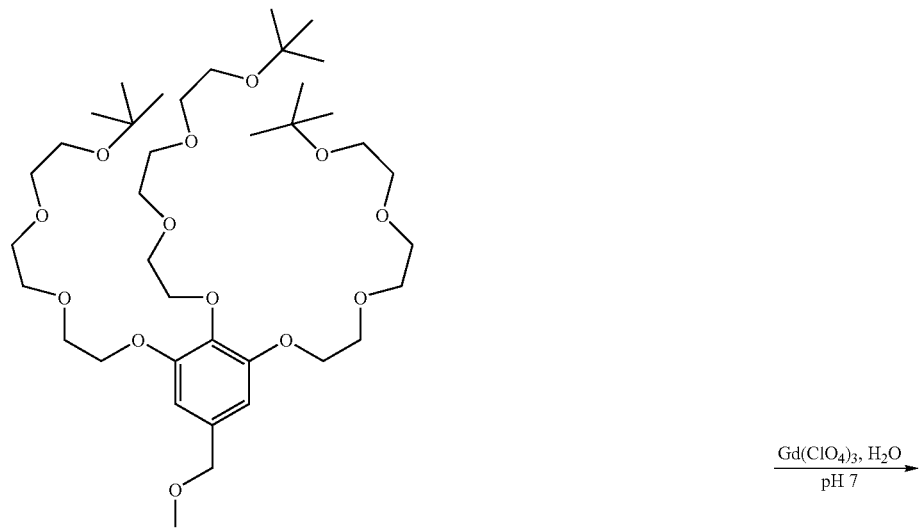

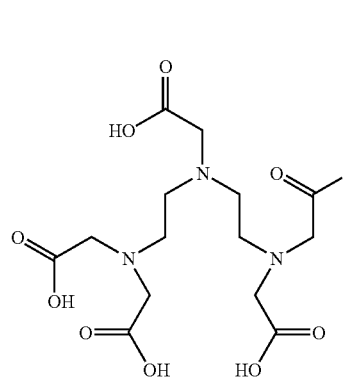
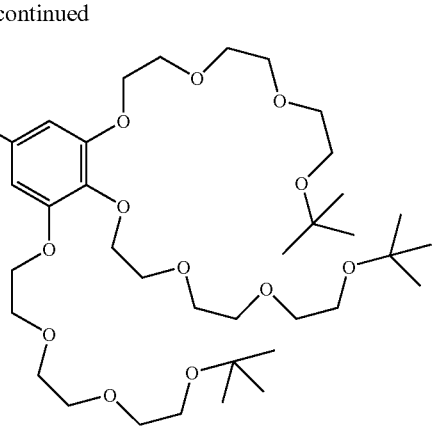

14

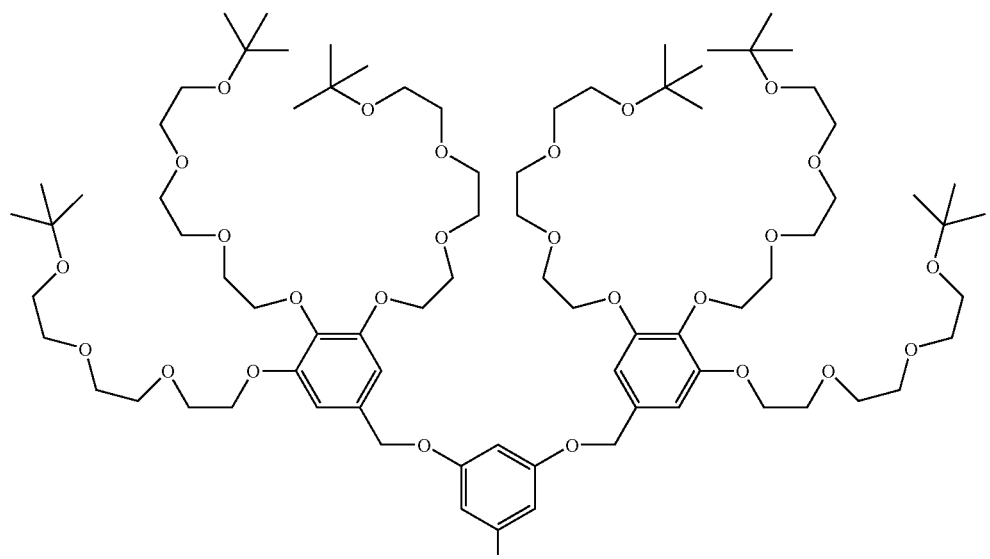

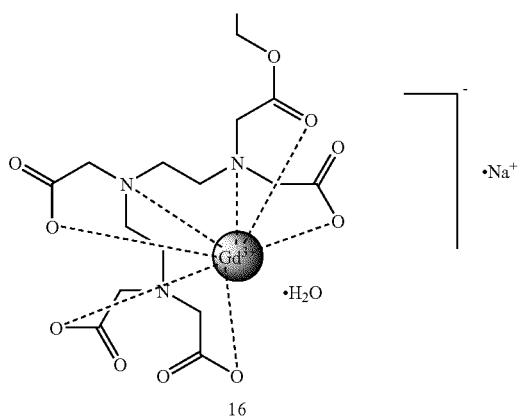

16

The ligand 14 (200 mg, 0.10 mmol) and Gd(ClO$_4$)$_3$ (95 mg of a 50% solution in water, 0.10 mmol) are solubilized in 5 ml of distilled water, and the solution is stirred at ambient temperature for 12 hours while keeping the pH constant at 7 by adding a 1M solution of NaOH. The reaction medium is then treated with Chelex resin for 1 hour in order to remove the free Gd$^{3+}$ ions, and then filtered and lyophilized.

The complex 16 is obtained with a yield of 87% (189 mg, 0.087 mmol). Yellowish oil.

The complex of formula VIII-1 is obtained.

2. Reaction with Mn chloride
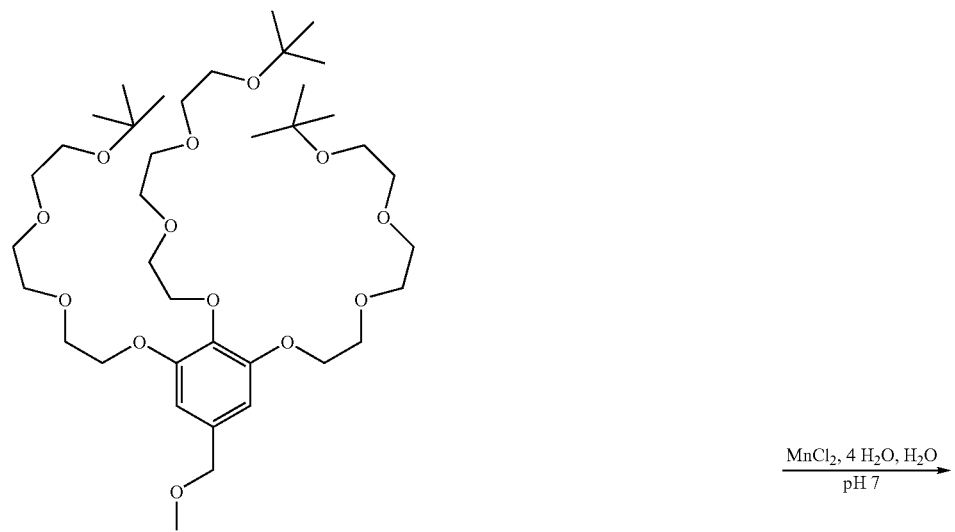
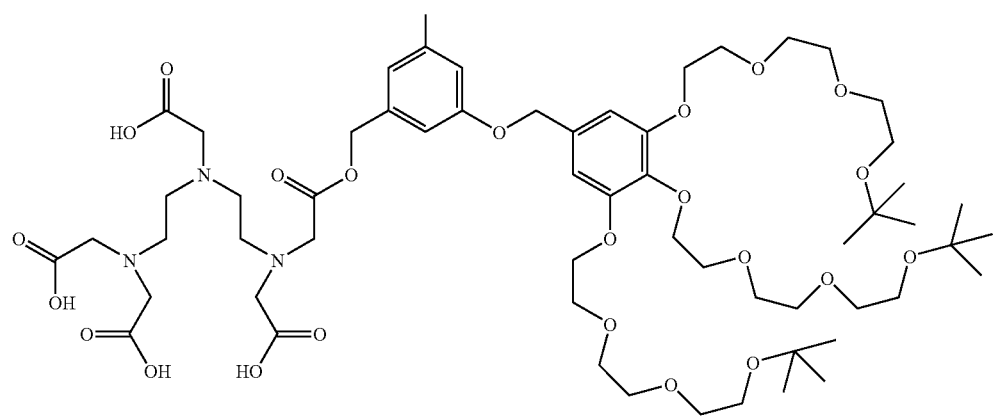
14
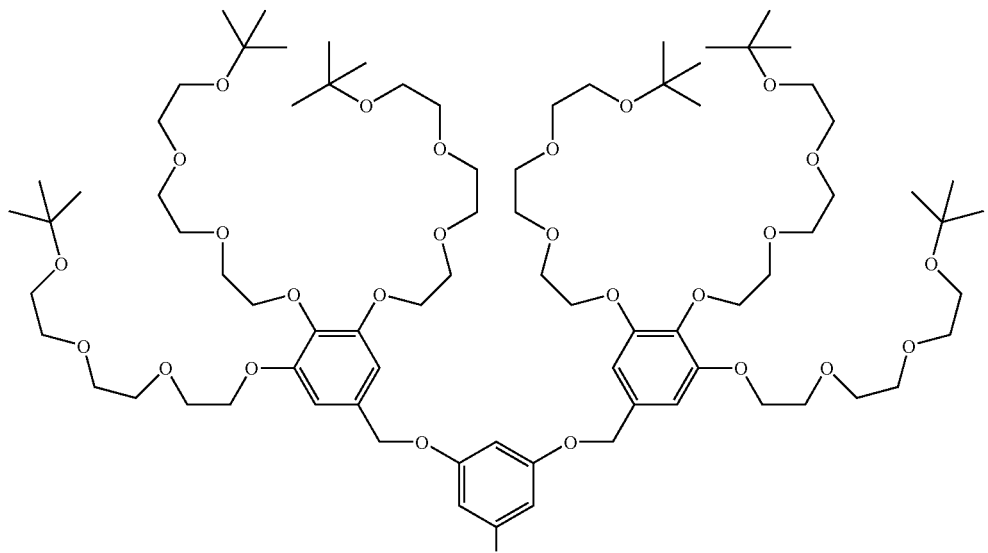

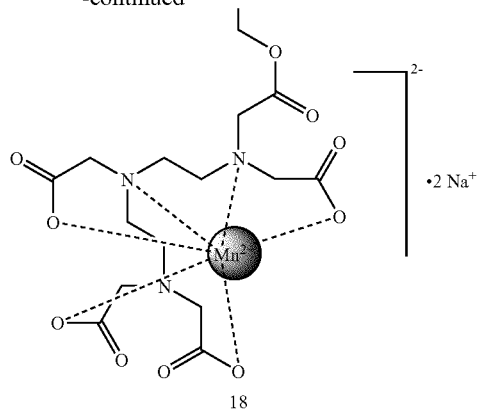

18

MnCl$_2$·4H$_2$O (21 mg, 0.10 mmol) is added to a solution of product 14 (200 mg, 0.10 mmol) in water (5 ml), stirred at ambient temperature. After stirring for 30 minutes, the impure complex 18 (presence of inorganic impurities of NaCl type) is lyophilized. A purification may be carried out in order to remove the sodium salts.

Purification: after lyophilization, the dry residue is taken up in a minimum amount of dichloromethane, and the organic phase obtained is washed with a virtually saturated aqueous solution of NaCl before being dried over anhydrous MgSO$_4$, filtered, and then evaporated to dryness.

The complex 18 is obtained with a yield of 88% (189 mg, 0.088 mmol).

The complex of formula VIII-2 is obtained.

3. Reaction with pertechnetate

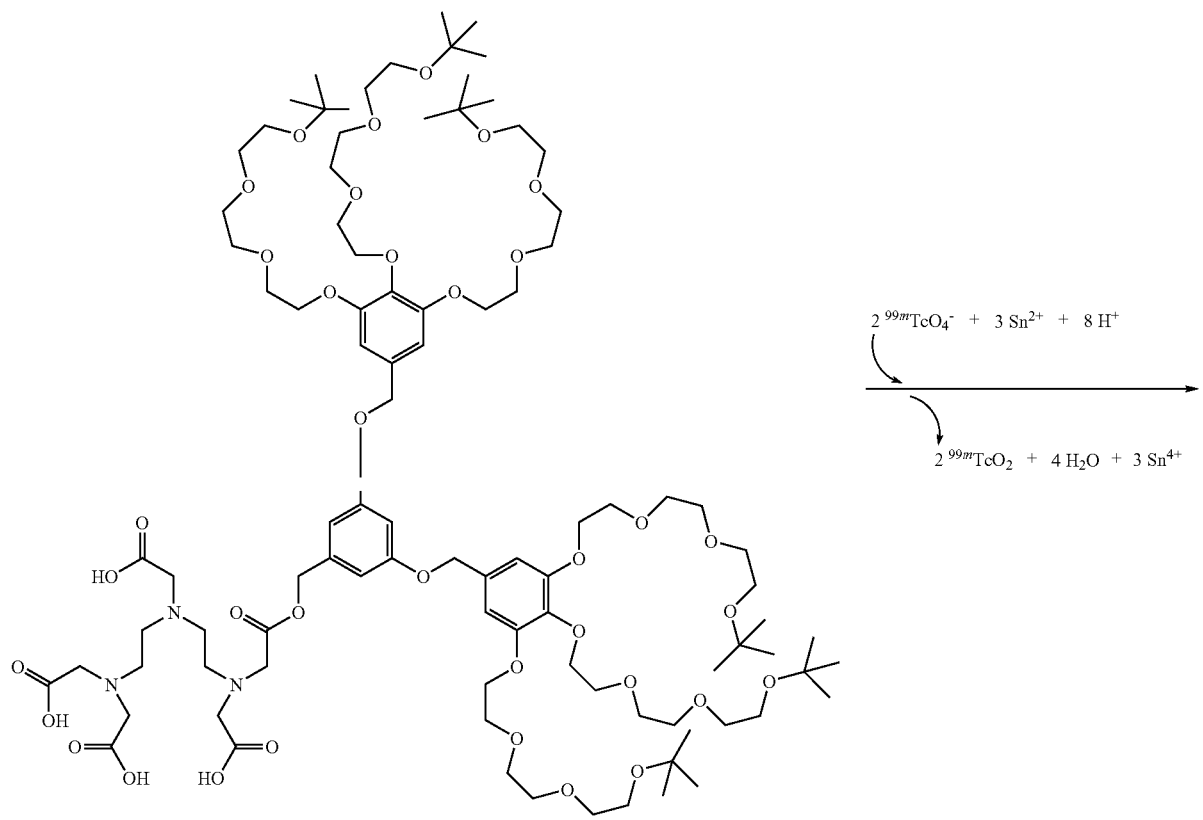

14

$2\ ^{99m}\text{TcO}_4^- + 3\ \text{Sn}^{2+} + 8\ \text{H}^+$ $2\ ^{99m}\text{TcO}_2 + 4\ \text{H}_2\text{O} + 3\ \text{Sn}^{4+}$

[$^{99m}$Tc (III)-DTPA-PEG-tBu]$^-$·Na$^+$

20

Manipulation carried out in a shielded nuclear medicine hood equipped with an activity meter:

185 MBq (5 mCi) of pertechnetate 99mTc$^{3+}$O$_4^-$ (2 to 4 ml) leaving the generator in solution in sterile, apyrogenic physiological saline are added to a vial containing 18 µmol of complex 14-CaNa$_3$ and 2 µmol of stannous chloride (Sn$^{2+}$) lyophilized from a stock solution.

The mixture is stirred gently and left to react for 2 minutes at ambient temperature.

The quality of the labeling is verified by chromatography on Whatman paper (3MM CHR) with methyl ethyl ketone as mobile phase: the labeled complex does not migrate (Rf=0) and the free pertechnetate migrates with the solvent front (Rf=1).

Under these conditions, the labeling is always greater than 98%.

The complex of formula VIII-3 is obtained.

EXAMPLE 8

Synthesis of the Compounds of Formulae from IX-1 to IX-3

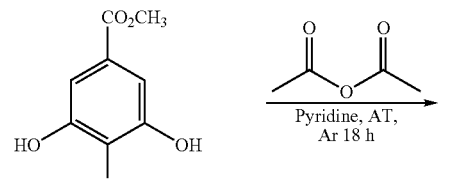
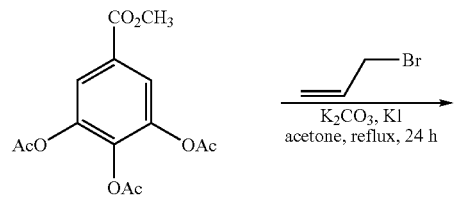
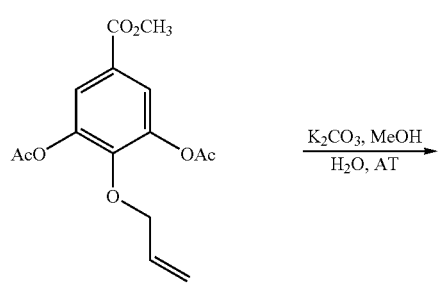
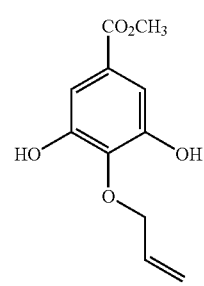
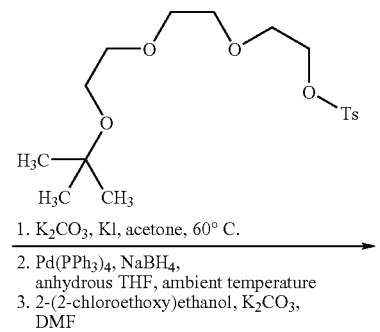
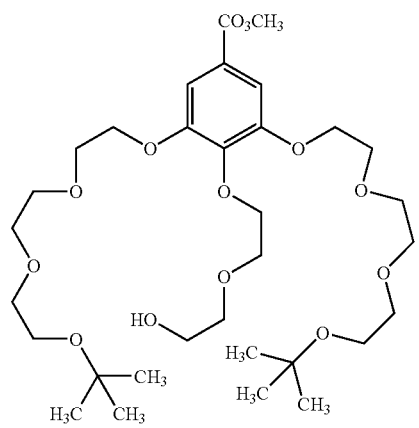
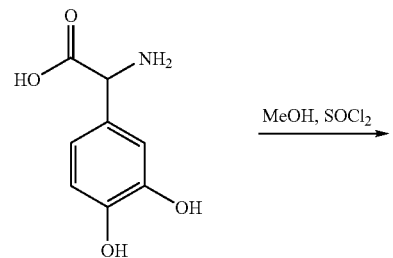
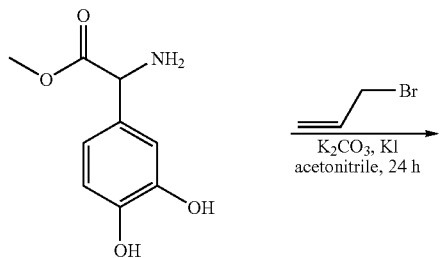

143
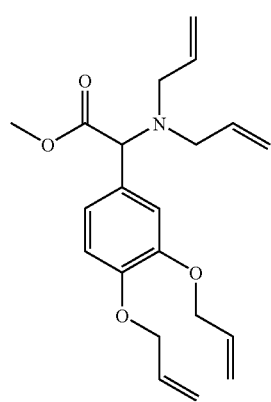
NaOH
THF/water
→
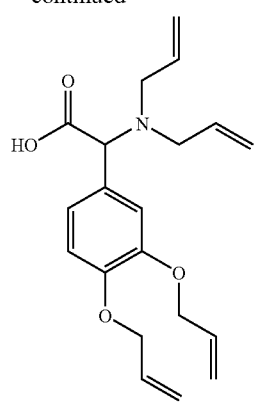
SOCl₂
THF
→
144
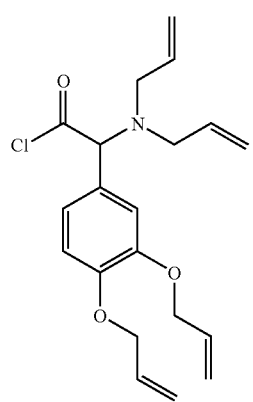
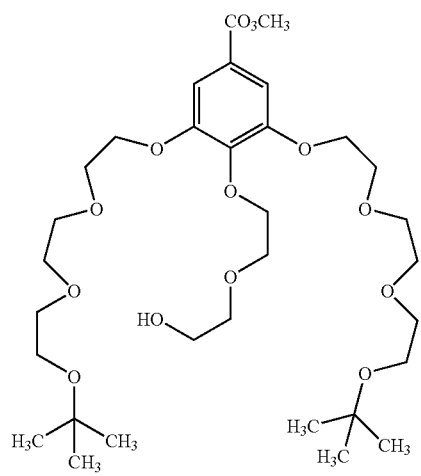
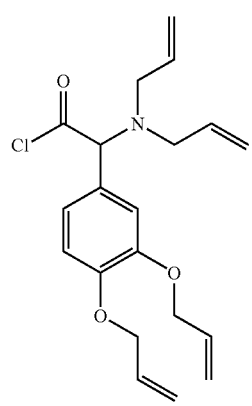
DCC, DMAP
HOBt, CH₂Cl₂
→
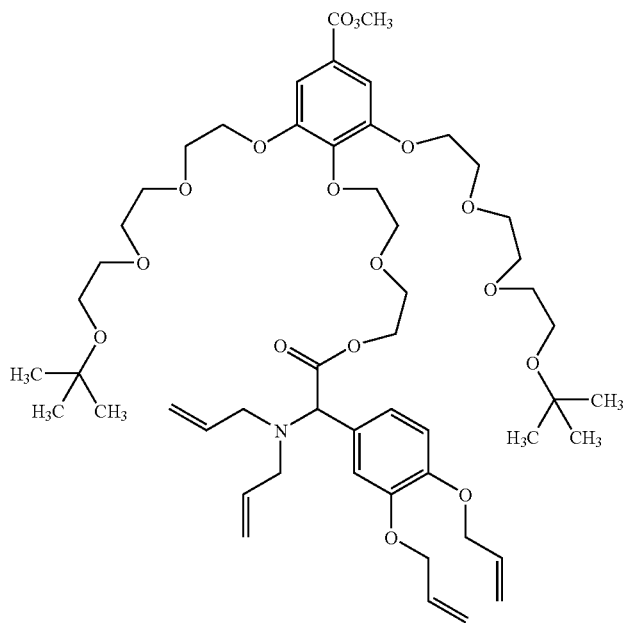
1. LiAlH₄, THF, 0° C.
2. DTPA dianhydride, NEt₃, CH₂Cl₂, 50° C.
3. Pd(PPh₃)₄, K₂CO₃ MeOH
→

-continued
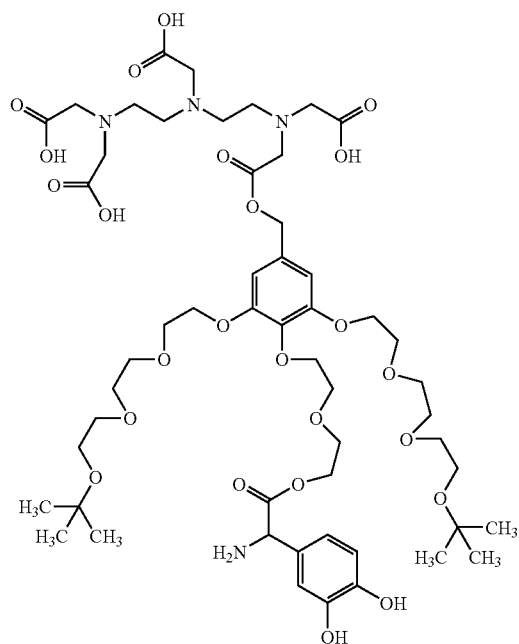
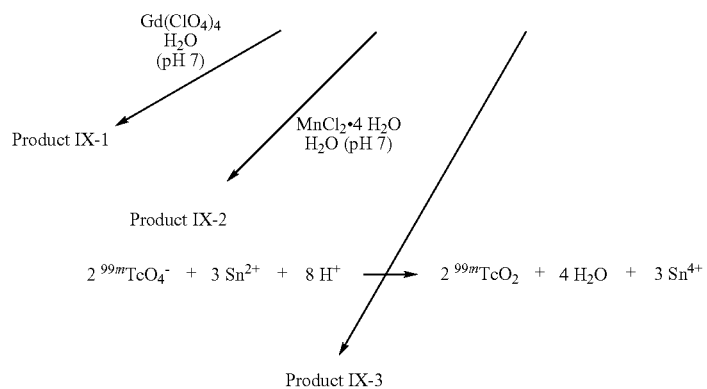
$2\ ^{99m}TcO_4^- + 3\ Sn^{2+} + 8\ H^+ \longrightarrow 2\ ^{99m}TcO_2 + 4\ H_2O + 3\ Sn^{4+}$
Product IX-3

147
EXAMPLE 9

Synthesis of the Compounds of Formulae from X-1 to X-3

148
EXAMPLE 10

Synthesis of the Compounds of Formula A of First and Second Generation

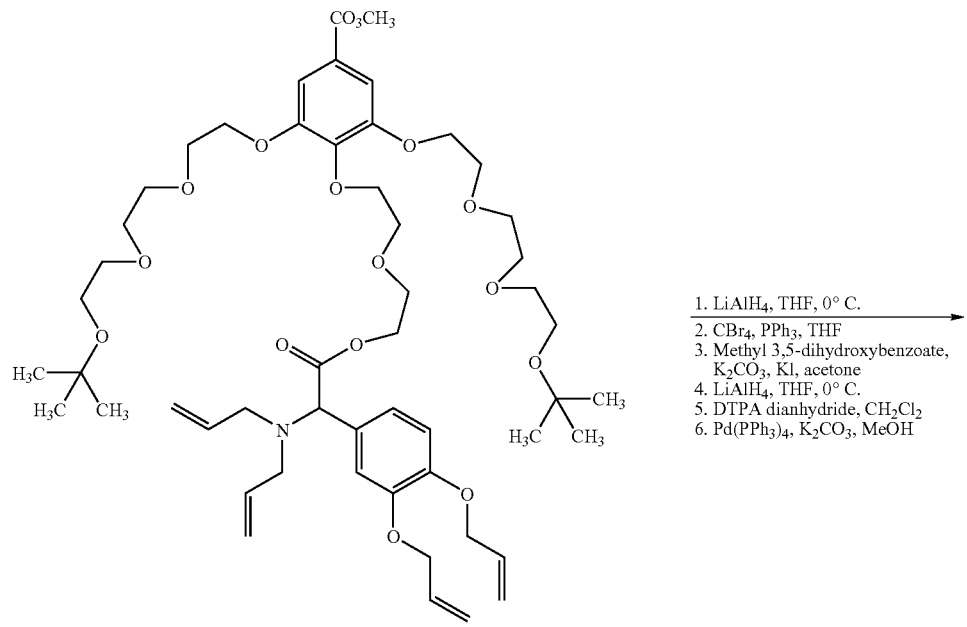

1. LiAlH$_4$, THF, 0° C.
2. CBr$_4$, PPh$_3$, THF
3. Methyl 3,5-dihydroxybenzoate, K$_2$CO$_3$, KI, acetone
4. LiAlH$_4$, THF, 0° C.
5. DTPA dianhydride, CH$_2$Cl$_2$
6. Pd(PPh$_3$)$_4$, K$_2$CO$_3$, MeOH

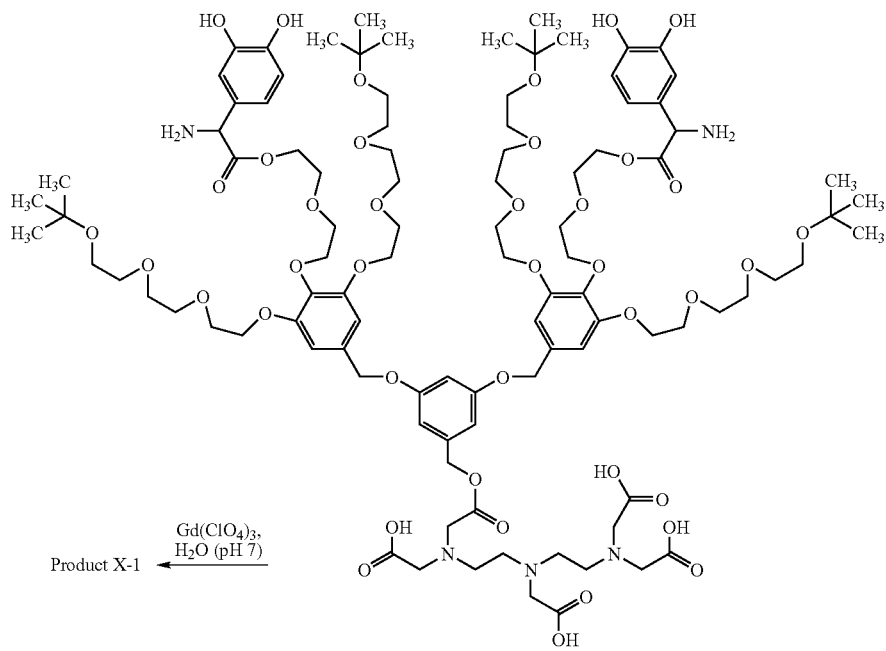

Product X-1 ← Gd(ClO$_4$)$_3$, H$_2$O (pH 7)

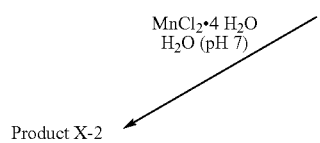

MnCl$_2$·4 H$_2$O, H$_2$O (pH 7)

Product X-2

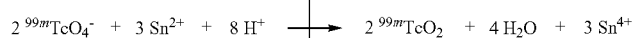

2 $^{99m}$TcO$_4^-$ + 3 Sn$^{2+}$ + 8 H$^+$ → 2 $^{99m}$TcO$_2$ + 4 H$_2$O + 3 Sn$^{4+}$

Product X-3

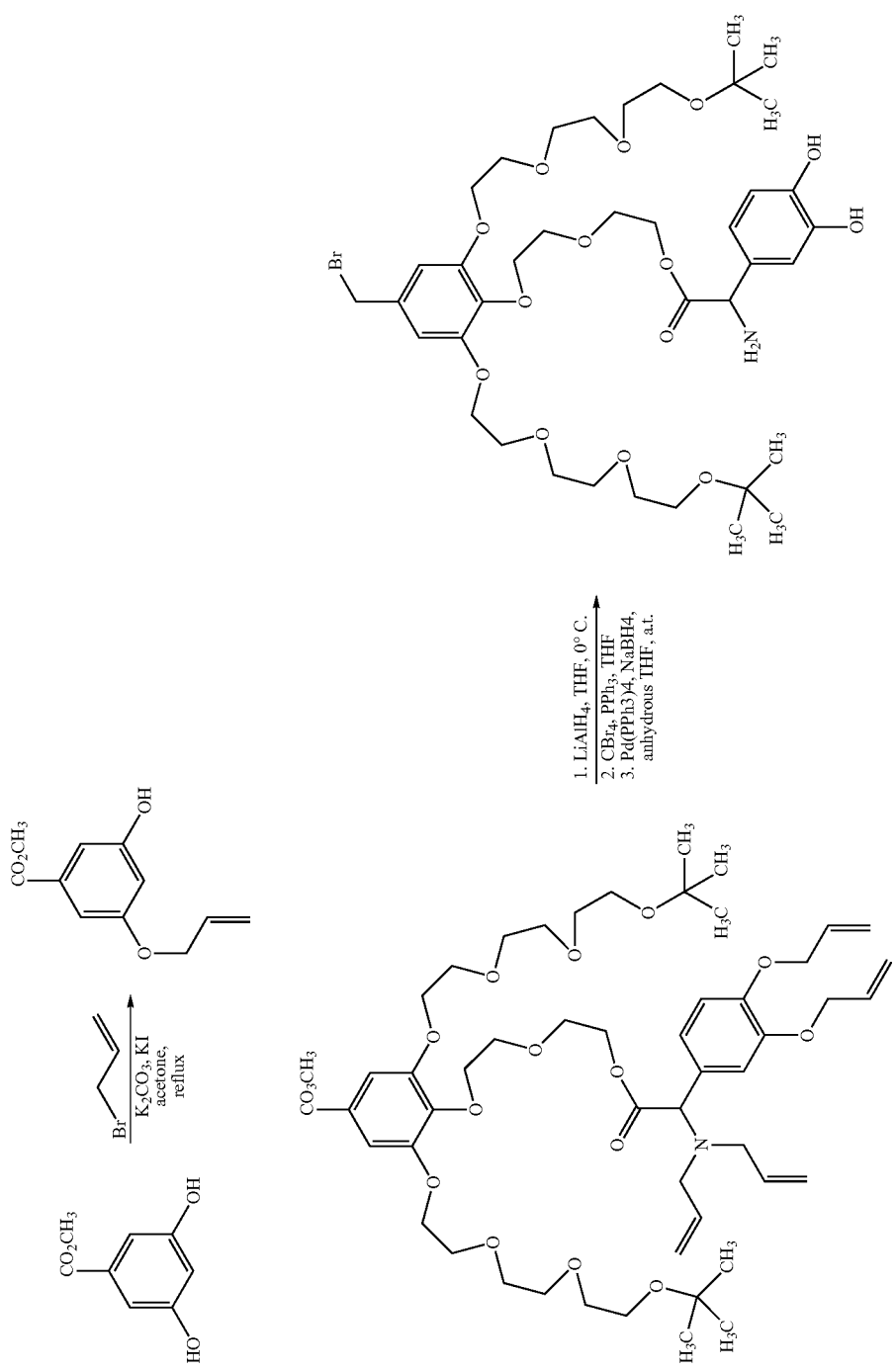

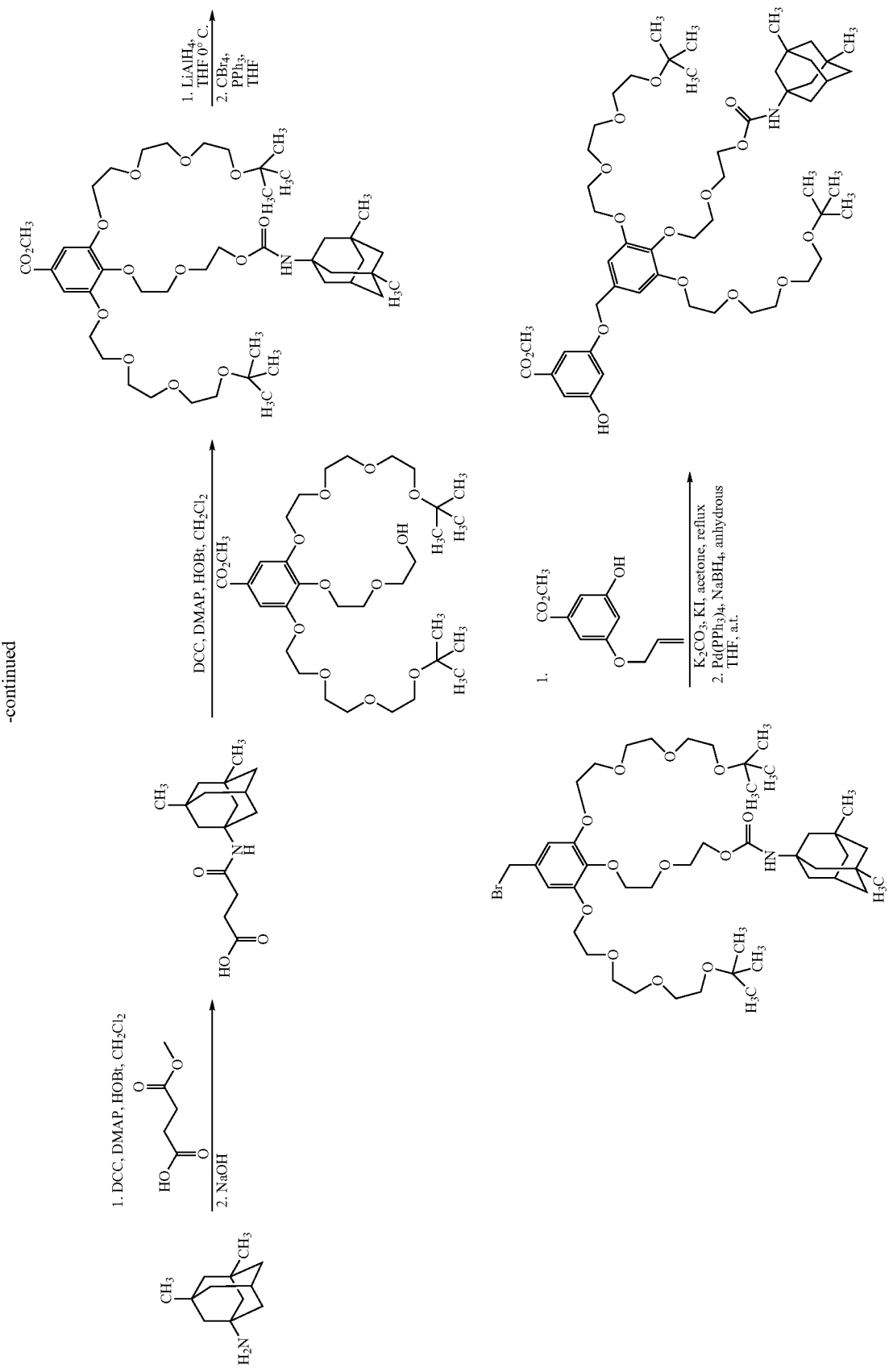

1. -continued
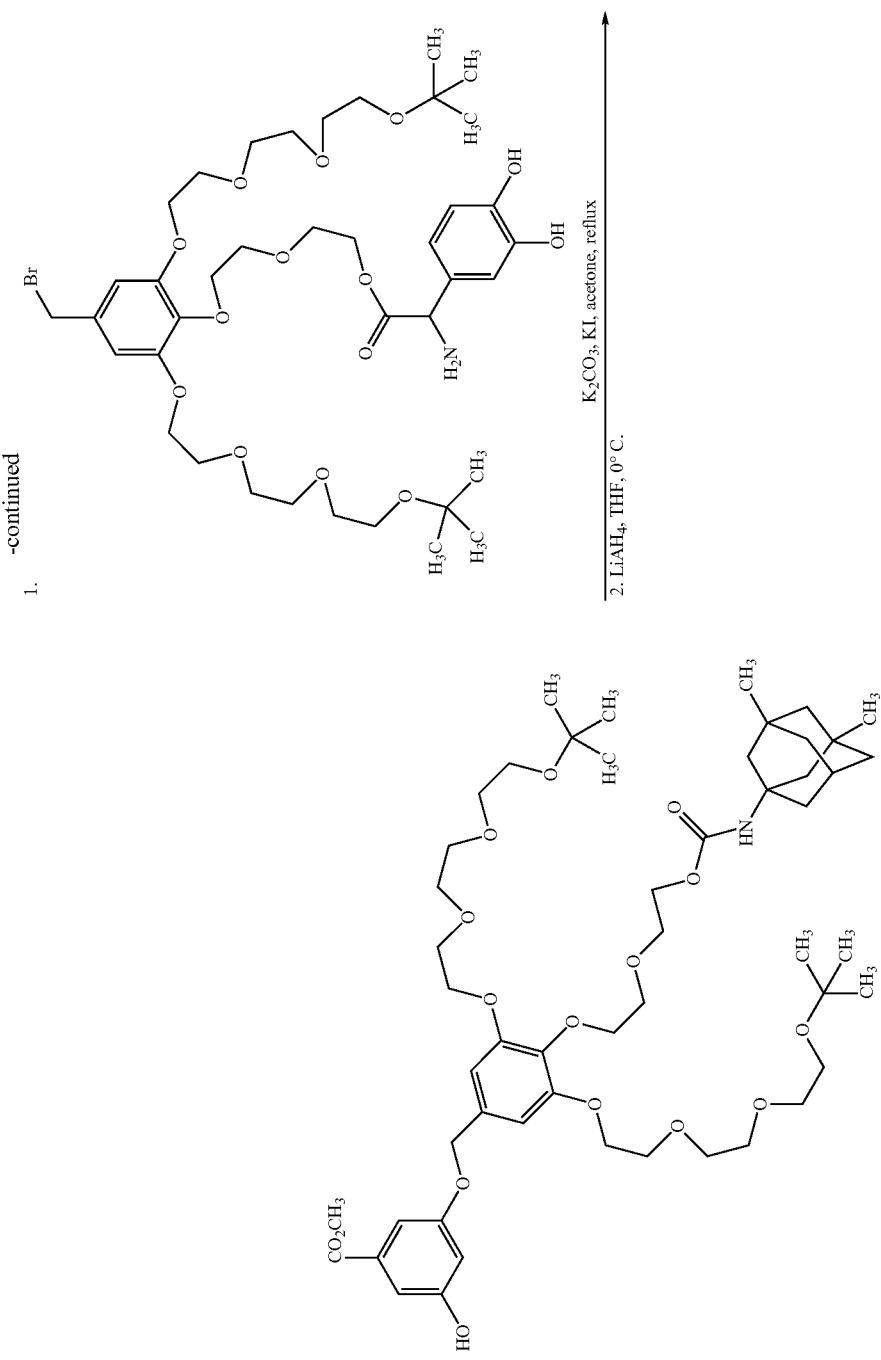

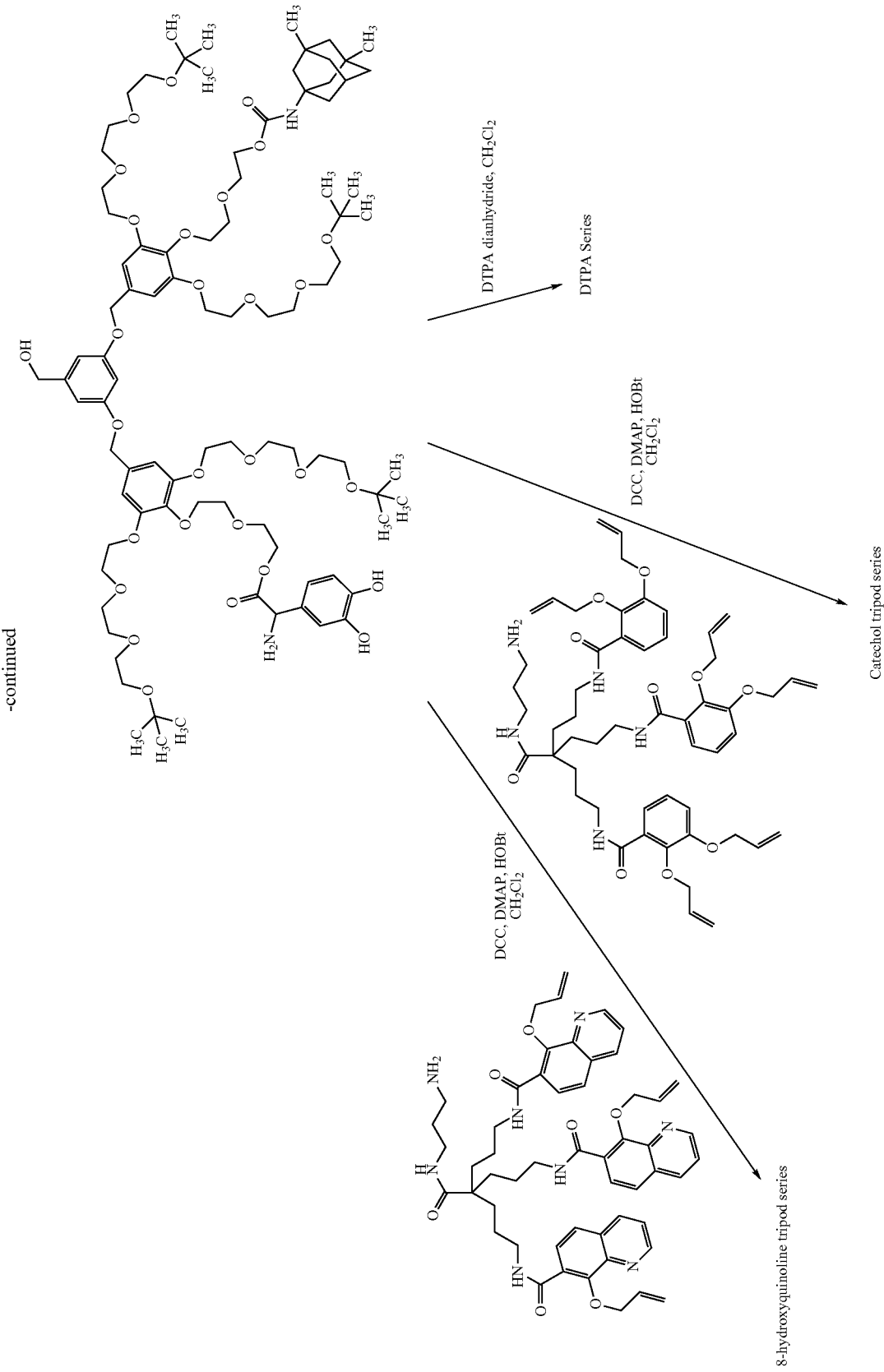

EXAMPLE 11
Synthesis of the Compounds of Formula A of Third Generation
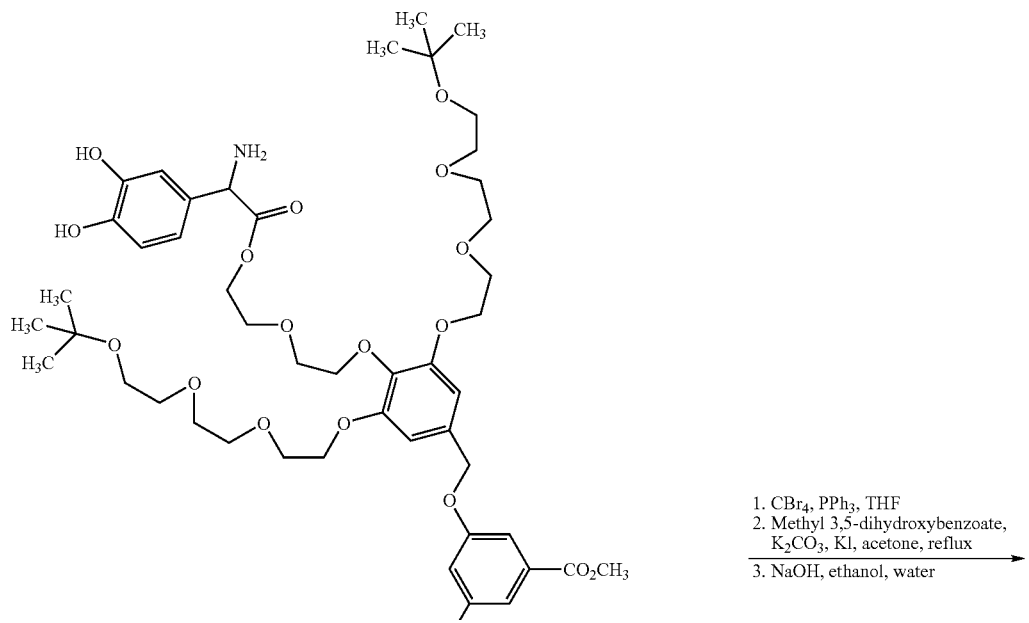
1. CBr₄, PPh₃, THF
2. Methyl 3,5-dihydroxybenzoate, K₂CO₃, KI, acetone, reflux
3. NaOH, ethanol, water
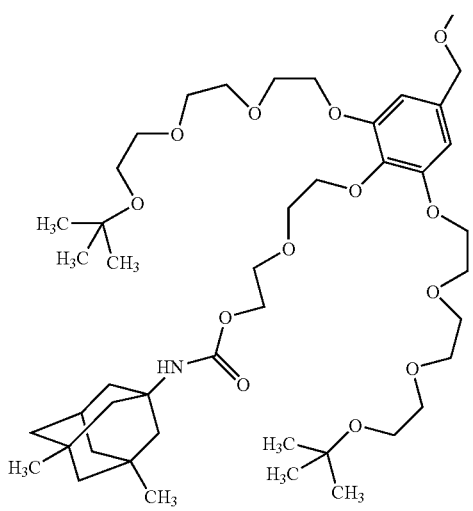

159 160
-continued
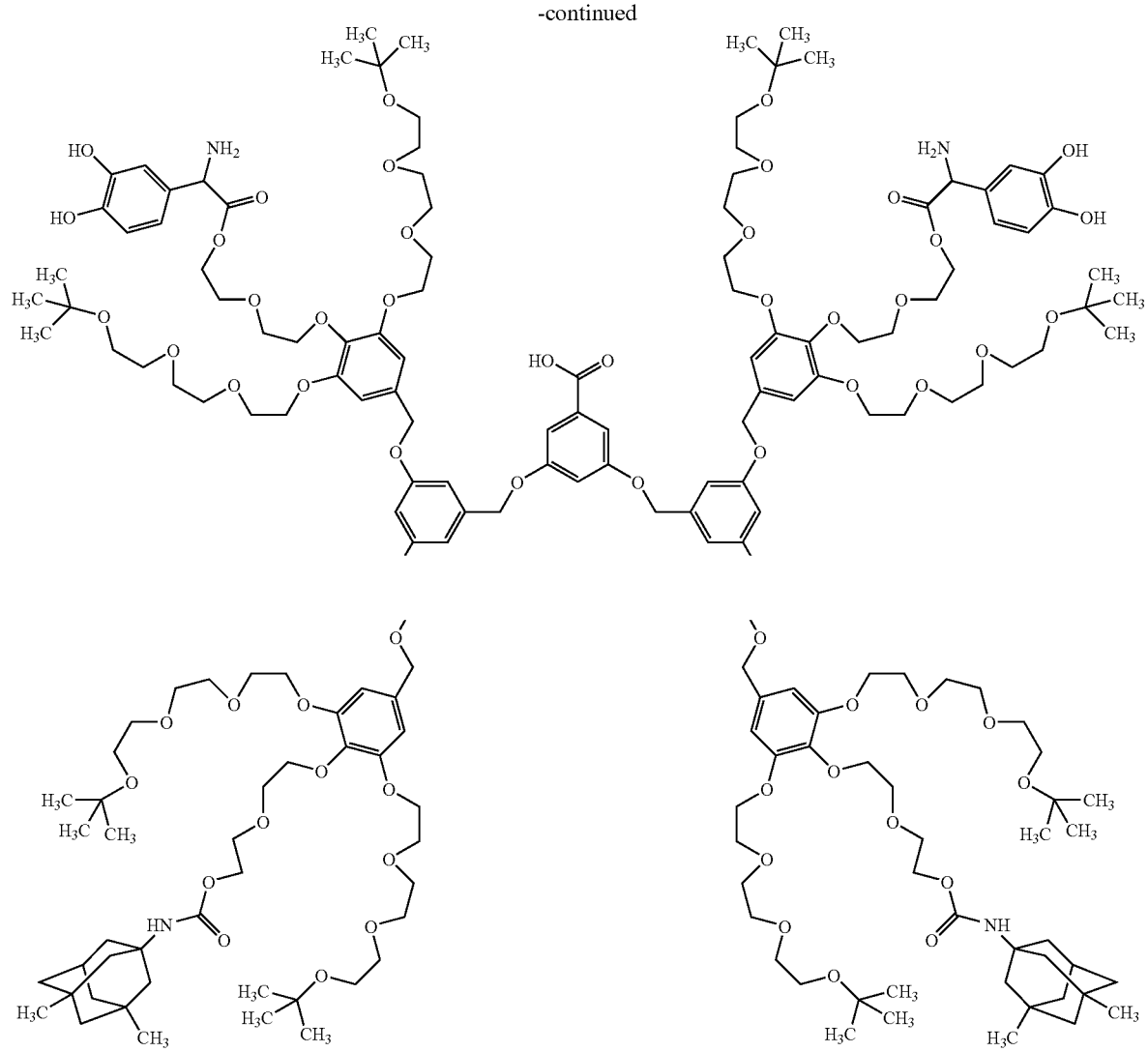
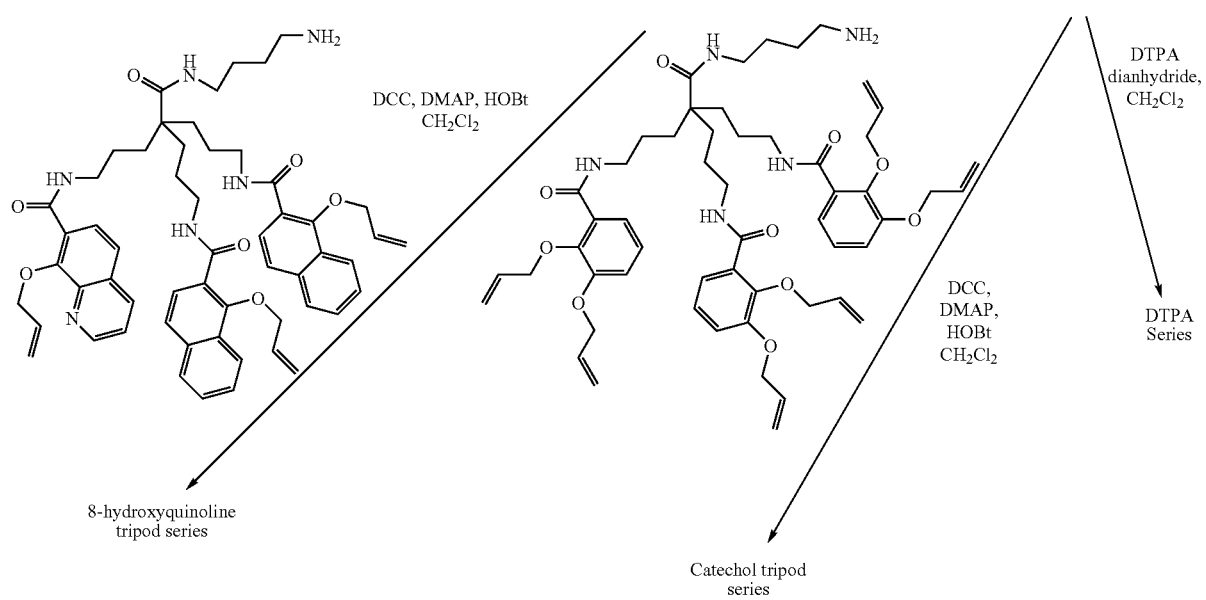

EXAMPLE 12

Synthesis of the Compounds of Formula A of First, Second or Third Generation Comprising A Butanediamine Spacer The synthesis of the globular dendritic structure formed by the functionalized first-generation dendrons of the complexes of the invention, and also of the globular dendritic structure of the second-generation dendrons, was shown in example 10. The synthesis of the third-generation globular dendritic structure was similarly shown in example 11. After the formation of these dendrons, a spacer according to the invention is, if desired, introduced.

When this spacer is 1,4-butanediamine, the synthesis takes place according to the following scheme, for the first-generation complex:

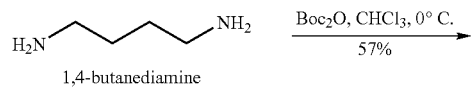

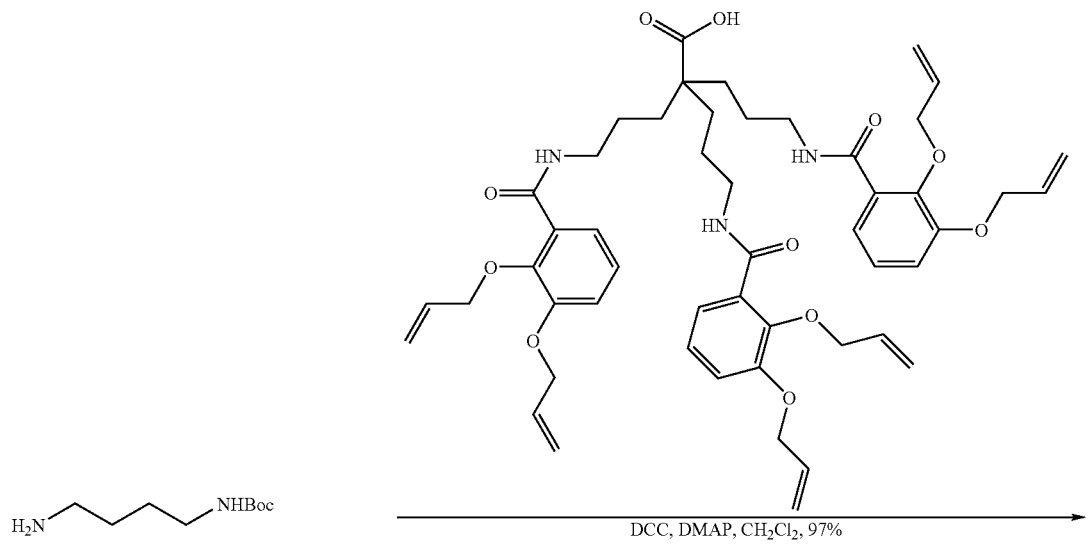

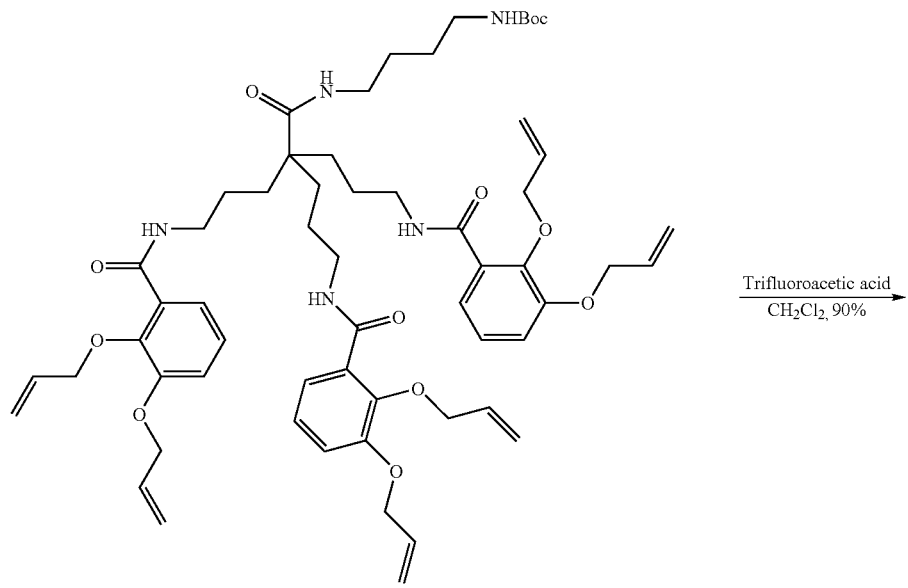

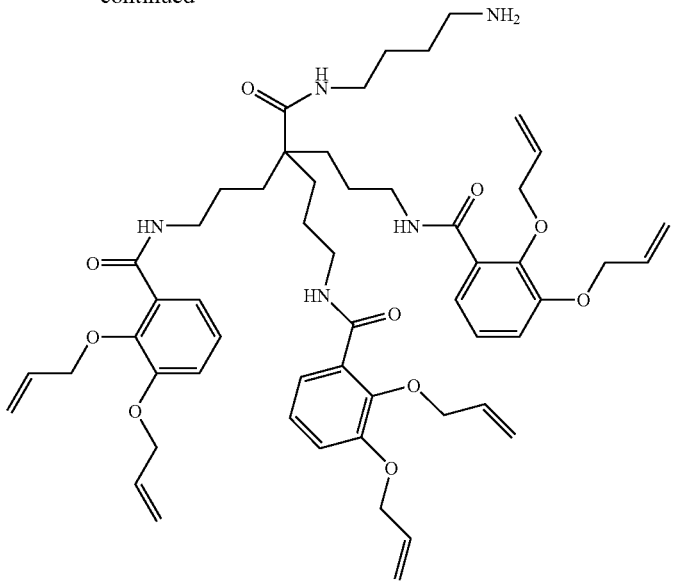

Then, as shown in examples 10 and 11, the chelate is introduced so as to obtain the desired products.

Although the invention was described in the preceding examples as relating to the markers $Gd^{3+}$, $Mn^{2+}$ and $99mTc^{3+}$, it will be clearly apparent to those skilled in the art that any marker of interest may be complexed in the same way.

In addition, although the invention was described in the preceding examples with functionalizations of the dendritic structure imparting, to the complexes of the invention, vectorization to the brain, it will become clearly apparent to those skilled in the art that the functionalization of the dendrites with groups which bind specifically to receptors of other organs may be used to obtain contrast agents specific for other organs.

Furthermore, although the invention was described with first-, second- or third-generation dendritic structures, it will be clearly apparent to those skilled in the art that it is entirely possible for complexes comprising dendritic structures of higher generations to be envisioned.

In the same manner, the dendrites were described in the above text as comprising three or four ethylene glycol units, but it will be clearly apparent to those skilled in the art that it is entirely possible for the use of dendrites comprising more than four ethylene glycol units to be envisioned, in particular in the case of voluminous functionalizing groups.

In the same manner, although the methods of synthesis were described using particular reducing agents, protective groups and other compounds, it will be clearly apparent to those skilled in the art that other such reducing agents, protective groups and compounds having the same function as that described in the examples may be used.

Furthermore, although in the preceding examples the therapeutic agent used is a therapeutic agent for neurodegenerative diseases, any other therapeutic agent may be used, in combination with the appropriate vectorizing agent, to obtain a pharmaceutical composition having a targeted action on an organ and a particular disease of this organ.

The invention claimed is:

1. A dendritic chelated complex of the following formula I:

$$[[MC]\text{-}E_n\text{-}[D]_m\text{-}X_{1p1}X_{2p2}X_{3p3}X_{4p4}]^{z-}zB^+ \quad \text{Formula I}$$

wherein:
M is a magnetic or scintigraphic marker,
C is a chelating agent for the magnetic marker M,
[MC] is a chelate of the magnetic-marker M,
E is a spacer,
n=0 or 1,
[D] is a dendritic structure, the core of which comprises at least one group derived from benzyl alcohol or from a benzyl amine, the benzyl ring of which is substituted at positions 3, 4, 5 with chains composed of polyethylene glycol units,
m is an integer equal to 1 or 2 or 4,
$X_1$ is a group for increasing the lipophilicity of the complex,
p1 is an integer equal to 0 to 12, limits included,
$X_2$ is a group for increasing the specificity of the complex for a particular organ,
p2 is an integer equal to 0, 1, 2 or 4, limits included,
$X_3$ is a group having a therapeutic activity,
p3 is an integer equal to 0, 1, 2 or 4, limits included,
$X_4$ is a $CH_3$ group,
p1+p2+p3+p4=3 when m=1 or p1+p2+p3+p4=6 when m=2 or p1+p2+p3+p4=12 when m=4,
p4 is an integer equal to 0 to 12, limits included,
B is a counterion,
z is an integer equal to 0, 1, 2, 3 or 4.

2. The complex according to claim 1, wherein the chelating agent C is diethylenetriaminepentaacetic acid (DTPA), a catechol-derived tripod or an 8-hydroxyquinoline-derived tripod.

3. The complex according to claim 1 wherein each dendrite of the dendritic structure [D] is a polyethylene glycol chain comprising 3 or 4 ethylene glycol units.

4. The complex according to claim 1, wherein m=1.

5. The complex according to claim 1, wherein m=2 or 4.

6. The complex according to claim 1, wherein:
n=p1=p2=p3=0,
$X_4$ is $CH_3$,
p4=6,
each dendrite of the dendritic structure [D] is a chain comprising 3 ethylene glycol units,
m=2,
C is diethylenetriaminepentaacetic acid,
M is $Gd^{3+}$,
B is $Na^+$, and
z=1
of formula II-1 below:

Formula II-1
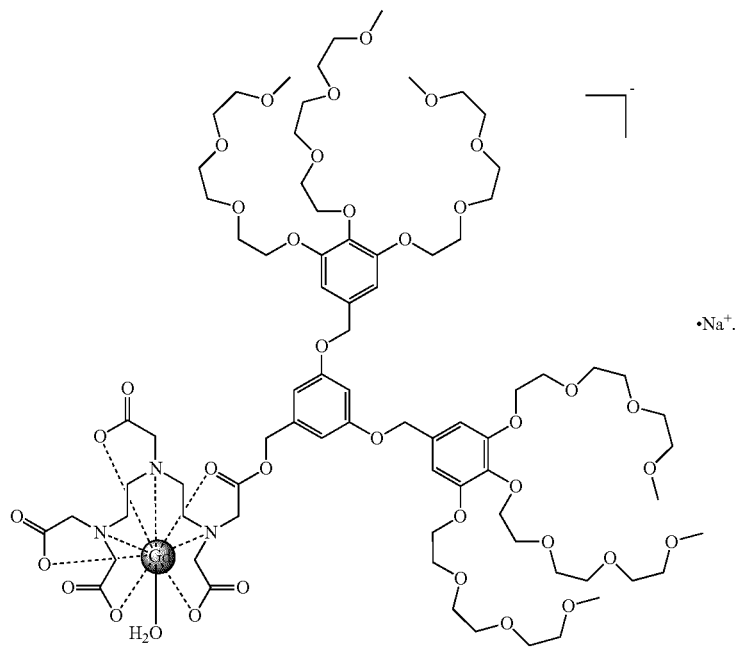
•Na+.
7. The complex according to claim 1, characterized in that:
n=p1=p2=p3=0,
$X_4$ is $CH_3$,
p4=6,
each dendrite of the dendritic structure [D] is a polyethylene glycol chain having 3 ethylene glycol units,
m=2,
C is diethylenetriaminepentaacetic acid,
M is $Mn^{2+}$,
B is $Na^+$, and
z=2,
of formula II-2 below:
Formula II-2
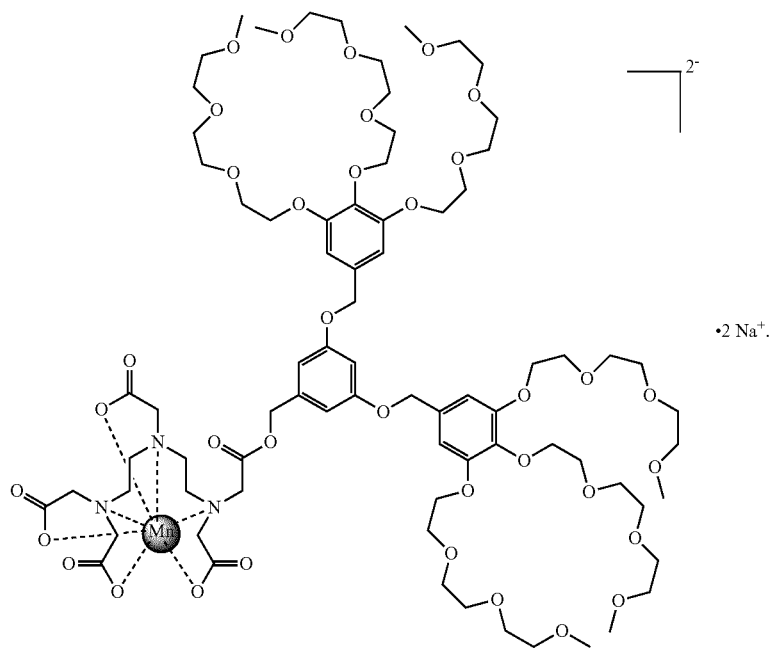
•2 Na+.

8. The complex according to claim 1, wherein:
n=p1=p2=p3=0,
$X_4$ is $CH_3$,
p4=6,
each dendrite of the dendritic structure [D] is a polyethylene glycol chain having 3 ethylene glycol units,
m=2,
C is diethylenetriaminepentaacetic acid,
M is 99 $mTc^{3+}$,
B is $Na^+$, and
z=1,
of formula II-3 below:

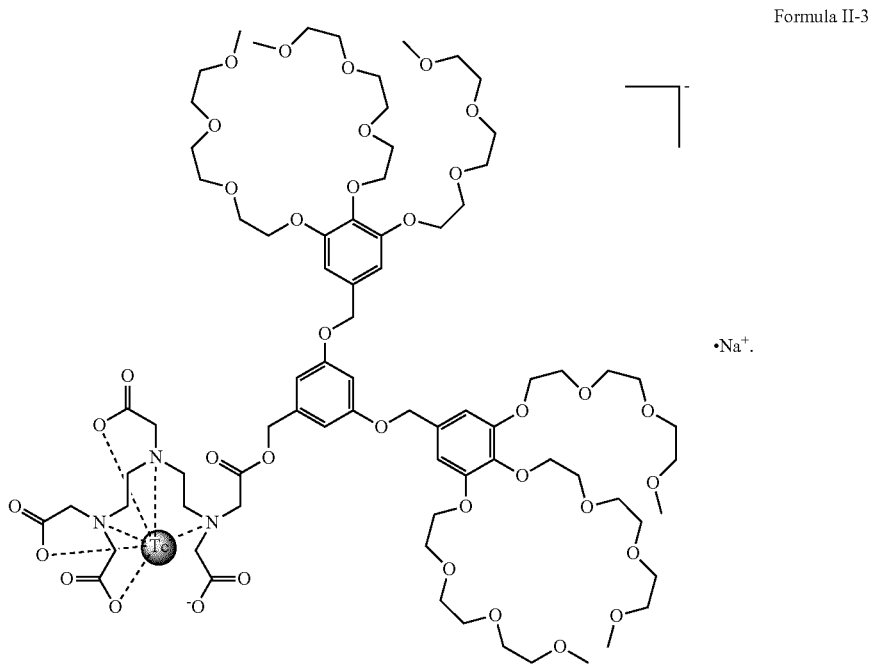

Formula II-3

9. The complex according to claim 1, wherein:
C is a catechol-derived tripod,
n=1,
E is an ethylenediamine or butanediamine chain,
each dendrite of the dendritic structure [D] is a chain having 3 or 4 ethylene glycol units,
m=1,
M is $Gd^{3+}$,
p1=p2=p3=0,
$X_4$ is $CH_3$,
p4=3,
B is $Na^+$, and
z=3.

10. The complex according to claim 1, wherein:
C is a catechol-derived tripod,
n=1,
E is an ethylenediamine or butanediamine chain,
each dendrite of the dendritic structure [D] is a chain having 3 or 4 ethylene glycol units,
m=1
M is $Mn^{2+}$,
p1=p2=p3=0,
$X_4$ is $CH_3$,
p4=3,
B is $Na^+$, and
z=4.

11. The complex according to claim 1, wherein:
C is a catechol-derived tripod,
n=1,
E is an ethylenediamine or butanediamine chain,
each dendrite of the dendritic structure [D] is a chain having 3 or 4 ethylene glycol units,
m=1,
M is 99 $mTc^{3+}$,
p1=p2=p3=0
$X_4$ is $CH_3$,
p4=3,
B is $Na^+$, and
z=3.

12. The complex according to claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=1,
M is $Gd^{3+}$,
p1=p2=p3=0,
$X_4$ is $CH_3$,
p4=3,
and
z=0.

13. The complex according to any claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=1,
M is $Mn^{2+}$,
p1=p2=p3=0,
$X_4$ is $CH_3$, p4=3,
B is Na⁺, and
z=1.

14. The complex according to any claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=1,
M is 99 mTc$^{3+}$,
p1=p2=p3=0,
X$_4$ is CH$_3$,
p4=3,
and
z=0.

15. The complex according to claim 1, wherein:
C is a catechol-derived tripod,
n=1,
E is an ethylenediamine or butanediamine chain,
each dendrite of the dendritic structure [D] is a chain comprising 3 or 4 ethylene glycol units,
m=2 or 4,
M is Gd$^{3+}$,
p4=6 when m=2 or p4=12 when m=4,
B is Na⁺, and
z=3.

16. The complex according to claim 1, wherein:
C is a catechol-derived tripod,
n=1,
E is an ethylenediamine or butanediamine chain,
each dendrite of the dendritic structure [D] is a chain comprising 3 or 4 ethylene glycol units,
m=2 or 4,
M is Mn$^{2+}$,
p4=6 when m=2 or p4=12 when m=4,
B is Na⁺, and
z=4.

17. The complex according to claim 1, wherein:
C is a catechol-derived tripod,
n=1,
E is an ethylenediamine or butanediamine chain,
each dendrite of the dendritic structure [D] is a chain comprising 3 or 4 ethylene glycol units,
m=2 or 4,
M is 99 mTc$^{3+}$,
p1=p2=p3=0,
X$_4$ is CH$_3$,
p4=6 when m=2 or p4=12 when m=4,
B is Na⁺, and
z=3.

18. The complex according to claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=2 or 4,
M is Gd$^{3+}$,
p1=p2=p3=0,
X$_4$ is CH$_3$,
p4=6 when m=2 or p4=12 when m=4,
and
z=0.

19. The complex according to claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=2 or 4,
M is Mn$^{2+}$,
p1=p2=p3=0,
X$_4$ is CH$_3$,
p1=p2=p3=0,
X$_4$ is CH$_3$,
p4=6 when m=2 or p4=12 when m=4,
B is Na⁺, and
z=1.

20. The complex according to claim 1, wherein:
C is an 8-hydroxyquinoline-derived tripod,
n=1,
E is an ethylenediamine or butanediamine chain,
each dendrite of the dendritic structure [D] is a chain comprising 3 or 4 ethylene glycol units,
m=2 or 4,
M is 99 mTc$^{3+}$,
p1=p2=p3=0,
X$_4$ is CH$_3$,
p1=p2=p3=0,
X$_4$ is CH$_3$,
p4=6 when m=2 or p4=12 when m=4,
and
z=0.

21. The complex according to claim 1, wherein:
n=p2=p3=p4=0,
M is Gd$^{3+}$,
each dendrite of the dendritic structure [D] is a chain comprising 3 or 4 ethylene glycol units,
m=1,
C is diethylenetriaminepentaacetic acid,
X$_1$ is a tert-butyl (tBu) group,
p1=3,
B is Na⁺, and
z=1.

22. The complex according to claim 1, wherein:
n=p2=p3=p4=0,
M is Mn$^{2+}$,
each dendrite of the dendritic structure [D] is a chain comprising 3 or 4 ethylene glycol units,
m=1,
C is diethylenetriaminepentaacetic acid,
X$_1$ is a tert-butyl (tBu) group,
p1=3,
B is Na⁺, and
z=2.

23. The complex according to claim 1, wherein:
n=p2=p3=p4=0,
M is 99 mTc$^{3+}$,
each dendrite of the dendritic structure [D] is a chain comprising 3 or 4 ethylene glycol units,
m=1,
C is diethylenetriaminepentaacetic acid,
X$_1$ is a tert-butyl (tBu) group,
p1=3,
B is Na⁺, and
z=1.

24. The complex according to claim 1, wherein:
n=p2=p3=p4=0,
M is $Gd^{3+}$,
each dendrite of the dendritic structure [D] is a chain comprising 3 or 4 ethylene glycol units,
m=2 or 4,
C is diethylenetriaminepentaacetic acid,
$X_1$ is a tert-butyl (tBu) group,
p1=6 when m=2 or p1=12 when m=4,
B is $Na^+$, and
z=1.

25. The complex according to claim 1, wherein:
n=p2=p3=p4=0,
M is $Mn^{2+}$,
each dendrite of the dendritic structure [D] is a chain comprising 3 or 4 ethylene glycol units,
m=2 or 4,
C is diethylenetriaminepentaacetic acid,
$X_1$ is a tert-butyl (tBu) group,
p1=6 when m=2 and p1=12 when m=4,
B is $Na^+$, and
z=2.

26. The complex according to claim 1, wherein:
n=p2=p3=p4=0,
M is 99 $mTc^{3+}$,
each dendrite of the dendritic structure [D] is a chain comprising 3 or 4 ethylene glycol units,
m=2 or 4,
C is diethylenetriaminepentaacetic acid,
$X_1$ is a tert-butyl (tBu) group,
p1=6 when m=2 or p1=12 when m=4,
B is $Na^+$, and
z=1.

27. The complex according to claim 1, wherein:
n=p3=p4=0,
each dendrite of the dendritic structure [D] is a chain comprising 3 or 4 ethylene glycol units,
C is diethylenetriaminepentaacetic acid,
M is $Gd^{3+}$,
m=1,
$X_1$ is a tert-butyl (tBu) group,
p1=2,
$X_2$ is L-dopamine,
p2=1,
B is $Na^+$, and
z=1.

28. The complex according to claim 1, wherein:
n=p3=p4=0,
each dendrite of the dendritic structure [D] is a chain comprising 3 or 4 ethylene glycol units,
C is diethylenetriaminepentaacetic acid,
M is $Mn^{2+}$,
m=1,
$X_1$ is a tert-butyl (tBu) group,
p1=2,
$X_2$ is L-dopamine,
p2=1,
B is $Na^+$, and
z=2.

29. The complex according to claim 1, wherein:
n=p3=p4=0,
each dendrite of the dendritic structure [D] is a chain comprising 3 or 4 ethylene glycol units,
C is diethylenetriaminepentaacetic acid,
M is 99 $mTc^{3+}$,
m=1,
$X_1$ is a tert-butyl (tBu) group,
p1=2,
$X_2$ is L-dopamine,
p2=1,
B is $Na^+$, and
z=1.

30. The complex according to claim 1, wherein:
n=p3=p4=0,
each dendrite of the dendritic structure [D] is a chain comprising 3 or 4 ethylene glycol units,
C is diethylenetriaminepentaacetic acid,
M is $Gd^{3+}$,
m=2,
$X_1$ is a tert-butyl (tBu) group,
p1=4,
$X_2$ is L-dopamine,
p2=2,
B is $Na^+$, and
z=1.

31. The complex according to claim 1, wherein:
n=p3=p4=0,
each dendrite of the dendritic structure [D] is a chain comprising 3 or 4 ethylene glycol units,
C is diethylenetriaminepentaacetic acid,
M is $Mn^{2+}$,
m=2,
$X_1$ is a tert-butyl (tBu) group,
p1=4,
$X_2$ is L-dopamine,
p2=2,
B is $Na^+$, and
z=2.

32. The complex according to claim 1, wherein:
n=p3=p4=0,
each dendrite of the dendritic structure [D] is a chain comprising 3 or 4 ethylene glycol units,
C is diethylenetriaminepentaacetic acid,
M is 99 $mTc^{3+}$,
m=2,
$X_1$ is a tert-butyl (tBu) group,
p1=4,
$X_2$ is L-dopamine,
p2=2,
B is $Na^+$, and
z=1.

33. The complex according to claim 1, wherein:
C is either diethylenetriaminepentaacetic acid, or a catechol-derived or 8-hydroxyquinoline-derived tripod,
n=0 or 1,
E is an ethylenediamine chain or butanediamine chain when n=1,
each dendrite of the structure [D] is a chain comprising 3 or 4 ethylene glycol units,
m=1 or 2 or 4,
M is $Gd^{3+}$, or $Mn^{2+}$, or 99 $mTc^{3+}$,
$X_1$ is a tert-butyl (tBu) group,
p1 is an integer equal to between 0 and 12, limits included,
$X_2$ is L-dopamine,
p2 is an integer equal to 0, 1, 2 or 4, limits included,
$X_3$ is a therapeutic agent,
p3 is an integer equal to 0, 1, 2 or 4, limits included,
p4=0,
B is $Na^+$, and
z=0, 1, 2, 3 or 4.

34. A method for synthesizing the complex according to claim 6, comprising the following steps:
a) reaction of triethylene glycol monomethyl ether with tosyl chloride, b) reaction of the tosylate obtained in step a) with methyl 3,4,5-trihydroxybenzoate,
c) reduction of the product obtained in step b), preferably with LiAlH$_4$, so as to obtain the corresponding alcohol,
d) bromination of the product obtained in step c),
e) reaction of the product obtained in step d) with methyl 3,5-dihydroxybenzoate,
f) reaction of the product obtained in step e), preferably with LiAlH$_4$,
g) reaction of the product obtained in step with diethylenetriaminepentaacetic dianhydride,
h) reaction of the product obtained in step g) with Gd chloride or Mn chloride or pertechnetate.

35. A method for synthesizing the complex according to claim 21, comprising the following steps:
a) synthesis of tert-butoxytriethylene glycol from tert-butanol,
b) reaction of the product obtained in step a) with tosyl chloride,
c) reaction of the tosylate obtained in step b) with methyl 3,4,5-trihydroxybenzoate,
d) reduction of the product obtained in step c), preferably with LiAlH$_4$, so as to obtain the corresponding alcohol,
e) reaction of the product obtained in step d) with diethylenetriaminepentaacetic dianhydride,
f) reaction of the product obtained in step e) with Gd chloride or Mn chloride or pertechnetate.

36. A method for synthesizing the complex according to claim 27 comprising the following steps:
a) synthesis of tert-butoxytriethylene glycol from tert-butanol,
b) reaction of the product obtained in step a) with tosyl chloride,
a') reaction of methyl 3,4,5-trihydroxybenzoate with acetic anhydride,
b') reaction of the product obtained in step a') with allyl bromide,
c') basic hydrolysis of the product obtained in step b'), preferably with potassium carbonate,
d') reaction of the product obtained in step c') with the tosylate obtained in step b),
e') deprotection of the alcohol function of the product obtained in step d'),
a") protection of L-dopamine with Fmoc chloride
b") reaction of the product obtained in step a") with allyl bromide,
c") reaction of the product obtained in step b") with morpholine,
d") esterification of the product obtained in step c"),
e") saponification of the product obtained in step d"),
f") esterification of the product obtained in step e") with the product obtained in step e'),
g") reduction of the product obtained in step f") so as to obtain the corresponding alcohol,
h") reaction of the product obtained in step g") with diethylenetriaminepentaacetic dianhydride,
i") reaction of the product obtained in step h") with Gd (III), chloride, Mn (II) chloride or pertechnetate.

37. A method for synthesizing the complex according to claim 30, comprising the following steps:
a) synthesis of tert-butoxytriethylene glycol from tert-butanol,
b) reaction of the product obtained in step a) with tosyl chloride,
a') reaction of methyl 3,4,5-trihydroxybenzoate with acetic anhydride,
b') reaction of the product obtained in step a') with allyl bromide,
c') basic hydrolysis of the product obtained in step b') with potassium carbonate,
d') reaction of the product obtained in step c') with the tosylate obtained in step b),
e') deprotection of the alcohol function of the product obtained in step d'),
a") protection of L-dopamine with Fmoc chloride,
b") reaction of the product obtained in step a") with allyl bromide,
c") reaction of the product obtained in step b") with morpholine,
d") esterification of the product obtained in step c"),
e") saponification of the product obtained in step d"),
f") esterification of the product obtained in step e") with the product obtained in step e'),
g") reduction of the product obtained in step f"), preferably with LiAlH$_4$, so as to obtain the corresponding alcohol,
h") bromination of the product obtained in step g"),
i") reaction of the product obtained in step h") with methyl 3,5-dihydroxybenzoate,
j") reduction of the product obtained in step i"), preferably with LiAlH$_4$, so as to obtain the corresponding alcohol,
k") reaction of the product obtained in step j") with diethylenetriaminepentaacetic dianhydride,
l") reaction of the product obtained in step k") with Gd (III) chloride, Mn (II) chloride or pertechnetate.

38. A pharmaceutical composition, comprising at least one complex as claimed in claim 1, in a pharmaceutically acceptable excipient.

39. A method for the detection of neurodegenerative diseases selected from the group consisting of Alzheimer's disease, Parkinson's disease and multiple sclerosis comprising administering the pharmaceutical composition of claim 38 to a subject in need of said detection.

40. The complex according to claim 1, wherein M is chosen from Gd$^{3+}$, Mn$^{2+}$ and 99 mTc$^{3+}$ ions.

41. A dendritic chelated complex according to claim 1, wherein X$_1$ is a tert-butyl (tBu) group.

42. A dendritic chelated complex according to claim 1, wherein X$_2$ is a group for increasing the specificity of the complex for the brain.

43. A dendritic chelated complex according to claim 1, wherein X$_2$ is a L-dopamine group.

44. A dendritic chelated complex according to claim 1, wherein X$_3$ is a group having a therapeutic activity for neurodegenerative diseases.

45. A dendritic chelated complex according to claim 1, wherein X$_3$ is a group having a therapeutic activity for neurodegenerative diseases chosen in the group of Alzheimer's disease, Parkinson's disease and multiple sclerosis.

46. A dendritic chelated complex according to claim 1, wherein B is Na$^+$ or K$^+$.

* * * * *